US012709759B2

(12) United States Patent
Lagudah et al.

(10) Patent No.: US 12,709,759 B2
(45) Date of Patent: Aug. 18, 2026

(54) *PUCCINIA* RESISTANCE GENE

(71) Applicant: Commonwealth Scientific and Industrial Research Organisation, Acton (AU)

(72) Inventors: Evans Lagudah, Ngunnawal (AU); Jianping Zhang, Acton (AU); Peng Zhang, Cobbitty (AU)

(73) Assignee: Commonwealth Scientific and Industrial Research Organisation

(*) Notice: Subject to any disclaimer, the term of this patent is extended or adjusted under 35 U.S.C. 154(b) by 0 days.

(21) Appl. No.: 17/775,556

(22) PCT Filed: Nov. 10, 2020

(86) PCT No.: PCT/AU2020/051224

§ 371 (c)(1),
(2) Date: May 9, 2022

(87) PCT Pub. No.: WO2021/092647

PCT Pub. Date: May 20, 2021

(65) Prior Publication Data

US 2022/0403408 A1 Dec. 22, 2022

(30) Foreign Application Priority Data

Nov. 11, 2019 (AU) ................................ 2019904238

(51) Int. Cl.
*C12N 15/82* (2006.01)
*A01H 1/04* (2006.01)
*C07K 14/415* (2006.01)

(52) U.S. Cl.
CPC ......... *C12N 15/8282* (2013.01); *A01H 1/045* (2021.01); *C07K 14/415* (2013.01)

(58) Field of Classification Search
None
See application file for complete search history.

(56) References Cited

U.S. PATENT DOCUMENTS

| | | | |
|---|---|---|---|
| 4,399,216 | A | 8/1983 | Axel et al. |
| 4,945,050 | A | 7/1990 | Sanford et al. |
| 5,004,863 | A | 4/1991 | Umbeck |
| 5,104,310 | A | 4/1992 | Saltin |
| 5,141,131 | A | 8/1992 | Miller, Jr. et al. |
| 5,159,135 | A | 10/1992 | Umbeck |
| 5,164,316 | A | 11/1992 | McPherson et al. |
| 5,177,010 | A | 1/1993 | Goldman et al. |
| 5,384,253 | A | 1/1995 | Krzyzek et al. |
| 5,416,011 | A | 5/1995 | Hinchee et al. |
| 5,451,513 | A | 9/1995 | Maliga et al. |
| 5,459,252 | A | 10/1995 | Conkling et al. |
| 5,463,174 | A | 10/1995 | Moloney et al. |
| 5,472,869 | A | 12/1995 | Zrzyzek et al. |
| 5,518,908 | A | 5/1996 | Corbin et al. |
| 5,545,818 | A | 8/1996 | McBride et al. |
| 5,569,834 | A | 10/1996 | Hinchee et al. |
| 5,589,617 | A | 12/1996 | Nehra et al. |
| 5,625,136 | A | 4/1997 | Koziel et al. |
| 5,877,402 | A | 3/1999 | Maliga et al. |
| 5,932,479 | A | 8/1999 | Daniell et al. |
| 6,100,447 | A | 8/2000 | Wu et al. |
| 6,541,257 | B2 | 4/2003 | Lemaux et al. |
| 2018/0305711 | A1* | 10/2018 | Lagudah ............ C12N 15/8282 |

FOREIGN PATENT DOCUMENTS

| | | | |
|---|---|---|---|
| AU | 667939 | | 4/1996 |
| CA | 20992588 | | 7/2008 |
| EP | 0256223 | A1 | 2/1988 |
| EP | 0154204 | B1 | 1/1994 |
| EP | 0275957 | B1 | 3/1998 |
| WO | WO1987005327 | | 9/1987 |
| WO | WO1987006614 | | 11/1987 |
| WO | WO1991002071 | | 2/1991 |
| WO | WO1991013992 | | 9/1991 |
| WO | WO1992009696 | | 6/1992 |
| WO | WO1993021335 | | 10/1993 |
| WO | WO1997048814 | | 12/1997 |
| WO | WO1999005265 | | 2/1999 |
| WO | WO1999014314 | | 3/1999 |
| WO | 2014194371 | | 12/2014 |
| WO | WO2017024053 | | 2/2017 |
| WO | WO2018086623 | | 5/2018 |

OTHER PUBLICATIONS

Zhang et al., Nature Communications 12.1 (2021): 3378 (Year: 2021).*
GenBank Accession MN531844.1; Available Apr. 27, 2021 https://www.ncbi.nlm.nih.gov/nuccore/MN531844 (Year: 2021).*
Eitas et al., Current opinion in plant biology 13.4 (2010): 472-477 (Year: 2010).*
Van Wersch et al., Plant Communications 1.1 (2020) 100016 (Year: 2020).*
Guo et al, 2004, Proc. Natl. Acad. Sci. USA 101: 9205-9210 (Year: 2004).*
Mago et al., Theoretical and applied genetics 132 (2019): 371-382 (Year: 2018).*
Märkle et al., Essays in biochemistry 66.5 (2022): 551-560 (Year: 2022).*
Mago et al.(2019, Theoretical and Applied Genetics 132:372-381, provided by Applicant (Year: 2019).*
Periyannan et al., (2017) "An overview of genetic rust resistance: From broad to specific mechanisms", PLOS Pathogens, vol. 13, No. 7, e1006380, pp. 1-6.
GenBank Accession No. AK358531.1, Jul. 25, 2016, "*Hordeum vulgare* subsp. *vulgare* mRNA for predicted protein, partial cds, clone: NIASHv1078A16", 2 pages.

(Continued)

*Primary Examiner* — Brent T Page
(74) *Attorney, Agent, or Firm* — Rudy J. Ng; Christian S. Hans; Bozicevic, Field & Francis LLP

(57) ABSTRACT

The present invention relates to a plant which has integrated into its genome an exogenous polynucleotide encoding a polypeptide which confers resistance to at least one strain of *Puccinia graminis*.

19 Claims, 27 Drawing Sheets

Figure 1:
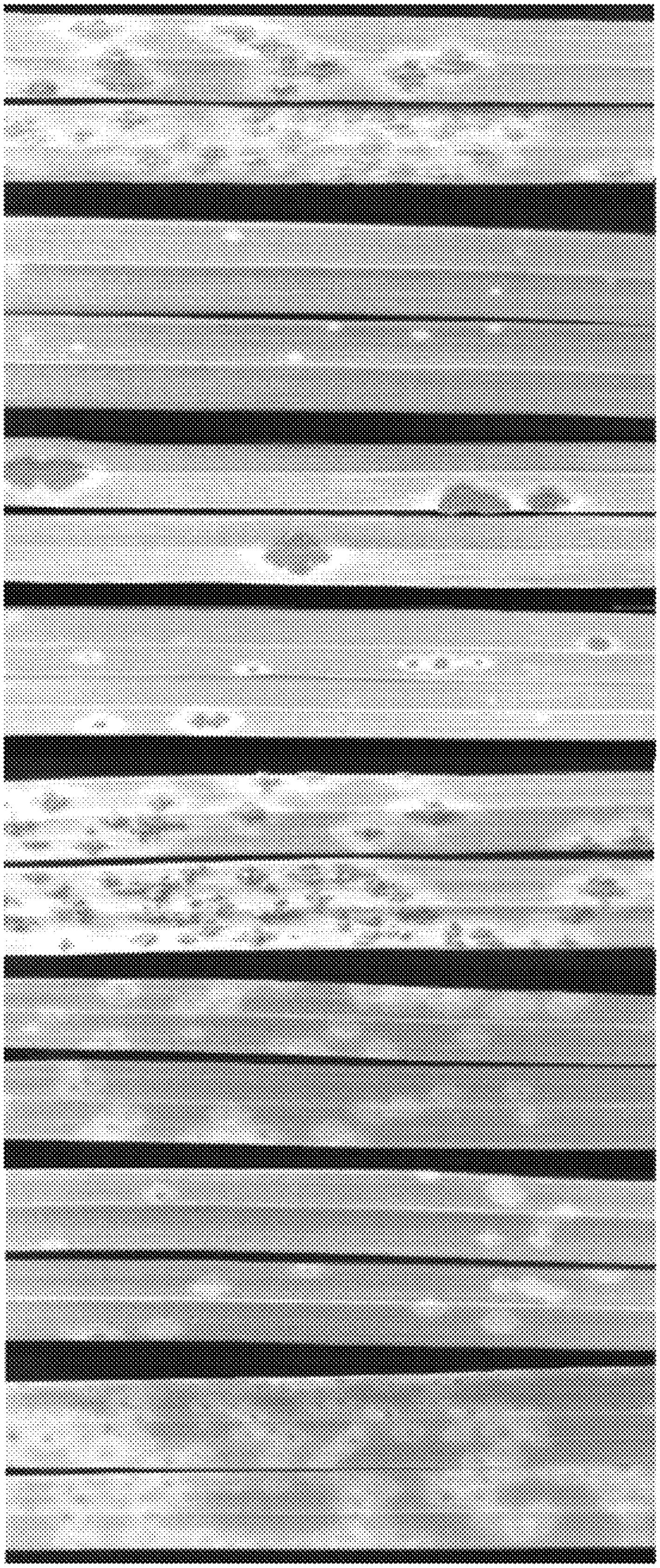

Specification includes a Sequence Listing.

(56) References Cited

OTHER PUBLICATIONS

GenBank Accession No. MG818992.1, Apr. 2, 2018, "*Aegilops tauschii* subsp. *tauschii* putative disease resistance protein RPP13 (RPP13L4) gene, complete cds", 4 pages.
GenBank Accession No. SPT21024.1, 7, Jun. 2018, 2 pages.
Mago et al., (2019) "Transfer of stem rust resistance gene SrB from Thinopyrum ponticum into wheat and development of a closely linked PCR-based marker", Theoretical and Applied Genetics, 132: 371-382.
Steuernagel et al., (2016) "Rapid cloning of disease-resistance genes in plants using mutagenesis and sequence capture", Nature Biotechnology, 34: 652-655.
Zhang et al., (2019) "A strategy for identifying markers linked with stem rust resistance in wheat harbouring an alien chromosome introgression from a non-sequenced genome", Theoretical and Applied Genetics, 132: 125-135.
Zhang et al., (2020) "How Target-sequence Enrichment and Sequencing (TEnSeq) pipelines have catalysed resistance gene cloning in the wheat-rust pathosystem", Frontiers in Plant Science, 11: 678.
GenBank Accession No. ALO61074.1, Nov. 22, 2015 "RGA1-A [Secale cereale]", 2 pages.
GenBank Accession No. AMY98955, Apr. 25, 2016 "Late blight resistance protein Rpi-amr3 [Solanum Americanum]", 2 pages.
GenBank Accession No. ANJ02805, Jun. 2, 120156 "R8 resistance protein [Solanum demissum]", 2 pages.
GenBank Accession No. ANZ78204, Sep. 19, 2016 "Pvr4 [Capsicum annuum]", 2 pages.
GenBank Accession No. AOR08328, Nov. 24, 2016 "Tsw [Capsicum chinense]", 2 pages.
GenBank Accession No. APF29096, Feb. 15, 2017 "NBS-LRR type R protein Pigm-R6 [Oryza sativa Indica Group]", 2 pages.
GenBank Accession No. ARO38245.1, May 16, 2017 "Disease resistance protein NLR1 [Triticum aestivum]", 2 pages.
GenBank Accession No. ATE88460.1, Oct. 2, 2017 "Sr13 [Triticum turgidum subsp.durum]", 2 pages.
GenBank Accession No. AVK42833.1, Mar. 10, 2018 "Sr21 [Triticum monococcum]", 2 pages.
GenBank Accession No. AYV61514.1, Nov. 18, 2018 "Sr46 protein [Aegilops tauschii]", 2 pages.
GenBank Accession No. BAA76282, Feb. 15, 2008 "Pib [Oryza sativa Japonica Group]", 2 pages.
GenBank Accession No. BAC67706, Feb. 13, 2004 "R-protein [Arabidopsis thaliana]", 2 pages.
GenBank Accession No. BAH20862, Aug. 6, 2009 "NBS-LLR disease resistance protein [Oryza sativa Japonica Group]", 2 pages.
GenBank Accession No. BAJ25849, Nov. 12, 2010 "Resistant protein [Oryza sativa Japonica Group]", 2 pages.
GenBank Accession No. BAJ33559, Dec. 27, 2011 "CC-NBS-LRR type resistance protein [Capsicum Chinese]", 3 pages.
GenBank Accession No. BAJ33561, Dec. 27, 2011 "CC-NBS-LRR type resistance protein, partial [Capsicum Chinese]", 3 pages.
GenBank Accession No. BAJ33562, Dec. 27, 2011 "CC-NBS-LRR type resistance protein, partial [Capsicum Chinese]", 3 pages.
GenBank Accession No. BAJ33563, Dec. 27, 2011 "CC-NBS-LRR type resistance protein, partial [Capsicum Chinese]", 2 pages.
GenBank Accession No. BAJ33564, Dec. 27, 2011 "CC-NBS-LRR type resistance protein, partial [Capsicum Chinese]", 3 pages.
GenBank Accession No. BAJ33565, Dec. 27, 2011 "CC-NBS-LRR type resistance protein, partial [Capsicum Chinese]", 3 pages.
GenBank Accession No. BAJ33566, Dec. 27, 2011 "CC-NBS-LRR type resistance protein, partial [Capsicum Chinese]", 3 pages.
GenBank Accession No. BAM17521, Sep. 3, 2013 "N' tobamovirus resistance protein [Nicotiana sylvestris]", 3 pages.
GenBank Accession No. BAN59294, Jul. 2, 2013 "Pii protein [Oryza sativa Japonica Group]", 2 pages.
GenBank Accession No. CAB50786, Jul. 20, 1999 "Rx protein [Solanum tuberosum]", 2 pages.
GenBank Accession No. CAB56299, Nov. 14, 2006 "NBS-LRR protein [Solanum acaule]", 2 pages.
GenBank Accession No. CAC29241, Dec. 31, 2003 "MLA6 protein [Hordeum vulgare subsp. vulgare]", 2 pages.
GenBank Accession No. CAL64731, Oct. 27, 2006 "Unnamed protein product [Zea mays]", 2 pages.
GenBank Accession No. CUM44200.1, Feb. 12, 2016 "Unnamed protein product [Triticum aestivum]", 2 pages.
GenBank Accession No. CUM44213.1, Feb. 12, 2016 "Unnamed protein product [Triticum aestivum]", 3 pages.
GenBank Accession No. CZT14023.1, Apr. 16, 2016 "PM2 protein [Triticum aestivum]", 2 pages.
GenBank Accession No. MN531843, Apr. 27, 2021 "Thinopyrum obtusiflorum wheat stem rust immune receptor (Sr26) gene, complete cds", 3 pages.
GenBank Accession No. MN531844, Apr. 27, 2021 "Thinopyrum obtusiflorum wheat stem rust immune receptor (Sr61) gene, complete cds", 2 pages.
GenBank Accession No. NP_001067618, Jun. 8, 2010 "Os11g02449000 [Oryza sativa Japonica Group]", 4 pages.
GenBank Accession No. NP_001172592, Jun. 8, 2010 "Os01g0782100 [Oryza sativa Japonica Group]", 4 pages.
GenBank Accession No. NP_001233995, Apr. 17, 2013 "Os01g0782100 [Oryza sativa Japonica Group]", 2 pages.
GenBank Accession No. Q9ZSD1, Nov. 28, 2006 "Resistance protein candidate RGC2B", 2 pages.
Gennaro et al., (2009) "A candidate for Lr19, an exotic gene conditioning leaf rust resistance in wheat." Functional & Integrative Genomics, vol. 9, pp. 325-334.
Haft et al., (2005) "A guild of 45 CRISPR-associated (Cas) protein families and multiple CRISPR/Cas subtypes exist in prokaryotic genomes." PLoS Computational Biology, vol. 1, No. 6, e60, pp. 0474-0483.
Hatta et al., (2018) "The wheat Sr22, Sr33, Sr35 and Sr45 genes confer resistance against stem rust in barley." BioRxiv CSH, 19 pages. https://www.biorxiv.org/content/early/2018/07/374637.
Hellinga, H. W., (1997) "Rational protein design: combining theory and experiment." Proceedings of the National Academy of Sciences, vol. 94, No. 19, pp. 10015-10017.
Henikoff et al., (2004) "TILLING. Traditional mutagenesis meets functional genomics." Plant Physiology, vol. 135, vol. 2, pp. 630-636.
Hinchee et al., (1988) "Production of transgenic soybean plants using Agrobacterium-mediated DNA transfer." Bio/technology, vol. 6, No. 8, pp. 915-922.
International Preliminary Report dated May 17, 2022, PCT Application No. PCT/AU2020/051224, 9 pages.
International Search Report dated Dec. 23, 2020, PCT Application No. PCT/AU2020/051224, 6 pages.
Jinek et al. (2012) "A programmable dual-RNA-guided DNA endonuclease in adaptive bacterial immunity." Science, vol. 337, No. 6096, pp. 816-821.
Joshi, Chandrashekar P., (1987) "An inspection of the domain between putative TATA box and translation start site in 79 plant genes." Nucleic Acids Research, vol. 15, No. 16, pp. 6643-6653.
Knott, D. R., (1961) "The inheritance of rust resistance. VI. The transfer of stem rust resistance from Agropyron elongatum to common wheat." Canadian Journal of Plant Science, vol. 41, No. 1, pp. 109-123.
Kourelis et al., (2018) "Defended to the nines: 25 years of resistance gene cloning identifies nine mechanisms for R protein function." The Plant Cell, vol. 30, No. 2, pp. 285-299.
Kumar et al., (2016) "MEGA7: molecular evolutionary genetics analysis version 7.0 for bigger datasets." Molecular biology and evolution, vol. 33, No. 7, pp. 1870-1874.
Langridge et al., (2001) "Trends in genetic and genome analyses in wheat: a review." Australian Journal of Agricultural Research, vol. 52, No. 12, pp. 1043-1077.
Li et al., (2019) "Emergence of the Ug99 lineage of the wheat stem rust pathogen through somatic hybridisation." Nature Communications, vol. 10, No. 1, 5068, 60 pages.
Liang et al., (2017) "Efficient DNA-free genome editing of bread wheat using CRISPR/Cas9 ribonucleoprotein complexes." Nature Communications, vol. 8, No. 1, 14261, 5 pages.

(56) References Cited

OTHER PUBLICATIONS

Liang et al., (2018) "Genotyping genome-edited mutations in plants using CRISPR ribonucleoprotein complexes." Plant Biotechnology Journal, vol. 16, No. 12, pp. 2053-2062.
Liu et al., (2010) "Diagnostic and co-dominant PCR markers for wheat stem rust resistance genes Sr25 and Sr26." Theoretical and Applied Genetics, vol. 120, pp. 691-697.
Lu et al., (1993) "High efficiency retroviral mediated gene transduction into single isolated immature and replatable CD34 (3+) hematopoietic stem/progenitor cells from human umbilical cord blood." The Journal of Experimental Medicine, vol. 178, No. 6, pp. 2089-2096.
Ma et al., (2015) "A robust CRISPR/Cas9 system for convenient, high-efficiency multiplex genome editing in monocot and dicot plants." Molecular Plant, vol. 8, No. 8, pp. 1274-1284.
Mago et al., (2015) "The wheat Sr50 gene reveals rich diversity at a cereal disease resistance locus." Nature Plants, vol. 1, No. 12, 3 pages.
Mago et al., (2005) "Development of PCR markers for the selection of wheat stem rust resistance genes Sr24 and Sr26 in diverse wheat germplasm." Theoretical and Applied Genetics, vol. 111, pp. 496-504.
Makarova et al., (2016) "An updated evolutionary classification of CRISPR-Cas systems." Nature Reviews Microbiology, vol. 13, No. 11, pp. 722-736.
Marchal et al., (2018) "BED-domain-containing immune receptors confer diverse resistance spectra to yellow rust." Nature Plants, vol. 4, No. 9, pp. 662-668.
McHale et al., (2006) "Plant NBS-LRR proteins: adaptable guards." Genome Biology, vol. 7, 11 pages.
McIntosh et al., (1977) "Inheritance of leaf rust and stem rust resistances in wheat cultivars Agent and Agatha." Australian Journal of Agricultural Research, vol. 28, No. 1, pp. 37-45.
McIntosh, R. A., (1995) "Wheat Rusts: an atlas of resistance genes." Csiro Publishing.
Medberry et al., (1992) "The Commelina yellow mottle virus promoter is a strong promoter in vascular and reproductive tissues." The Plant Cell, vol. 4, No. 2, pp. 185-192.
Medberry et al., (1993) "Identification of cis elements involved in Commelina yellow mottle virus promoter activity." The Plant Journal, vol. 3, No. 4, pp. 619-626.
Meyers et al., (1999) "Plant disease resistance genes encode members of an ancient and diverse protein family within the nucleotide-binding superfamily." The Plant Journal, vol. 20, No. 3, pp. 317-332.
Michelmore et al., (1998) "Clusters of resistance genes in plants evolve by divergent selection and a birth-and- death process." Genome Research, vol. 8, No. 11, pp. 1113-1130.
Niedz et al., (1995) "Green fluorescent protein: an in vivo reporter of plant gene expression." Plant Cell Reports, vol. 14, pp. 403-406.
Olivera et al. (2012) "Races of Puccinia graminis f. sp. tritici with combined virulence to Sr13 and Sr9e in a field stem rust screening nursery in Ethiopia." Plant Disease, vol. 96, No. 5, pp. 623-628.
Pan et al., (2000) "Divergent evolution of plant NBS-LRR resistance gene homologues in dicot and cereal genomes." Journal of Molecular Evolution, vol. 50, pp. 203-213.
Patpour et al., (2018) BGRI Technical workshop.8 pages.
Periyannan et al., (2013) "The gene Sr33, an ortholog of barley Mla genes, encodes resistance to wheat stem rust race Ug99." Science, vol. 341, No. 6147, pp. 786-788.
Pretorius et al., (2015) "Assessing the vulnerability of wheat germplasm from Bangladesh and Nepal to Ug99 stem rust." Phytoparasitica, vol. 43, pp. 637-645.
Saintenac et al., (2013) "Identification of wheat gene Sr35 that confers resistance to Ug99 stem rust race group." Science, vol. 341, No. 6147, pp. 783-786.
Saitou N, Nei M., (1987) "The neighbor-joining method: a new method for reconstructing phylogenetic trees." Mol Biol Evol., vol. 4, No. 4, pp. 406-425.
Singh et al., (2015) "Emergence and spread of new races of wheat stem rust fungus: continued threat to food security and prospects of genetic control." Phytopathology, vol. 105, No. 7, pp. 872-884.
Stemmer, Willem P., (1994) "DNA shuffling by random fragmentation and reassembly: in vitro recombination for molecular evolution." Proceedings of the National Academy of Sciences, vol. 91, No. 22, pp. 10747-10751.
Steuernagel et al., (2017) "MutRenSeq: a method for rapid cloning of plant disease resistance genes." Wheat Rust Diseases: Methods and Protocols, vol. 1659, pp. 215-229.
Sun et al., (2016) "Engineering herbicide-resistant rice plants through CRISPR/Cas9-mediated homologous recombination of acetolactate synthase." Molecular Plant, vol. 9, No. 4, pp. 628-631.
Svitashev et al., (2016) "Genome editing in maize directed by CRISPR-Cas9 ribonucleoprotein complexes." Nature Communications, vol. 7, No. 1, pp. 1-7.
Takken et al., (2006) "Resistance proteins: molecular switches of plant defence." Current Opinion in Plant Biology, vol. 9, No. 4, pp. 383-390.
Tameling et al., "The tomato R gene products I-2 and MI-1 are functional ATP binding proteins with ATPase activity." The Plant Cell, vol. 14, No. 11, pp. 2929-2939.
Traut, Thomas W., (1994) "The functions and consensus motifs of nine types of peptide segments that form different types of nucleotide-binding sites." European Journal of Biochemistry, vol. 222, No. 1, pp. 9-19.
Wang et al., (2011) "Molecular analysis of common wheat genes encoding three types of cytosolic heat shock protein 90 (Hsp90): functional involvement of cytosolic Hsp90s in the control of wheat seedling growth and disease resistance." New Phytologist, vol. 191, No. 2, pp. 418-431.
Wang et al., (2019) "Ligand-triggered allosteric ADP release primes a plant NLR complex." Science, vol. 364: eaav5868, 11 pages.
Wang et al., (2020) "Horizontal gene transfer of Fhb7 from fungus underlies Fusarium head blight resistance in wheat." Science, vol. 368: eaba5435, 10 pages.
WO Invitation to Correct Defects dated Nov. 11, 2020, PCT Application No. PCT/AU2020/051224, 3 pages.
WO First Written Opinion dated Dec. 23, 2020, PCT Application No. PCT/AU2020/051224 , 8 pages.
WO Response to Invitation to Correct Defects filed Nov. 20, 2020, PCT Application No. PCT/AU2020/051224, 20 pages.
WO Specification dated Nov. 10, 2020 , 110 pages.
Wulff et al., (2018) "Wheat-the cereal abandoned by GM." Science, vol. 361, No. 6401, pp. 451-452.
Zhang et al., (2017) "Identification and characterization of Sr13, a tetraploid wheat gene that confers resistance to the Ug99 stem rust race group." Proceedings of the National Academy of Sciences, vol. 114, No. 45, pp. E9483-E9492.
Zwer et al., "Wheat stem rust in Australia dash 1969-1985." Australian Journal of Agricultural Research, vol. 43. No. 3, pp. 399-431.
GenBank Accession No. ABB91438, Dec. 5, 2005, "R-FOM-2 [Cucumis melo]", 2 pages.
GenBank Accession No. ABC73398, Dec. 29, 2006, "Piz-t [Oryza sativa Japonica Group]", 2 pages.
GenBank Accession No. ABC94599, Dec. 29, 2006, "NBS-LRR type R protein [Oryza sativa Indica Group]", 2 pages.
GenBank Accession No. ABE68835, Jun. 10, 2010, "Root-knot nematode resistance protein [Capsicum annuum]", 2 pages.
GenBank Accession No. ABS29034, Aug. 30, 2007, "Lr1 disease resistance protein [Triticum aestivum]", 2 pages.
GenBank Accession No. ABY58665.1, May 18, 2010, "Powdery mildew resistance protein PM3 [Triticum dicoccoides]", 2 pages.
GenBank Accession No. ACB72455.1, Dec. 3, 2008, "Pc protein B [Sorghum bicolor]", 2 pages.
GenBank Accession No. ACI25288.1, Oct. 6, 2008, "Late blight resistance protein Rpi-sto1 [Solanum stoloniferum]", 2 pages.
GenBank Accession No. ACI25289.1, Oct. 6, 2008, "Late blight resistance protein Rpi-sto1 [Solanum stoloniferum] Late blight resistance protein Rpi-sto1 [Solanum stoloniferum]", 2 pages.
GenBank Accession No. ACJ66594, Aug. 23, 2010, "Late blight resistance protein [Solanum venturii]", 2 pages.

(56) References Cited

OTHER PUBLICATIONS

GenBank Accession No. ACJ66595.1, Aug. 23, 2010, "Late blight resistance protein [Solanum verturii]", 2 pages.
GenBank Accession No. ACJ66596, Aug. 23, 2010, "Late blight resistance protein [Solanum verturii]", 2 pages.
GenBank Accession No. ACN56757.1, Jun. 12, 2009, "Disease resistance protein RPP13 variant [Arabidopsis thaliana]", 2 pages.
GenBank Accession No. ACN56765.1, Jun. 12, 2009, "Disease resistance protein RPP13 variant [Arabidopsis thaliana]", 2 pages.
GenBank Accession No. ACN56766.1, Jun. 12, 2009, "Disease resistance protein RPP13 variant [Arabidopsis thaliana]", 2 pages.
GenBank Accession No. ACN56776.1, Jun. 12, 2009, "Disease resistance protein RPP13 variant [Arabidopsis thaliana]", 2 pages.
GenBank Accession No. ACN79513, Sep. 11, 2009 "Resistance protein Pid3 [Oryza sativa Indica Group]", 2 pages.
GenBank Accession No. ACU65454, Aug. 25, 2009 "R2-like protein [Solanum sp. AM-3778-16]", 2 pages.
GenBank Accession No. ACU65455, Aug. 25, 2009 "Rpi protein [Solanum sp. ABPT]", 2 pages.
GenBank Accession No. ACU65456, Aug. 25, 2009 "R2 protein [Solanum demissum]", 2 pages.
GenBank Accession No. ACU65457, Aug. 25, 2009 "Rpi protein [Solanum bulbocastanum]", 2 pages.
GenBank Accession No. ACZ65484, May 5, 2010 "MLA2 [Hordeum vulgare subsp. vulgare]", 2 pages.
GenBank Accession No. ACZ65485, May 5, 2010 "MLA3 [Hordeum vulgare subsp. vulgare]", 2 pages.
GenBank Accession No. ACZ65486, May 5, 2010 "MLA8 [Hordeum vulgare subsp. vulgare]", 2 pages.
GenBank Accession No. ACZ65487, May 5, 2010 "MLA9 [Hordeum vulgare subsp. vulgare]", 2 pages.
GenBank Accession No. ACZ65490, May 5, 2010 "MLA18-2 [Hordeum vulgare subsp. vulgare]", 2 pages.
GenBank Accession No. ACZ65492, May 5, 2010 "MLA22 [Hordeum vulgare subsp. vulgare]", 2 pages.
GenBank Accession No. ACZ65493, May 5, 2010 "MLA23 [Hordeum vulgare subsp. vulgare]", 2 pages.
GenBank Accession No. ACZ65495, May 5, 2010 "MLA27-1 [Hordeum vulgare subsp. vulgare]", 2 pages.
GenBank Accession No. ACZ65496, May 5, 2010 "MLA27-2 [Hordeum vulgare subsp. vulgare]", 2 pages.
GenBank Accession No. ACZ65497, May 5, 2010 "MLA28 [Hordeum vulgare subsp. vulgare]", 2 pages.
GenBank Accession No. ACZ65500, May 5, 2010 "MLA32 [Hordeum vulgare subsp. vulgare]", 2 pages.
GenBank Accession No. ACZ65501, May 5, 2010 "MLA34 [Hordeum vulgare subsp. vulgare]", 2 pages.
GenBank Accession No. ACZ65502, May 5, 2010 "MLA35-1 [Hordeum vulgare subsp. vulgare]", 2 pages.
GenBank Accession No. ADB07392, Jan. 10, 2010 "BPH14-1 [Oryza sativa Indica Group]", 3 pages.
GenBank Accession No. ADF29624, Apr. 15, 2010 "Pi36 [Oryza sativa Indica Group]", 2 pages.
GenBank Accession No. ADK47521, Dec. 13, 2010 "RDG2A [Hordeum vulgare subsp. vulgare]", 2 pages.
GenBank Accession No. ADU57957, Dec. 21, 2012 "Disease resistance protein CYR1 [Vigna mungo]", 2 pages.
GenBank Accession No. ADX06722, Feb. 13, 2011 "Mla1 [Triticum monococcum]", 2 pages.
GenBank Accession No. AEC47890, Jun. 12, 2011 "R3b [Solanum demissum]", 2 pages.
GenBank Accession No. AER13157, Nov. 22, 2011 "Rpp4C4 [Phaseolus vulgaris]", 3 pages.
GenBank Accession No. AFM35701, Jun. 18, 2012 "Blast resistance protein [Oryza sativa Indica Group]", 2 pages.
GenBank Accession No. AGI99538, Apr. 16, 2013 "NB-LRR receptor [Vigna unguiculata]", 2 pages.
GenBank Accession No. AGP75918.1, Aug. 16, 2013 "CNL9 [Triticum monococcum subsp. monococcum]", 2 pages.
GenBank Accession No. AGQ17378.1, Aug. 16, 2013 "RGA1a [Aegilos tauschii]", 2 pages.
GenBank Accession No. AGT37271, Sep. 13, 2013 "RPP7 [Arabidopsis thaliana]", 2 pages.
GenBank Accession No. AIB02970, Jun. 8, 2014 "Ph-3 resistance protein [Solanum pimpinellifolium]", 2 pages.
GenBank Accession No. AIC32313, Apr. 7, 2015 "NB-LRR disease resistance protein Rpg1r [Glycine max]", 3 pages.
GenBank Accession No. AIU36098, Mar. 24, 2015 "Vat protein [Cucumis melo]", 2 pages.
GenBank Accession No. AKS24975.1, Dec. 16, 2015 "NBS-LRR type R protein [Oryza sativa Japonica Group]", 2 pages.
Arora et al., (2019) "Resistance gene cloning from a wild crop relative by sequence capture and association genetics." Nature Biotechnology, vol. 37, No. 2 pp. 139-143.
AU_AU2019904238 Provisional Application (Nov. 11, 2019) "Puccinia Resistance Gene", 146 pages.
Ayliffe et al., (2013) "A simple method for comparing fungal biomass in infected plant tissues." Molecular Plant-Microbe Interactions, vol. 26, No. 6, pp. 658-667.
Begemann et al., (2017) "Precise insertion and guided editing of higher plant genomes using Cpf1 CRISPR nucleases." Scientific Reports, vol. 7, No. 1, 11606, 6 pages.
Bender et al., (2016) "Development of a Greenhouse Screening Method for Adult Plant Response in Wheat to Stem Rust." Plant Disease, vol. 100, No. 8, pp. 1627-1633.
Bevan et al., (1983) "Strcuture and transcription of the nopaline synthase gene region of T-DNA." Nucleic Acids Research, vol. 11, No. 2, pp. 369-385.
Bulgarelli et al., (2010) "The CC-NB-LRR-type Rdg2a resistance gene confers immunity to the seed-borne barley leaf stripe pathogen in the absence of hypersensitive cell death." PLoS One, vol. 5, No. 9, e12599, 14 pages.
Cadwell et al., (1992) "Randomization of genes by PCR mutagenesis." Genome Research, vol. 2, No. 1, pp. 28-33.
Chen et al., (2018) "Identification and characterization of wheat stem rust resistance gene Sr21 effective against the Ug99 race group at high temperature." PLoS Genetics, vol. 14, No. 4, e1007287, 21 pages.
Chen et al., (2020) "Wheat gene Sr60 encodes a protein with two putative kinase domains that confers resistance to stem rust." New Phytologist, vol. 225, No. 2, pp. 948-959.
Comai et al., (2004) "Efficient discovery of DNA polymorphisms in natural populations by Ecotilling." The Plant Journal, vol. 37, No. 5, pp. 778-786.
Cooley et al., (2000) "Members of the Arabidopsis HRT/RPP8 family of resistance genes confer resistance to both viral and oomycete pathogens." The Plant Cell, vol. 12, No. 5, pp. 663-676.
Cui et al., (2018) "Development of perennial wheat through hybridization between wheat and wheatgrasses: a review." Engineering, vol. 4, No. 4, pp. 507-513.
Curiel et al., (1992) "High-Efficiency Gene Transfer Mediated by Adenovirus Coupled to DNA-Polylysine Complexes." Human Gene Therapy, vol. 3, pp. 147-154.
Dilbirligi et al., (2003) "Identification and analysis of expressed resistance gene sequences in wheat." Plant Molecular Biology, vol. 53, pp. 771-787.
Dundas et al., (2015) Chromosome Engineering and Physical Mapping of the Thinopyrum ponticum Translocation in Wheat Carrying the Rust Resistance Gene Sr23, Crop Science, vol. 55, pp. 648-657.
Enkhbayar et al., (2003) "Structural Principles of Leucine-Rich Repeat (LRR) Proteins." Proteins: Structure, Function, and Bioinformatics, vol. 54, No. 3, pp. 394-403.
EP_Response as filed on Sep. 11, 2024 to EP search opinion, EP application No. EP20887302.6, 15 pages.
EP Extended Search Report dated Dec. 14, 2023, EP Application No. EP20887302.6, 8 pages.
GenBank Accession No. AAA91022.1, Jun. 21, 1995, "L6 [Linum usitatissimum]", 2 pages.
GenBank Accession No. AAC49408, Aug. 28, 1996, "PRF [Solanum lycopersicum]", 2 pages.
GenBank Accession No. AAC97933, Dec. 23, 1998, "Disease resistance protein [Solanum lycopersicum]", 2 pages.

(56) References Cited

OTHER PUBLICATIONS

GenBank Accession No. AAF36987, Mar. 1, 2000, "Viral resistance protein [Arabidopsis thaliana]", 2 pages.
GenBank Accession No. AAF42831.1, Mar. 12, 2000, "RPP13 [Arabidopsis thaliana]", 2 pages.
GenBank Accession No. AAF42832.1, Mar. 12, 2000, "RPP13 [Arabidopsis thaliana]", 2 pages.
GenBank Accession No. AAG31014, Aug. 4, 2010, "Tospovirus resistance protein B [Solanum lycopersicum]", 2 pages.
GenBank Accession No. AAG37354, Jul. 24, 2016, "MLA1 [Hordeum vulgare subsp. Vulgar]", 2 pages.
GenBank Accession No. AAO16014, Feb. 21, 2003, "CC-NBS-LRR resistance protein MLA13 [Hordeum vulgare]", 2 pages.
GenBank Accession No. AAO43441, Mar. 4, 2003, "MLA1 [Hordeum vulgare subsp. Vulgar]", 2 pages.
GenBank Accession No. AAQ10735, Sep. 26, 2003, "Tm-2 ToMV resistance protein [Solanum lycopersicum]", 2 pages.
GenBank Accession No. AAQ10736, Sep. 26, 2003, "Tm-2'ToMV resistance protein [Solanum lycopersicum]", 2 pages.
GenBank Accession No. AAQ55540, Apr. 8, 2004, "MLA7 [Hordeum vulgare]", 2 pages.
GenBank Accession No. AAQ55541, Apr. 8, 2004, "MLA10 [Hordeum vulgare]", 2 pages.
GenBank Accession No. AAQ96158, Feb. 6, 2004, "Powdery mildew resistance protein PM3b [Triticum aestivum]", 2 pages.
GenBank Accession No. AAR19096, Feb. 11, 2004, "NBS-LRR type disease resistance protein RPG1-B [Glycine max]", 2 pages.
GenBank Accession No. AAS49213, Aug. 18, 2006, "Disease resistance protein [Glycine max]", 2 pages.
GenBank Accession No. AAS49233, Apr. 6, 2004, "Rust resistance protein [Zea mays]", 3 pages.
GenBank Accession No. AAT08955, Jul. 11, 2017, "CC-NBS-LRR [Helianthus annuus]", 3 pages.
GenBank Accession No. AAW48299, Apr. 14, 2004, "Potato late blight resistance protein R3a [Solanum tuberosum]", 2 pages.
GenBank Accession No. AAX31149, Oct. 27, 2005, "RXO1 disease resistance protein [Zea mays]", 2 pages.
GenBank Accession No. AAX89382, Apr. 21, 2008, "NB-LRR type disease resistance protein Rps1-k1 [Glycine max]", 2 pages.
GenBank Accession No. AAY21626, Oct. 17, 2005, "Powdery mildew resistance protein PM3A [Triticum aestivum]", 2 pages.
GenBank Accession No. AAY21627, Oct. 17, 2005, "Powdery mildew resistance protein PM3D [Triticum aestivum]", 2 pages.
GenBank Accession No. AAY33493.1, Jul. 26, 2016, "NBS-LRR, partial [Oryza sativa Indica Group]", 2 pages.
GenBank Accession No. AAZ23113, Oct. 17, 2005, "Powdery mildew resistance protein PM3F [Triticum aestivum]", 2 pages.
GenBank Accession No. AAZ95005, Oct. 18, 2005, "Late blight resistance protein Rpi-blb2 [Solanum bulbocastanum]", 2 pages.
GenBank Accession No. ABB78077.1, Jun. 19, 2006, "Powdery mildew resistance protein PM3C [Triticum aestivum]", 2 pages.
GenBank Accession No. ABB78078.1, Jun. 19, 2006, "Powdery mildew resistance protein PM3E [Triticum aestivum]", 2 pages.
GenBank Accession No. ABB78079.1, Jun. 19, 2006, "Powdery mildew resistance protein PM3G [Triticum aestivum]", 2 pages.
GenBank Accession No. ABB88855, Jul. 26, 2016, "NBS-LRR disease resistance protein [Oryza sativa Indica Group]", 2 pages.

* cited by examiner b a b

SEQUENCE LISTING

```
<160> NUMBER OF SEQ ID NOS: 46

<210> SEQ ID NO 1
<211> LENGTH: 880
<212> TYPE: PRT
<213> ORGANISM: Thinopyrum ponticum

<400> SEQUENCE: 1

Met Val Gly Ile Met Val Ser Ala Ser Thr Gly Ala Met Asn Ser Leu
1               5                   10                  15

Leu Gly Lys Leu Thr Ala Leu Met Gly Glu Glu Phe Ala Lys Leu Lys
            20                  25                  30

Asn Met Arg Lys Glu Val Gln Phe Ile Arg Asp Glu Leu Gly Ser Met
        35                  40                  45

Lys Asp Ala Leu Glu Arg Leu Ala Asp Val Asp Glu Leu Asp Pro Gln
    50                  55                  60

Thr Lys Ser Trp Arg Asn Thr Leu Arg Glu Ile Ser Tyr Asp Ile Glu
65                  70                  75                  80

Asp Ile Ile Asp Asp Phe Met Gln Asn Ile Gly Glu Lys Asp Lys Asn
                85                  90                  95

Ser Gly Phe Ile His Lys Thr Ile Arg Arg Leu Arg Thr Leu Arg Cys
            100                 105                 110

Arg His Arg Ile Val Gly Gln Ile Gln Glu Ile Lys Lys Leu Val His
        115                 120                 125

Glu Thr Ser Gly Arg Arg Lys Arg Tyr Ala Leu His Thr Ile Ile Pro
    130                 135                 140

Pro Ser Asn Asn Asp Val Ala Ile Asp Pro Arg Val Ile Thr Leu Tyr
145                 150                 155                 160

Gly Met Ala Ala Asn Leu Val Gly Met Glu Gly Ser Lys Asn Glu Leu
                165                 170                 175

Val Asn Trp Leu Glu Asp Lys Asp Lys Gln Leu Lys Val Val Ser Ile
            180                 185                 190

Val Gly Phe Gly Gly Leu Gly Lys Thr Thr Leu Ala Asn Glu Val Tyr
        195                 200                 205

His Met Leu Arg Pro Gly Ser Thr Phe Ser Ala Phe Val Pro Val Ser
    210                 215                 220

Gln Lys Pro Asn Ile Leu Asn Leu Leu Arg Ser Leu Leu Ser Gln Leu
225                 230                 235                 240

Gly Ile Glu Pro Thr Ile Tyr Ala Cys Val Ser Asp Leu Ile Asp Lys
                245                 250                 255

Leu Arg Glu Arg Leu Gln Thr Lys Arg Tyr Leu Ile Ile Ile Asp Asp
            260                 265                 270

Leu Trp Asp Val Ser Ala Trp Asn Ile Ile Lys Cys Ala Leu Pro Asp
        275                 280                 285

Asn Asp Cys Gly Ser Arg Val Val Val Thr Thr Arg Ile Gln Glu Val
    290                 295                 300

Ala Thr Ala Cys Cys Ser His Arg Arg Asp Tyr Ile Leu Gln Met Lys
305                 310                 315                 320

Pro Leu Ser Asp Glu Asp Ser Lys Arg Leu Phe Tyr Gly Arg Ile Phe
                325                 330                 335
```

```
Gly Ser Thr Glu Ala Cys Pro Arg His Leu Arg Asp Val Ser Leu Glu
            340                 345                 350

Val Leu Lys Lys Cys Gly Gly Leu Pro Leu Ala Ile Thr Ser Ile Ala
        355                 360                 365

Ser Met Leu Ala Thr Glu Gly Phe Glu Gln Lys Glu Arg Trp Lys Asp
    370                 375                 380

Val Arg Asn Ser Leu Gly Ser Gly Thr Asn Gly Thr Leu Asn Gly Val
385                 390                 395                 400

Arg Gln Ile Leu Asn Leu Ser Tyr Lys Asp Leu Pro Cys Tyr Leu Lys
                405                 410                 415

Thr Cys Phe Leu Tyr Leu Gly Met Tyr Pro Glu Asp Tyr Thr Ile Lys
            420                 425                 430

Arg Ser Asp Leu Glu Cys Gln Trp Met Ala Glu Gly Phe Val Ser Lys
        435                 440                 445

Glu Asn Gly His Ser Val Glu Lys Thr Ala Arg Ser Tyr Phe Asn Glu
    450                 455                 460

Leu Val Asn Arg Ser Leu Ile Gln Pro Val Glu Phe Asp Asn Thr Gly
465                 470                 475                 480

Ser Val Thr Gln Cys Arg Val His Asp Met Met Leu Asp Leu Ile Met
                485                 490                 495

Leu Lys Ser Val Glu Glu Asn Phe Leu Thr Val Val Asp Asp Thr Lys
            500                 505                 510

Asp Ile Thr Gly Leu Asp Tyr Lys Ala Arg Arg Leu Ser Ile Arg Leu
        515                 520                 525

Asp Gly Ala Ser Asn Asp Leu Thr Thr Leu Leu Asn Asn Ile Ser Met
    530                 535                 540

Ser His Val Arg Ser Val Met Phe Phe Gly Ser Ser Gln Asn Thr Pro
545                 550                 555                 560

Pro Leu Ser Lys Phe Lys Phe Leu Arg Val Leu Phe Ile Asn Leu His
                565                 570                 575

Arg Ala Thr Ile Asp Leu Thr Gly Leu Cys Lys Leu Tyr Gln Leu Arg
            580                 585                 590

Tyr Leu Trp Ile Ser Asp Thr Cys His Tyr Gln Val Pro Thr Arg Ile
        595                 600                 605

Arg Glu Leu Gln His Leu Glu Thr Leu Asn Val Lys Arg Gly Leu Pro
    610                 615                 620

Asp Gly Ile Gly Asn Met Lys Ser Leu Arg Tyr Leu Arg Ala Phe Asp
625                 630                 635                 640

Leu Arg Leu Asn Thr Leu Asp Asn Ile Lys Ser Leu Gly Glu Leu Thr
                645                 650                 655

Asn Leu Arg Cys Leu Phe Leu Glu Asp Arg Phe Ser Leu Ser Cys Arg
            660                 665                 670

Lys Lys Gly Met Asp Ala Leu Cys Phe Ser Leu Gly Arg Leu Cys Ser
        675                 680                 685

Leu Glu Thr Leu Ser Val Asn Leu Ser Glu Cys Ile Asp Asp Leu Met
    690                 695                 700

Leu Cys Phe Pro Pro Ser Thr Pro Tyr His Leu Glu Arg Leu Leu Val
705                 710                 715                 720

Ser Ser Asn Cys Trp Phe Ser Lys Val Pro Thr Trp Met Gly Glu Leu
                725                 730                 735

Cys Tyr Leu Arg Glu Leu Gln Cys His Leu Asp Glu Trp Leu Asn Asp
            740                 745                 750

Gly Val Gly Ile Leu Ala Glu Leu Pro Ala Leu Thr Asp Leu Asp Leu
```

```
        755                 760                 765

Val Ile Gln Arg Leu Arg His Lys Lys Ile Val Ile Tyr Lys Lys Ala
    770                 775                 780

Phe Pro Ala Leu Arg Arg Phe Glu Leu Val Leu Ser Asp Pro Ser Tyr
785                 790                 795                 800

Leu Thr Phe Arg Ala Gly Ala Met Pro Lys Leu Gln Arg Leu Lys Leu
                805                 810                 815

Thr Phe Glu Cys Tyr Glu Trp Gly Asn His Gly Val Ala Pro Thr Gly
            820                 825                 830

Ile Gly Tyr Leu Leu Ala Leu Glu Asp Leu Ser Ala Val Ile Ile Cys
        835                 840                 845

Gln Thr Ala Glu Ala Asp Thr Glu Trp Ala Glu Ser Ala Leu Arg Asp
    850                 855                 860

Ala Ile Ala Arg His Pro Arg Cys Pro Arg Leu Gln Ile Ser Ser Gly
865                 870                 875                 880


<210> SEQ ID NO 2
<211> LENGTH: 2640
<212> TYPE: DNA
<213> ORGANISM: Thinopyrum ponticum

<400> SEQUENCE: 2

atggtcggaa taatggtgag cgcttctact ggtgccatga actccctgct gggtaagttg     60

accgccctca tgggggagga gtttgctaag ctgaaaaaca tgcgaaagga ggtgcagttc    120

attagggatg agcttggcag catgaaggat gctctagaga ggcttgcaga tgtggacgag    180

ctagatccac aaaccaagag ctggagaaac acactgaggg agatctctta tgatatcgag    240

gacatcattg atgacttcat gcaaaacatt ggggagaaag acaagaactc cgggtttatc    300

cataagacca ttcgacgtct cagaactttg agatgccgtc accggattgt gggccagatt    360

caagagataa agaaacttgt ccatgagaca agcggtcgtc gcaaaagata tgcgcttcat    420

actattatcc caccatcgaa caatgatgtt gccattgacc cacgagttat aacactttat    480

ggaatggcgg ctaaccttgt tggcatggag gggtcaaaga atgagcttgt taattggcta    540

gaagacaagg ataagcagtt gaaggtggta tcaattgtgg gatttggagg tctaggtaaa    600

acaacacttg ccaatgaggt gtaccatatg ctcaggccag gatctacctt tagtgcattt    660

gtgccagttt ctcaaaaacc taacattcta aatcttcttc gtagtttact atcccaactt    720

gggatagagc caactattta tgcttgcgtg tcagacctta tcgacaagct tagagaacgt    780

ctccaaacta agaggtactt gattataatt gatgatctat gggatgtatc agcctggaat    840

attattaaat gtgcactccc agataatgat tgtggcagca gagtagtagt aactacaaga    900

attcaagaag tggctacagc atgttgctcc catcgccgtg attacatttt acaaatgaag    960

ccccttagcg acgaagattc aaaaaggttg ttttatggca ggatatttgg ctccacagaa   1020

gcttgccctc ggcaccttag agacgtttca cttgaagttc taaaaaaatg tggtggtttg   1080

cctcttgcaa ttactagtat agctagcatg cttgccaccg aaggtttcga acaaaaggaa   1140

aggtggaagg atgtacgaaa ttctttgggt tcaggaacaa atggcacgtt gaatggggtg   1200

cggcaaatct taaacctcag ctacaaagat cttccttgtt acctaaagac atgcttcttg   1260

tatcttggta tgtatcctga ggactacacc ataaagaggt ctgatctaga atgccaatgg   1320

atggcagaag gctttgttag taaagaaaat ggacatagtg tggagaaaac tgcaagaagt   1380

tatttcaacg agcttgtcaa taggagcctt attcaacccg tagaatttga caatacggga   1440
```

-continued

```
tctgtgacac aatgtagagt acatgatatg atgcttgatc ttatcatgct caagtctgta   1500

gaagagaatt ttctcacggt agtggatgac acaaaggaca ttacgggatt ggattacaag   1560

gctcgtcggc tgtctatccg cttggatggt gccagtaatg atctaacaac attactgaat   1620

aacattagta tgtcacatgt tcggtcggtt atgttctttg ggagctctca gaatacacct   1680

cctctatcaa agttcaagtt cctccgagtt ctttttatta acctccatcg tgctacaatt   1740

gacctcactg gactgtgcaa attatatcag ttgaggtatt tatggattag tgacacttgt   1800

cattaccaag taccaacacg gattagagag ttacaacact tggaaacact gaatgttaaa   1860

agagggctgc ctgatgggat tggcaacatg aaatccctac gatatctacg tgcatttgat   1920

ttacggttga acaccctaga caatatcaag agccttggag agctgaccaa tctgagatgt   1980

ttatttcttg aagacagatt ttcattaagt tgtcggaaga aaggcatgga tgctctatgc   2040

ttttccttgg gaaggctttg tagcctagag accctgtctg tcaatctcag cgaatgcata   2100

gatgacttga tgctctgttt tcctccctca actccctacc accttgagag actccttgtg   2160

tcatcgaatt gttggttttc taaggtccct acctggatgg gagaactatg ttacctgcga   2220

gagttacaat gtcatcttga tgaatggcta aatgatggcg tcggtatcct tgcagagctg   2280

cctgccctca ctgacctcga tttagtaatc caaagactac gacacaaaaa gattgtcatc   2340

tacaagaaag cattccctgc tctaaggcgt tttgaacttg tattaagcga cccctcgtac   2400

ctaaccttcc gggccggtgc aatgcccaag ctccaaaggc tgaagctaac gtttgagtgc   2460

tatgaatggg ggaaccatgg ggtcgcacct accggcatcg ggtacttatt agcacttgaa   2520

gatttgtctg cagttatcat ctgtcaaact gctgaagctg atacggaatg ggcagagtct   2580

gccttgaggg acgctattgc caggcatcca aggtgtcctc gtcttcaaat atcaagcggc   2640
```

<210> SEQ ID NO 3
<211> LENGTH: 935
<212> TYPE: PRT
<213> ORGANISM: Thinopyrum ponticum

<400> SEQUENCE: 3

```
Met Glu Ala Ala Leu Val Ser Ala Ala Thr Gly Ala Leu Lys Pro Val
1               5                   10                  15

Leu Glu Lys Leu Gly Ala Leu Val Gly Asp Lys Tyr Lys Arg Phe Lys
            20                  25                  30

Gly Val Arg Gly Glu Ile Lys Ser Leu Thr His Glu Leu Ala Thr Met
        35                  40                  45

Asp Ala Phe Leu Leu Lys Met Ser Asp Glu Glu Asp Pro Asp Ala Gln
    50                  55                  60

Asp Lys Ala Trp Met Asn Glu Val Arg Glu Leu Ser Tyr Asp Met Glu
65                  70                  75                  80

Asp Ser Ile Asp Asp Phe Met Gln Ser Val Asp Ala Glu Asp Thr Lys
                85                  90                  95

Pro Asp Gly Phe Leu Glu Lys Met Lys Asn Leu Leu Gly Lys Ile Lys
            100                 105                 110

Ala Arg Arg Arg Ile Gly Asn Glu Val Gln Asp Leu Lys Lys Gln Ile
        115                 120                 125

Ile Glu Val Ala Gln Arg Asn Glu Arg Tyr Lys Ala Arg Glu Ala Phe
    130                 135                 140

Ser Lys Lys Glu Asn Ala Thr Ile Asp Pro Arg Ala Leu Ala Ile Phe
145                 150                 155                 160

Gln His Ala Ser Glu Leu Val Gly Ile Asp Glu Pro Lys Ala Glu Leu
```

-continued

```
                165                 170                 175

Ile Lys Leu Leu Thr Gln Gly Glu Ser Thr Arg Asp Lys Met Asn Leu
            180                 185                 190

Val Ser Ile Val Gly Ser Gly Gly Met Gly Lys Thr Thr Leu Ala Asn
        195                 200                 205

Gln Val Tyr Gln Asp Leu Lys Gly Lys Phe Lys Cys Arg Val Phe Leu
    210                 215                 220

Ser Val Ser Arg Asn Pro Asp Met Met Asn Ile Phe Arg Thr Ile Leu
225                 230                 235                 240

Ser Gln Val Ser Gly Gln Arg Tyr Gly Asp Thr Glu Ala Gly Ser Ile
                245                 250                 255

Gln Gln Leu Ile Ile Lys Ile Ala Glu Phe Leu Leu Asp Lys Arg Tyr
            260                 265                 270

Phe Val Val Leu Asp Asp Ile Trp Asp Val Val Thr Trp His Thr Ile
        275                 280                 285

Lys His Ala Phe Pro Met Arg Ser Ser Gly Ser Ile Ile Ile Thr Thr
    290                 295                 300

Thr Arg Ile Asn Glu Val Ala Lys Ser Cys Cys Ser Thr Pro Phe Ser
305                 310                 315                 320

Gly Asp Ile Tyr Cys Ile Arg Pro Leu Asp Met Val His Ser Arg Lys
                325                 330                 335

Leu Phe Tyr Thr Arg Leu Phe Asn Ser Glu Glu Asn Cys Pro Ser His
            340                 345                 350

Leu Lys Lys Val Ser Glu Asp Ile Leu Lys Lys Cys Asp Gly Leu Pro
        355                 360                 365

Leu Ala Ile Ile Ala Ile Ser Gly Leu Leu Ala Asn Thr Glu Arg Thr
    370                 375                 380

Glu Gly Pro Trp Lys Gln Val Lys Asp Ser Ile Gly Arg Ala Leu Gln
385                 390                 395                 400

Arg Asn Thr Ile Val Gln Glu Met Met Lys Ile Leu Ser Leu Ser Tyr
                405                 410                 415

Phe Asp Leu Pro Ala His Leu Lys Ser Cys Leu Leu Cys Leu Ser Ile
            420                 425                 430

Phe Pro Glu Asp Ser Val Ile Lys Lys Lys Val Leu Ile Lys Arg Trp
        435                 440                 445

Ile Ala Glu Arg Leu Ile His Thr Glu Ala Gly Tyr Ser Ile Thr Tyr
    450                 455                 460

Glu Phe Gly Glu Arg Cys Phe Asn Glu Leu Val Asn Arg Ser Leu Ile
465                 470                 475                 480

Gln Pro Gly Glu Thr Asn Arg Tyr Gly Met Val Lys Tyr Cys Arg Val
                485                 490                 495

His Asp Thr Ile Leu Asp Phe Ile Ile Ser Lys Ser Ile Glu Glu Asn
            500                 505                 510

Phe Val Thr Leu Val Gly Val Pro Gly Leu Thr Val Gly Thr Gln Ser
        515                 520                 525

Lys Val Arg Arg Leu Ser Leu Gln Ala Ser Lys Gln Lys Glu Leu Ile
    530                 535                 540

Val Pro Lys Gly Leu Val Leu Ser His Val Arg Ser Leu Asp Val Phe
545                 550                 555                 560

Gly Ile Ser Val Lys Ile Pro Ser Met Asp Lys Phe Arg His Leu Arg
                565                 570                 575

Phe Leu Asp Phe Glu Asp Cys Asp Gln Leu Glu Asn His His Leu Glu
            580                 585                 590
```

```
Asn Ile Gly Lys Leu Phe Gln Leu Arg Tyr Leu Ser Leu Leu Arg Ala
        595                 600                 605

Glu Lys Val Ser Lys Leu Pro Glu Gln Ile Gly His Leu Trp Cys Leu
    610                 615                 620

Glu Ile Leu Asp Leu Arg Asp Thr Ser Val Cys Glu Leu Pro Ala Ser
625                 630                 635                 640

Ile Val Asn Leu Lys Arg Leu Val Arg Leu Leu Val Asn Lys Asn Val
                645                 650                 655

Thr Leu Pro Cys Gly Ile Ser Lys Leu Gln Ala Leu Glu Lys Leu Lys
            660                 665                 670

Ile Val Ser Val Tyr Ser Gln Ser Phe Asn Phe Leu Gln Glu Phe Glu
        675                 680                 685

Gln Leu Gln Ser Leu Lys Ala Leu Thr Leu Asp Phe Glu Asp Tyr Ser
    690                 695                 700

Ser Ala Asp Arg Val Asn Ala Glu Arg Glu Ser Lys Lys Asp Ile Ile
705                 710                 715                 720

Val Ala Ser Leu Lys Asn Leu Gly Asn Leu Leu Ser Leu Thr Val Trp
                725                 730                 735

Asp Gly Pro Glu Leu Val Gly Glu Ser Leu Cys Pro Val Pro Leu Ser
            740                 745                 750

Leu Arg Lys Leu Met Ala Trp Tyr Ser Ser Ile Pro His Val Pro Lys
        755                 760                 765

Trp Val Gly Ser Leu Val Asn Leu Gln Glu Leu Cys Leu Glu Leu Val
    770                 775                 780

Gly Ala Gln Lys Asp Phe Tyr Ile Leu Gly Gly Leu Pro Val Leu Arg
785                 790                 795                 800

Tyr Leu Val Leu Arg Ile Val Glu Arg Glu Val Pro Arg Val Ile Val
                805                 810                 815

Ser Gly Glu Val Gly Phe Pro Cys Leu Arg Ile Phe Lys Tyr Tyr Ile
            820                 825                 830

Trp Tyr Ala Gly Ile His Leu Ser Phe Ala Ala Gly Ala Met Pro Lys
        835                 840                 845

Leu Glu Asp Leu Ser Ile Ile Phe Asp Ala Thr Lys Thr Glu Ser Leu
    850                 855                 860

Gly Thr Ser Gly Ala Phe Asp Leu Gly Ile Glu Asn Leu Pro Ser Leu
865                 870                 875                 880

Val Thr Leu Asp Cys Lys Ala Arg Gly Asp Asp Glu Ser Arg Ala Lys
                885                 890                 895

Ala Ala Lys Ala Ala Leu Arg Glu Ala Ala Asp Ala His Pro Asn His
            900                 905                 910

Pro Ser Leu Lys Phe Ser Glu Val Ser Val Arg Trp Asp Arg Asp Pro
        915                 920                 925

Val Met Leu Glu Arg Arg Tyr
    930                 935


<210> SEQ ID NO 4
<211> LENGTH: 948
<212> TYPE: PRT
<213> ORGANISM: Triticum turgidum subsp. durum

<400> SEQUENCE: 4

Met Glu Ala Ala Leu Val Thr Val Ala Thr Gly Val Leu Lys Pro Val
1               5                   10                  15

Leu Gly Lys Leu Ala Thr Leu Leu Gly Asp Glu Tyr Lys Arg Phe Lys
```

-continued

```
            20                  25                  30

Gly Val Arg Lys Glu Ile Arg Ser Leu Thr His Glu Leu Ala Ala Met
        35                  40                  45

Glu Ala Phe Leu Leu Lys Met Ser Glu Glu Glu Glu Asp Leu Asn Val
    50                  55                  60

Gln Asp Lys Val Trp Met Asn Glu Val Arg Glu Leu Ser Tyr Asp Met
65                  70                  75                  80

Glu Asp Ala Ile Asp Asp Phe Met Gln Ser Val Gly Asp Lys Glu Glu
                85                  90                  95

Lys Pro Asp Gly Phe Ile Asp Lys Ile Lys Ser Ser Leu Gly Lys Leu
            100                 105                 110

Gly Asn Met Lys Ala Arg His Arg Ile Gly Lys Glu Ile Gln Asp Leu
        115                 120                 125

Lys Lys Gln Ile Ile Glu Val Gly Asp Arg Asn Ala Arg Tyr Lys Gly
    130                 135                 140

Arg Glu Ile Phe Ser Lys Ala Val Asn Val Thr Val Asp Pro Arg Ala
145                 150                 155                 160

Leu Ala Ile Phe Glu His Ala Ser Lys Leu Val Gly Ile Asp Glu Pro
                165                 170                 175

Lys Ala Glu Leu Ile Lys Leu Leu Thr Asp Lys Asp Gly Val Ala Ser
            180                 185                 190

Thr Gln Gln Gln Val Lys Met Val Ser Ile Val Gly Ser Gly Gly Met
        195                 200                 205

Gly Lys Thr Thr Leu Ala Asn Gln Val Tyr Gln Glu Leu Lys Glu Lys
    210                 215                 220

Phe Lys Cys Lys Ala Phe Ile Ser Val Ser Arg Asn Pro Asp Met Thr
225                 230                 235                 240

Asn Ile Leu Arg Thr Leu Leu Ser Glu Val Gly Cys Gln Asp Tyr Ala
                245                 250                 255

Asp Thr Glu Ala Gly Ser Ile Gln Gln Leu Ile Arg Lys Ile Thr Asp
            260                 265                 270

Tyr Leu Ala Glu Lys Arg Tyr Ile Ile Val Ile Asp Asp Ile Trp Asp
        275                 280                 285

Val Lys Thr Trp Asp Val Ile Lys Cys Ala Phe Pro Met Thr Arg Cys
    290                 295                 300

Gly Gly Val Ile Ile Thr Thr Thr Arg Leu Ser Asp Val Ala Arg Ser
305                 310                 315                 320

Cys His Ser Ser Ile Gly Gly His Ile Tyr Asn Ile Arg Pro Leu Asn
                325                 330                 335

Met Glu His Ser Arg Gln Leu Phe His Arg Arg Leu Phe Ser Ser Glu
            340                 345                 350

Glu Asp Cys Pro Ser Ser Leu Val Lys Val Ser Asn Gln Ile Leu Glu
        355                 360                 365

Lys Cys Asp Gly Leu Pro Leu Ala Ile Ile Ala Ile Ala Gly Leu Leu
    370                 375                 380

Ala Asn Thr Gly Arg Ser Glu His Leu Trp Asn Gln Val Lys Asp Ser
385                 390                 395                 400

Ile Gly Arg Ala Leu Glu Arg Asn Pro Asn Val Glu Val Met Ile Lys
                405                 410                 415

Ile Leu Ser Leu Ser Tyr Phe Asp Leu Pro Pro His Leu Lys Thr Cys
            420                 425                 430

Leu Leu Tyr Leu Ser Ile Phe Pro Glu Asp Ser Ile Ile Glu Lys Lys
        435                 440                 445
```

```
Thr Leu Ile Ser Arg Trp Ile Ala Glu Gly Phe Ile Gln Lys Glu Gly
    450                 455                 460

Ile Tyr Thr Ala Tyr Glu Val Gly Val Arg Cys Phe Asn Glu Leu Ile
465                 470                 475                 480

Asn Arg Ser Leu Ile Gln Pro Val Lys Lys Asp Asp Tyr Arg Gly Lys
                485                 490                 495

Ser Cys Arg Val His Asp Ile Ile Leu Asp Phe Ile Val Ser Lys Ser
            500                 505                 510

Ile Glu Glu Asn Phe Val Thr Phe Ala Gly Val Pro Ser Leu Thr Thr
        515                 520                 525

Val Thr Gln Gly Lys Val Arg Arg Leu Ser Met Gln Val Glu Gly Lys
    530                 535                 540

Gly Asp Ser Ile Leu Pro Met Ser Pro Ile Leu Ser His Val Arg Ser
545                 550                 555                 560

Phe Asn Val Phe Arg Asn Arg Val Asn Ile His Ser Thr Met Glu Phe
                565                 570                 575

Arg His Leu Arg Val Val Asp Phe Asn Asp Ser Leu Leu Glu Asn His
            580                 585                 590

His Leu Ala Asn Val Gly Arg Leu Leu Gln Leu Arg Tyr Leu Ser Ile
        595                 600                 605

Tyr Met Thr Ala Val Ser Glu Leu Pro Glu Gln Ile Gly His Leu Gln
    610                 615                 620

Cys Leu Glu Met Leu Asp Ile Arg Tyr Thr Met Val Ser Glu Leu Pro
625                 630                 635                 640

Ala Ser Ile Val Asn Leu Gly Lys Leu Ala His Leu Leu Leu Gly Ser
                645                 650                 655

Glu Asp Thr Cys Val Lys Phe Pro Asp Gly Ile Ala Lys Met Gln Ala
            660                 665                 670

Leu Glu Thr Leu Asp Glu Val Asp Ala Ser Lys Gln Ser Tyr Asn Phe
        675                 680                 685

Leu Gln Gly Leu Gly Arg Leu Lys Asn Leu Arg Lys Leu His Ile Asp
    690                 695                 700

Tyr His Asp Val Ala Gln Glu Asp Lys Glu Val Ile Ala Ser Ser Leu
705                 710                 715                 720

Gly Lys Leu Cys Thr Gln Asn Leu Cys Ser Leu Thr Met Arg Gly Asn
                725                 730                 735

Asp Asp Asp Asp Phe Leu Leu Asn Thr Trp Cys Thr Ser Pro Pro Leu
            740                 745                 750

Asn Leu Arg Lys Leu Val Ile Trp Gly Cys Ile Phe Pro Lys Val Pro
        755                 760                 765

His Trp Val Gly Ser Leu Val Asn Leu Gln Lys Leu Arg Leu His Val
    770                 775                 780

Gly Lys Glu Ile Arg His Glu Asp Ile Cys Ile Leu Gly Ala Leu Pro
785                 790                 795                 800

Ala Leu Leu Thr Leu Gly Leu Lys Gly Met Gln Lys Gln Pro Ser Cys
                805                 810                 815

Glu Asp Gly Arg Leu Ala Val Ser Gly Glu Ala Gly Phe Arg Cys Leu
            820                 825                 830

Arg Lys Phe Lys Tyr Cys Arg Trp Gly Asp Arg Met Asp Leu Met Phe
        835                 840                 845

Thr Ala Lys Cys Met Pro Lys Leu Glu Lys Leu Lys Ile Ile Phe Tyr
    850                 855                 860
```

```
Arg His Ala Gln Asp Glu Ala Pro Ile Ile Pro Ala Phe Asp Phe Gly
865                 870                 875                 880

Ile Glu Asn Leu Ser Arg Leu Thr Thr Phe Lys Cys His Leu Gly Cys
                885                 890                 895

Arg Pro Met Ala Thr Arg Thr Phe Asp Ala Val Lys Ala Ser Leu Asp
            900                 905                 910

Arg Val Val Arg Ala His Pro Asn His Leu Thr Val Ile Phe Ser Tyr
        915                 920                 925

Pro Leu Arg Thr Ser Asp Met Thr Tyr Thr Phe His Asp Cys Tyr Met
    930                 935                 940

Arg Ser Gln Asp
945


<210> SEQ ID NO 5
<211> LENGTH: 1624
<212> TYPE: PRT
<213> ORGANISM: Triticum monococcum

<400> SEQUENCE: 5

Met Ser Gly Leu Leu Gly Thr Val Val Asp Ala Thr Ile Gly Trp Leu
1               5                   10                  15

Val Gln Ser Ile Leu Asp Ser Phe Phe Thr Gly Arg Met Glu Ala Trp
            20                  25                  30

Thr Arg Glu Ile Gly Leu Ala Glu Asp Val Glu Lys Leu Lys Phe Gln
        35                  40                  45

Met Arg Asp Val Gln Met Val Leu Ala Ala Ala Glu Gly Arg Arg Ile
    50                  55                  60

Asp Asn Met Pro Leu Ala Leu Ser Leu Asp Gly Leu Arg Glu Leu Leu
65                  70                  75                  80

Tyr Asp Ser Glu Asp Val Met Asp Glu Leu Asp Tyr Tyr Arg Leu Glu
                85                  90                  95

Gln Gln Ile Thr Glu Gly Lys Gly Cys Ser Ala Pro Thr Gly Thr Asn
            100                 105                 110

Leu Glu Gly Ser Tyr Val Ser Ser Ser Thr Leu Ser Ser Val Val Lys
        115                 120                 125

Ser Val Cys Ser Ala Thr Ser Gln Ile Thr Asp Trp Ile Ser Arg Gly
    130                 135                 140

Arg Lys Arg Lys Arg Glu Glu Glu Gly Pro Ala His Cys Asn Met Leu
145                 150                 155                 160

Pro Phe Glu Ile Lys Asp Ser Ile Ser Lys Arg Ile Asn Val Ile Val
                165                 170                 175

Asn Leu Leu Cys Ser Ser Ser Asn Ser Val Lys Gly Val Leu Gln Leu
            180                 185                 190

Glu Asn Leu Arg Thr Met Ala Thr Ser Ser Lys Ser Gln Asn Ile Ala
        195                 200                 205

Arg Asp His Arg Met Thr Thr Ser Val Pro Ile Glu Tyr Lys Val Tyr
    210                 215                 220

Gly Arg Asp Ala Glu Arg Asp Glu Ile Ile Asp Leu Leu Ile Lys Gly
225                 230                 235                 240

Gly Ser Ser Asp Leu Asn Val Leu Pro Val Val Gly Ser Gly Gly Ile
                245                 250                 255

Gly Lys Thr Thr Leu Val Arg Tyr Val Tyr His Ala Lys Arg Ile Lys
            260                 265                 270

Asp His Phe Asp Leu Leu Ile Trp Val Cys Val Ser Thr Asn Phe Asp
        275                 280                 285
```

```
Val Val Gly Leu Thr Leu Gln Ile Leu Asp His Val Cys Glu Asp Arg
    290                 295                 300

Pro Tyr Glu Lys Lys Ser Ser Leu Asn Lys Leu Gln Glu Ile Leu Gln
305                 310                 315                 320

Glu Asn Ile Arg Asn Lys Arg Phe Leu Leu Val Met Asp Asp Met Trp
                325                 330                 335

Glu Glu Lys Asp Arg Gly Gly Trp Ile Lys Leu Leu Ala Pro Leu Lys
            340                 345                 350

Ser Asn Lys Val Lys Gly Cys Met Val Leu Ala Thr Thr Arg Thr Lys
        355                 360                 365

Ser Val Ala Lys Met Ile Gly Thr Met Asp Glu Ile Thr Leu Thr Gly
    370                 375                 380

Leu Asp Glu Lys Glu Phe Trp Leu Phe Phe Lys Ala Cys Ala Phe Arg
385                 390                 395                 400

Asn Asp Asn Arg Glu His His Pro Ser Leu Gln Ser Ile Gly Lys Gln
                405                 410                 415

Ile Ala Lys Ala Leu Lys Gly Phe Pro Leu Ala Ala Gln Ser Val Gly
            420                 425                 430

Ala Leu Leu Ser Thr Glu Val Ser Tyr Gln His Trp Thr Thr Val Arg
        435                 440                 445

Asp Lys Trp Lys Ser Leu Gln Gly Tyr Asp Asp Asp Ile Leu Pro Ile
    450                 455                 460

Leu Lys Leu Ser Tyr Asp Tyr Leu Pro Val Tyr Leu Gln Arg Cys Phe
465                 470                 475                 480

Ser Tyr Cys Ser Leu Tyr Pro Glu Asp Tyr Gly Phe Asp Gly Lys Glu
                485                 490                 495

Leu Val His Ala Trp Ile Ser Gln Asn Phe Val Gln Cys Lys Asp Pro
            500                 505                 510

Thr Ile Arg Leu Glu Glu Thr Gly His Glu Tyr Leu Glu Lys Leu Val
        515                 520                 525

Asp Leu Gly Phe Phe Gln Lys Asp Gly Ser His Tyr Val Met His Asp
    530                 535                 540

Leu Met His Ala Leu Ala Gly Met Val Ser Ser Asn Glu Cys Ala Thr
545                 550                 555                 560

Ile Asp Gly Leu Lys Ser Gly Ala Ile Arg Ala Ser Val Arg His Leu
                565                 570                 575

Ser Ile Ile Ile Thr Asp Tyr Asp Lys Asp Glu His Val Ser Asn Ser
            580                 585                 590

Ser Glu Lys Phe Asp Lys Ile Leu Gln Lys Val Ser Trp His Lys Leu
        595                 600                 605

Arg Thr Leu Met Leu Phe Gly Arg Ser Ser Ile His Leu Ser Gly Pro
    610                 615                 620

Leu Arg Thr Leu Cys Asn Val Ala Lys Cys Leu Arg Leu Leu Ser Val
625                 630                 635                 640

Thr Gly Ala Asp Ile Ser Ser Ile Tyr Asn Ser Ser Asn Leu Phe His
                645                 650                 655

Leu Arg Tyr Ile Ser Ala Tyr Arg Val Ser Asn Pro Ala Phe Arg Gln
            660                 665                 670

Ala Leu Thr Arg Cys Tyr His Leu Gln Val Leu Asp Val Gly Ile Ser
        675                 680                 685

Gly Asn Leu Asp Val Pro Thr Asp Met Asn Asn Leu Val Asn Leu Arg
    690                 695                 700
```

```
His Leu Ile Ala His Glu Lys Val His His Ala Ile Asp Cys Val Ser
705                 710                 715                 720

Asn Met Thr Ser Leu Gln Glu Leu Lys Phe Lys Val Gln Asn Val Gly
                725                 730                 735

Ser Phe Glu Ile Gly Gln Leu Gln Ser Met Asn Glu Leu Val Ser Leu
            740                 745                 750

Gly Val Ser Gln Leu Glu Asn Val Lys Thr Lys Glu Glu Ala Trp Ala
        755                 760                 765

Ala Met Leu Thr His Lys Glu Tyr Leu Glu Thr Leu Phe Leu Ser Trp
    770                 775                 780

Glu Asn Ser Ser Met Ser Leu Gln Pro Glu Ala Ala Glu Asp Val Leu
785                 790                 795                 800

Asp Gly Leu Gln Pro His Gln Asn Leu Lys Thr Leu Glu Ile Thr Gly
                805                 810                 815

Tyr Gly Gly Ala Ile Ser Pro Thr Trp Leu Ser Ser Ala Phe Ser Val
            820                 825                 830

Thr Ser Leu Gln Ile Leu His Leu Glu Glu Cys Arg Glu Trp Gln Ile
        835                 840                 845

Leu Ser Thr His Gly Met His Ser Leu Arg Lys Leu Thr Leu Ile Arg
    850                 855                 860

Met Leu Asn Leu Met Glu Leu Ser Val Pro Ser Leu Val Glu Leu Ile
865                 870                 875                 880

Leu Ile Gly Met Pro Lys Leu Lys Lys Cys Thr Gly Ser Tyr Gly Met
                885                 890                 895

Asp Leu Thr Ser His Leu Ser Val Leu Met Ile Lys Asn Cys Pro Gln
            900                 905                 910

Leu Asn Glu Leu Thr Leu Phe Gln Ser Tyr Ser Ser Phe Asp Ala Glu
        915                 920                 925

Gln Lys Ser Trp Phe Pro Ser Leu Ser Lys Leu Ser Ile Gly Gln Cys
    930                 935                 940

Pro His Ile Ile Asn Asn Trp Pro Ile Leu Pro Leu Arg Glu Met Gly
945                 950                 955                 960

Ala Leu Lys Glu Leu Glu Leu Met Asp Leu His Val Val Arg Val Ser
                965                 970                 975

Val Pro Ser Leu Glu Lys Leu Val Leu Thr Lys Met Pro Ile Leu Glu
            980                 985                 990

Tyr Cys Ser Ser Leu Thr Thr Ser  Pro Pro Leu Gln Ser  Ser Pro Pro
        995                 1000                1005

Glu Gly  Asp Gln Asn Glu Leu  Val Ser Asn Leu Arg  Arg Leu Thr
    1010                1015                1020

Ile His  Asp Cys Pro Cys Leu  Ile Val Ser His Pro  Leu Pro Pro
    1025                1030                1035

Ser Ala  Leu Ile Ser Glu Leu  Ser Ile Ser Gly Val  Ser Thr Leu
    1040                1045                1050

Pro Thr  Met Arg Ile Asn Trp  Arg His Phe Thr Ile  Glu Ser Asn
    1055                1060                1065

Glu Leu  Cys Met Leu Asp Glu  Ser Ile Leu Ala Phe  His Asn Leu
    1070                1075                1080

Arg Gly  Ile Thr Leu Phe Gln  Ile Arg Ser Cys Pro  Asn Leu Ile
    1085                1090                1095

Ser Leu  Ser Ser Glu Ser Phe  Ser Gln Leu Ile Ala  Leu Glu Thr
    1100                1105                1110

Leu Ser  Ile His Glu Cys Pro  Asn Leu Thr Met Ser  Asn Ile Met
```

-continued

```
    1115                1120                1125

Pro Glu  Val Val Gln Glu Asn  Ser Thr Ser Thr Ser  Ser Leu Val
    1130                1135                1140

Pro Pro  Ser Leu Lys Arg Val  Asn Ile Ser Thr Cys  Gly Val Thr
    1145                1150                1155

Gly Arg  Trp Leu Ser Gln Leu  Leu Ser His Ser Gln  Ser Leu Glu
    1160                1165                1170

Glu Leu  Leu Leu Thr Gly Cys  Pro Gln Ile Lys Phe  Leu Ser Ile
    1175                1180                1185

Ser Gln  Pro Arg Glu Thr Glu  Gly Thr Ser Ser Leu  Val Ser Ala
    1190                1195                1200

Val Thr  Thr Ser Ala Gln Asp  Glu His Glu Leu Lys  Leu Pro Tyr
    1205                1210                1215

Asn Leu  Leu Cys Ser Leu Lys  Ala Leu Trp Ile Gln  Leu Ser Leu
    1220                1225                1230

Asp Leu  Glu Phe Cys Gly Gly  Tyr Arg Asp Phe Ala  Gly Phe Thr
    1235                1240                1245

Ser Leu  Met Asp Leu Val Leu  Phe Gly Cys Pro Lys  Leu Val Ser
    1250                1255                1260

Ser Leu  Val Gly Glu Thr Lys  Asp Asp Gly Thr Met  Glu Val Gly
    1265                1270                1275

Leu Leu  Pro Pro Ala Leu Glu  Lys Val Thr Ile Ser  Pro Leu Pro
    1280                1285                1290

Glu Ser  Leu Arg Ser Phe Thr  Pro Gln Gly Leu Leu  His Leu Lys
    1295                1300                1305

Glu Leu  Ser Leu Phe Tyr Gly  Pro Cys Leu Lys Ser  Val Gln Leu
    1310                1315                1320

His Ser  Cys Thr Ser Leu Val  Glu Leu Gly Ile Thr  Gly Cys Val
    1325                1330                1335

Gln Leu  Ala Val Leu Glu Gly  Leu Gln Phe Leu Thr  Ser Leu Arg
    1340                1345                1350

Ser Leu  Asp Ile Glu Met Ser  Pro Glu Leu Ser Ser  Ala Trp Asp
    1355                1360                1365

Leu Lys  Leu Gln Glu Gln Glu  Gln Gly Gly Asn Gln  Ile Gln Leu
    1370                1375                1380

Leu Pro  Pro Ser Leu Asp Lys  Leu Glu Ile Arg Ala  Leu Thr Asp
    1385                1390                1395

Ser Val  Gln Ser His Leu Leu  Ser Cys Leu Pro Ala  Ile Thr Lys
    1400                1405                1410

Leu Ala  Ile Gly Arg Ser Pro  Glu Leu Thr Ser Leu  Gln Leu Gly
    1415                1420                1425

Cys Cys  Thr Ala Leu Lys Glu  Leu Glu Ile Glu Lys  Cys Asp Ser
    1430                1435                1440

Leu Glu  Ser Ile Glu Gly Leu  Gln Phe Cys Arg Asn  Leu Lys Ser
    1445                1450                1455

Leu Arg  Val Phe Asn Ser Pro  Gly Leu Ala Ser Phe  Leu Glu Leu
    1460                1465                1470

Val Ser  His Gln Gln Gly Ala  Ser Val Thr Leu Ser  Gly Leu Gln
    1475                1480                1485

Thr Leu  Glu Ala Ser Asp Gly  Ser Val Leu Ser Thr  His Phe Cys
    1490                1495                1500

Lys Gln  Leu Thr Ser Leu Arg  Leu Leu Gln Phe Gly  Ser Glu Ala
    1505                1510                1515
```

```
Ser Glu  Gly Arg Gly Glu Ser  Leu Val Ser Leu Thr  Glu Glu Gln
    1520                 1525                 1530

Glu Gly  Ala Leu Gln Leu Leu  Thr Ser Leu Gln Glu  Leu Gln Phe
    1535                 1540                 1545

Arg Arg  Cys Gln Asn Leu Leu  Ser Leu Pro Ala Asn  Leu Asn Ser
    1550                 1555                 1560

Leu Thr  Ser Leu Glu Thr Leu  Ser Ile Ile His Cys  Lys Ser Ile
    1565                 1570                 1575

Thr Arg  Leu Pro Asp Met Gly  Leu Pro Thr Ser Leu  Arg Tyr Leu
    1580                 1585                 1590

Lys Leu  Phe Tyr Cys Ser Glu  Glu Leu Ala Val Gln  Cys Arg Ile
    1595                 1600                 1605

Val Ala  Thr Glu Lys Leu Arg  Val Arg Ile Asp Arg  Gln Asp Val
    1610                 1615                 1620

Asn


<210> SEQ ID NO 6
<211> LENGTH: 941
<212> TYPE: PRT
<213> ORGANISM: Triticum aestivum

<400> SEQUENCE: 6

Met Ala Glu Val Leu Val Ser Ala Ser Thr Gly Ala Met Gly Ser Leu
1               5                   10                  15

Leu Arg Lys Leu Gly Ala Met Leu Thr Asp Glu Tyr Lys Leu Leu Lys
            20                  25                  30

Asn Val Arg Gly Asp Ile Lys Phe Leu Lys Asp Glu Leu Glu Val Met
        35                  40                  45

Cys Ala Phe Leu Leu Lys Met Ser Asp Val Glu Glu Pro Asp Glu Pro
    50                  55                  60

Thr Lys Leu Arg Val Thr Ala Val Arg Glu Met Ser Tyr Lys Ile Glu
65                  70                  75                  80

Asp Asn Ile Asp Lys Phe Met Val Leu Val Glu Gln Glu His Gly Ser
                85                  90                  95

Ser Cys Ser Glu Ala Ala His Gly Val Ala Lys Leu Met Asp Lys Cys
            100                 105                 110

Lys Asn Leu Leu Pro Asp Ile Lys Ala Arg Arg Arg Ile Ala Lys Glu
        115                 120                 125

Val Lys Asp Ile Lys Lys Glu Ile Lys Asp Val Ser Asp Arg Phe Ser
    130                 135                 140

Arg Tyr Lys Ile Asp Asp Ser Ser Ser Ser Met Pro Ala Lys Asp Lys
145                 150                 155                 160

Val Asp Pro Arg Leu Arg Ala Val Tyr Lys Asp Ala Ala Glu Leu Val
                165                 170                 175

Gly Ile Asp Gly Pro Lys Asp Glu Leu Val Lys Trp Leu Asn Glu Lys
            180                 185                 190

Glu Gly Gln Ser Leu Lys Ser Val Ser Ile Val Gly Tyr Gly Gly Leu
        195                 200                 205

Gly Lys Thr Thr Leu Ala Asn Gln Ile Arg Val Asn Leu Gly Ala Thr
    210                 215                 220

Phe Asp Cys Gly Ala Phe Val Ser Ile Ser Arg Lys Pro Asp Met Lys
225                 230                 235                 240

Ala Ile Leu Arg Ser Ile Leu Ser Gln Ile Thr Lys Lys Asp Asp Ala
                245                 250                 255
```

```
Cys Ser Arg Leu Asp Asp Ile Gln Leu Ile Ile Asp Lys Ile Arg Glu
            260                 265                 270

Phe Leu Gln Asp Thr Arg Tyr Phe Ile Ile Ile Asp Asp Ile Trp Glu
        275                 280                 285

Leu Gly Thr Trp Glu Thr Leu Lys Cys Ala Phe Val Lys Asn Thr Leu
    290                 295                 300

Gly Ser Arg Ile Ile Ile Thr Thr Arg Ile Val Asp Val Ala Lys Ser
305                 310                 315                 320

Cys Ser Pro Ser Ser Glu Asp Leu Val Tyr Glu Met Lys Pro Leu Ser
                325                 330                 335

Glu Ala Asp Ser Lys Lys Leu Phe Phe Lys Arg Ile Phe Gly Cys Glu
            340                 345                 350

Glu Ser Cys Pro Asp Ser Leu Lys Glu Ala Ala Asn Asp Ile Leu Lys
        355                 360                 365

Lys Cys Arg Gly Leu Pro Leu Ala Ile Asn Ala Ile Ser Ser Val Leu
    370                 375                 380

Val Thr Thr Arg Glu Thr Lys Glu Glu Trp Asp Arg Val Arg His Ser
385                 390                 395                 400

Ile Arg Ser Ser Lys Val Lys Ser Asp Ile Ile Glu Thr Met Asn Tyr
                405                 410                 415

Ile Leu Ser Leu Ser Tyr Phe Asp Leu Pro His His Leu Arg Ser Cys
            420                 425                 430

Leu Leu Tyr Leu Ala Leu Phe Pro Glu Asp Gln Leu Ile Gly Arg Lys
        435                 440                 445

Arg Leu Val Arg Arg Trp Ile Ser Glu Gly Phe Ile His Gly Glu Ser
    450                 455                 460

Gly Gln Asp Leu Met Glu Leu Gly Glu Glu Tyr Phe His Gln Leu Val
465                 470                 475                 480

Asn Arg Ser Leu Ile Gln Pro Gly Asn Ile Gly Tyr Asp Gly Lys Ala
                485                 490                 495

Met Tyr Cys Arg Val His Asp Thr Ile Leu Asp Phe Leu Ile Asp Lys
            500                 505                 510

Ser Ser Glu Glu Asn Met Cys Thr Val Leu Lys Lys Gln Cys Lys Pro
        515                 520                 525

Asn Gly Ile Val Arg Arg Leu Ser Leu Met Gly Asn Glu Asp Glu Glu
    530                 535                 540

Ile Val Glu Gln Leu Asp Leu Ser His Ala Arg Ser Ile Thr Ala Phe
545                 550                 555                 560

Gly Asp Ile Lys Leu Leu Pro Ser Leu Gly Arg Ser Lys Cys Leu Arg
                565                 570                 575

Val Leu Asp Leu Gln Asp Cys Asp Gln Leu Glu Asn His His Ile Lys
            580                 585                 590

Asp Ile Glu Arg Leu Tyr Gln Leu Arg Tyr Leu Asp Ile Ser Ser Thr
        595                 600                 605

Gly Ile Thr Glu Leu Pro Arg Gln Ile Gly Glu Leu Leu Tyr Leu Glu
    610                 615                 620

Thr Leu Val Ala Tyr Gly Leu Arg Glu Leu Pro Glu Ser Thr Ser Arg
625                 630                 635                 640

Leu Gln Arg Leu Ala Arg Leu Phe Val Tyr Ser Gly Cys Lys Leu Pro
                645                 650                 655

Gly Gly Leu Gly Asn Leu Ile Asn Leu Gln Glu Leu Asp Cys Val Asp
            660                 665                 670
```

```
Ala Leu His Leu Lys His Val Glu Glu Leu Gly Lys Leu Thr Asn Leu
        675                 680                 685

Arg Lys Leu Ser Ile Lys Leu Asp Thr Gly Gly Ile Glu Gly Asn Lys
    690                 695                 700

Leu Glu Glu Ser Lys Glu Lys Leu Val Ser Ser Leu Cys Lys Leu Asp
705                 710                 715                 720

Glu Cys Gly Leu Leu Ser Leu Ser Ile Asp Tyr Tyr Leu Arg Glu Lys
                725                 730                 735

Asp Gly Glu Glu Pro Phe Leu Pro Ala Leu Gly Cys Ile Gln Glu Val
            740                 745                 750

Phe Val Tyr Gly Gln Asp Ile Ser Arg Ile Ser Arg Trp Leu Ala Ser
        755                 760                 765

Leu Pro Asn Leu His Arg Leu Leu Leu Asp Asp Pro Lys Ile Glu Gln
    770                 775                 780

Gln Asp Ile Glu Met Ile Gly Leu Ile Pro Asn Leu Ile Asp Leu Thr
785                 790                 795                 800

Leu Pro Pro Leu Tyr Lys Thr Asp Asp Ala Gly Arg Leu Ile Ile Arg
                805                 810                 815

Arg Glu Gly Phe Gln Gln Leu Gln Lys Phe Glu Ala Tyr Asn Thr Arg
            820                 825                 830

Met Gly Val Leu Met Phe Glu Pro Gly Ala Met Pro Arg Leu Lys Glu
        835                 840                 845

Leu Lys Leu His Asn Phe Ile Glu Lys Pro Lys Ser Ala Ala Val Asp
    850                 855                 860

Phe Asp Phe Gly Ile Gln Arg Leu Ser Ser Leu Ala Arg Leu Thr Val
865                 870                 875                 880

Ser Leu Ser Cys Gly Gly Trp Thr Val Ala Glu Val Glu Ala Ala Glu
                885                 890                 895

Asp Ala Phe Lys Ser Met Ala Glu Ala Asn Pro Asn Arg Pro Ile Leu
            900                 905                 910

Glu Met Thr Arg Tyr Asn Thr Gln His Met Leu Gln Asp Glu Gln Ile
        915                 920                 925

Gly Met Thr Gly Ser Ala Thr Thr Pro Ala Val Lys Ser
    930                 935                 940


<210> SEQ ID NO 7
<211> LENGTH: 712
<212> TYPE: PRT
<213> ORGANISM: Aegilops tauschii

<400> SEQUENCE: 7

Met Asp Ile Val Thr Gly Ala Ile Ala Lys Leu Ile Pro Lys Leu Gly
1               5                   10                  15

Glu Leu Leu Val Gly Glu Tyr Lys Leu His Lys Gly Val Lys Lys Asn
            20                  25                  30

Ile Glu Asp Leu Leu Lys Glu Leu Lys Thr Met Asn Ala Ala Leu Ile
        35                  40                  45

Lys Ile Gly Glu Val Pro Pro Asp Gln Leu Asp Ser Gln Asp Lys Leu
    50                  55                  60

Trp Ala Asp Glu Val Arg Glu Leu Ser Tyr Val Ile Glu Asp Ala Val
65                  70                  75                  80

Asp Lys Phe Leu Val Arg Val His Gly Val Glu Pro Asp Asp Asn Thr
                85                  90                  95

Asn Gly Phe Lys Gly Leu Met Lys Arg Thr Thr Lys Leu Leu Lys Lys
            100                 105                 110
```

-continued

```
Val Val Asp Lys His Gly Ile Ala His Ala Ile Lys Asp Ile Lys Lys
        115                 120                 125

Glu Leu Gln Glu Val Ala Ala Arg Arg Asp Arg Asn Lys Phe Asp Gly
    130                 135                 140

Ile Ala Ser Ile Pro Thr Glu Ala Ile Asp Pro Arg Leu Arg Ala Leu
145                 150                 155                 160

Tyr Ile Glu Ala Ala Glu Leu Val Gly Ile Tyr Gly Lys Arg Asp Gln
                165                 170                 175

Glu Leu Met Ser Leu Leu Ser Leu Glu Gly Asp Asp Ala Ser Thr Lys
            180                 185                 190

Lys Leu Lys Lys Val Ser Ile Val Gly Phe Gly Gly Leu Gly Lys Thr
        195                 200                 205

Thr Leu Ala Lys Ala Val Tyr Glu Lys Ile Lys Gly Asp Phe Asp Cys
    210                 215                 220

His Ala Phe Val Pro Val Gly Gln Asn Pro Asp Lys Lys Lys Val Phe
225                 230                 235                 240

Arg Asp Ile Leu Met Asp Leu Ser Asn Ser Asn Ser Asp Leu Ala Leu
                245                 250                 255

Leu Asp Glu Arg Gln Leu Ile Asn Lys Leu His Lys Phe Leu Glu Asn
            260                 265                 270

Lys Arg Tyr Leu Val Ile Ile Asp Asp Val Trp Asp Glu Gly Leu Trp
        275                 280                 285

Lys Asp Ile Asn Leu Ala Phe Ser Asn Arg Asn Asn Leu Gly Ser Arg
    290                 295                 300

Leu Ile Ile Thr Thr Arg Ile Phe Gly Val Ser Glu Ser Cys Cys Ser
305                 310                 315                 320

Ser Ala Asp Asp Pro Val Tyr Glu Ile Glu Pro Leu Ser Ile Asp Asp
                325                 330                 335

Ser Ser Lys Leu Phe Tyr Thr Arg Ile Phe Ser Asp Ser Gly Cys Pro
            340                 345                 350

Lys Glu Phe Glu Gln Val Ser Lys Asp Ile Leu Lys Lys Cys Gly Gly
        355                 360                 365

Val Pro Leu Ala Ile Ile Thr Ile Ala Ser Ala Leu Ala Ser Gly Gln
    370                 375                 380

Gln Val Lys Pro Lys His Glu Trp Asp Ile Leu Leu Gln Ser Leu Gly
385                 390                 395                 400

Ser Gly Val Thr Lys Asp Asn Ser Leu Val Glu Met Arg Arg Ile Leu
                405                 410                 415

Ser Phe Ser Tyr Tyr Asn Leu Pro Ser His Leu Lys Thr Cys Leu Leu
            420                 425                 430

Tyr Leu Cys Ile Tyr Pro Glu Asp Ser Met Ile His Arg Asp Arg Leu
        435                 440                 445

Ile Trp Lys Trp Val Ala Glu Gly Phe Val His His Gly Asp Gln Gly
    450                 455                 460

Thr Ser Leu Phe Leu Val Gly Leu Asn Tyr Phe Asn Gln Leu Ile Asn
465                 470                 475                 480

Arg Ser Met Leu Gln Pro Ile Tyr Ser Asp Met Gly Asn Val Tyr Ala
                485                 490                 495

Cys Arg Val His Asp Met Val Leu Asp Leu Ile Cys Asn Leu Ser His
            500                 505                 510

Glu Ala Lys Phe Val Asn Val Phe Asp Gly Thr Gly Asn Ile Met Ser
        515                 520                 525
```

Ser Gln Ser Asn Val Arg Arg Leu Ser Leu Gln Asn Lys Asn Glu Asp
    530                 535                 540

His Gln Ala Lys Pro Leu Thr Asn Ile Met Ser Ile Ser Gln Val Arg
545                 550                 555                 560

Ser Ile Thr Ile Phe Pro Pro Ala Val Ser Ile Met Pro Ala Leu Ser
                565                 570                 575

Arg Phe Glu Val Leu Arg Val Leu Asp Leu Ser Asp Cys Asn Leu Gly
            580                 585                 590

Glu Ser Ser Ser Leu Gln Pro Asn Leu Lys Gly Val Gly His Leu Ile
        595                 600                 605

His Leu Arg Tyr Leu Gly Leu Ser Gly Thr Arg Ile Ser Lys Leu Pro
    610                 615                 620

Ala Glu Ile Gly Thr Leu Gln Phe Leu Glu Val Leu Asp Leu Gly Tyr
625                 630                 635                 640

Asn His Glu Leu Asp Glu Leu Pro Ser Thr Leu Phe Lys Leu Arg Arg
                645                 650                 655

Leu Ile Tyr Leu Asn Val Ser Pro Tyr Glu Val Val Pro Thr Pro Gly
            660                 665                 670

Val Leu Gln Asn Met Thr Ser Ile Glu Val Leu Arg Gly Ile Phe Val
        675                 680                 685

Ser Glu His Tyr Cys Thr Arg Ala Trp Gln Thr Gly Lys Ala Glu Gly
    690                 695                 700

Ala Ser Asp Leu Leu Gln Gly Trp
705                 710

<210> SEQ ID NO 8
<211> LENGTH: 919
<212> TYPE: PRT
<213> ORGANISM: Triticum monococcum subsp. monococcum

<400> SEQUENCE: 8

Met Glu Ile Ala Met Gly Ala Ile Gly Ser Leu Leu Pro Lys Leu Gly
1               5                   10                  15

Glu Leu Leu Ile Gly Glu Ile Thr Leu Glu Lys Lys Val Arg Lys Gly
            20                  25                  30

Ile Glu Ser Leu Ile Thr Glu Leu Lys Leu Met Gln Ala Val Leu Ser
        35                  40                  45

Lys Val Ser Lys Val Pro Ala Asp Gln Leu Asp Glu Gly Val Lys Ile
    50                  55                  60

Trp Ala Gly Asn Val Lys Glu Leu Ser Tyr Gln Met Glu Asp Ile Val
65                  70                  75                  80

Asp Ala Phe Met Val Arg Val Gly Asp Gly Gly Glu Ser Thr Asn Pro
                85                  90                  95

Lys Asn Arg Val Lys Lys Ile Leu Lys Lys Val Lys Lys Leu Phe Lys
            100                 105                 110

Asn Gly Lys Asp Leu His Arg Ile Ser Ala Ala Leu Glu Glu Val Val
        115                 120                 125

Leu Gln Ala Lys Gln Leu Ala Glu Leu Arg Gln Arg Tyr Glu Gln Glu
    130                 135                 140

Met Arg Asp Thr Ser Ala Asn Thr Ser Val Asp Pro Arg Met Met Ala
145                 150                 155                 160

Leu Tyr Thr Asp Val Thr Glu Leu Val Gly Ile Glu Glu Thr Arg Asp
                165                 170                 175

Lys Leu Ile Asn Met Leu Thr Glu Gly Asp Asp Trp Ser Lys His Pro
            180                 185                 190

```
Leu Lys Thr Ile Ser Ile Val Gly Phe Gly Gly Leu Gly Lys Thr Thr
        195                 200                 205

Leu Ala Lys Ala Ala Tyr Asp Lys Ile Lys Val Gln Phe Asp Cys Gly
    210                 215                 220

Ala Phe Val Ser Val Ser Arg Asn Pro Glu Met Lys Lys Val Leu Lys
225                 230                 235                 240

Asp Ile Leu Tyr Gly Leu Asp Lys Val Lys Tyr Glu Asn Ile His Asn
                245                 250                 255

Ala Ala Arg Asp Glu Lys Tyr Leu Ile Asp Asp Ile Ile Glu Phe Leu
            260                 265                 270

Asn Asp Lys Arg Tyr Leu Ile Val Ile Asp Asp Ile Trp Asn Glu Lys
        275                 280                 285

Ala Trp Glu Leu Ile Lys Cys Ala Phe Ser Lys Lys Ser Pro Gly Ser
    290                 295                 300

Arg Leu Ile Thr Thr Thr Arg Asn Val Ser Val Ser Glu Ala Cys Cys
305                 310                 315                 320

Ser Ser Glu Asp Asp Ile Tyr Arg Met Glu Pro Leu Ser Asn Asp Val
                325                 330                 335

Ser Arg Thr Leu Phe Cys Lys Arg Ile Phe Ser Gln Glu Glu Gly Cys
            340                 345                 350

Pro Gln Glu Leu Leu Lys Val Ser Glu Glu Ile Leu Lys Lys Cys Gly
        355                 360                 365

Gly Val Pro Leu Ala Ile Ile Thr Ile Ala Ser Leu Leu Ala Asn Lys
    370                 375                 380

Gly His Ile Lys Ala Lys Asp Glu Trp Tyr Ala Leu Leu Ser Ser Ile
385                 390                 395                 400

Gly His Gly Leu Thr Lys Asn Arg Ser Leu Glu Gln Met Lys Lys Ile
                405                 410                 415

Leu Leu Phe Ser Tyr Tyr Asp Leu Pro Ser Tyr Leu Lys Pro Cys Leu
            420                 425                 430

Leu Tyr Leu Ser Ile Phe Pro Glu Asp Arg Glu Ile Arg Arg Ala Arg
        435                 440                 445

Leu Ile Trp Arg Trp Ile Ser Glu Gly Phe Val Tyr Ser Glu Lys Gln
    450                 455                 460

Asp Ile Ser Leu Tyr Glu Leu Gly Asp Ser Tyr Phe Asn Glu Leu Val
465                 470                 475                 480

Asn Arg Ser Met Ile Gln Pro Ile Gly Ile Asp Asp Glu Gly Lys Val
                485                 490                 495

Lys Ala Cys Arg Val His Asp Met Val Leu Asp Leu Ile Cys Ser Leu
            500                 505                 510

Ser Ser Glu Glu Asn Phe Val Thr Ile Leu Asp Asp Pro Arg Arg Lys
        515                 520                 525

Met Pro Asn Ser Glu Ser Lys Val Arg Arg Leu Ser Ile Gln Asn Ser
    530                 535                 540

Lys Ile Asp Val Asp Thr Thr Arg Met Glu His Met Arg Ser Val Thr
545                 550                 555                 560

Val Phe Ser Asp Asn Val Val Gly Lys Val Leu Asp Ile Ser Arg Phe
                565                 570                 575

Lys Val Leu Arg Val Leu Asp Leu Glu Gly Cys His Val Ser Asp Val
            580                 585                 590

Gly Tyr Val Gly Asn Leu Leu His Leu Arg Tyr Leu Gly Leu Lys Gly
        595                 600                 605
```

-continued

Thr His Val Lys Asp Leu Pro Met Glu Ile Gly Lys Leu Gln Phe Leu
    610                 615                 620

Leu Thr Leu Asp Leu Arg Gly Thr Lys Ile Glu Val Leu Pro Trp Ser
625                 630                 635                 640

Val Val Gln Leu Arg Arg Leu Met Cys Leu Tyr Val Asp Tyr Gly Met
                645                 650                 655

Lys Leu Pro Ser Gly Ile Gly Asn Leu Thr Phe Leu Glu Val Leu Asp
            660                 665                 670

Asp Leu Gly Leu Ser Asp Val Asp Leu Asp Phe Val Lys Glu Leu Gly
        675                 680                 685

Arg Leu Thr Lys Leu Arg Val Leu Arg Leu Asp Phe His Gly Phe Asp
    690                 695                 700

Gln Ser Met Gly Lys Ala Leu Glu Glu Ser Ile Ser Asn Met Tyr Lys
705                 710                 715                 720

Leu Asp Ser Leu Asp Val Phe Val Asn Arg Gly Leu Ile Asn Cys Leu
                725                 730                 735

Ser Glu His Trp Val Pro Pro Pro Arg Leu Cys Arg Leu Ala Phe Pro
            740                 745                 750

Ser Lys Arg Ser Trp Phe Lys Thr Leu Pro Ser Trp Ile Asn Pro Ser
        755                 760                 765

Ser Leu Pro Leu Leu Ser Tyr Leu Asp Ile Thr Leu Phe Glu Val Arg
    770                 775                 780

Ser Glu Asp Ile Gln Leu Leu Gly Thr Leu Pro Ala Leu Val Tyr Leu
785                 790                 795                 800

Glu Ile Trp Asn Tyr Ser Val Phe Glu Glu Ala His Glu Val Glu Ala
                805                 810                 815

Pro Val Leu Ser Ser Gly Ala Ala Leu Phe Pro Cys Ala Thr Glu Cys
            820                 825                 830

Arg Phe Ile Gly Ile Gly Ala Val Pro Ser Met Phe Pro Gln Gly Ala
        835                 840                 845

Ala Pro Arg Leu Lys Arg Leu Trp Phe Thr Phe Pro Ala Lys Trp Ile
    850                 855                 860

Ser Ser Glu Asn Ile Gly Leu Gly Met Arg His Leu Pro Ser Leu Gln
865                 870                 875                 880

Arg Val Val Val Asp Val Ile Ser Glu Gly Ala Ser Arg Glu Glu Ala
                885                 890                 895

Asp Glu Ala Glu Ala Ala Leu Arg Ala Ala Ala Glu Asp His Pro Asn
            900                 905                 910

Arg Pro Ile Leu Asp Ile Trp
        915

<210> SEQ ID NO 9
<211> LENGTH: 1230
<212> TYPE: PRT
<213> ORGANISM: Triticum aestivum

<400> SEQUENCE: 9

Met Ala Glu Phe Val Val Arg Pro Leu Val Ser Thr Leu Met Asn Thr
1               5                   10                  15

Ala Ser Ser Tyr Leu Leu Asp Gln Tyr Lys Val Met Asp Gly Met Lys
            20                  25                  30

Glu Gln Arg Glu Thr Leu Lys Arg Gln Leu Pro Ala Ile Leu Asp Ile
        35                  40                  45

Ile Gln Asp Ala Glu Lys Lys Gly Ala Ser Leu Pro Gly Val Arg Ala
    50                  55                  60

```
Trp Leu Glu Ala Leu Lys Lys Val Ala Tyr Glu Ala Asn Asp Val Phe
65                  70                  75                  80

Asp Glu Phe Lys Tyr Glu Ala Leu Arg Arg Asp Ala Lys Lys Lys Gly
                85                  90                  95

His Tyr Lys Lys Leu Gly Phe Asp Ile Val Ser Leu Phe Pro Ala His
            100                 105                 110

Asn Pro Ile Val Phe Arg Tyr Arg Met Gly Lys Lys Leu Cys Arg Ile
        115                 120                 125

Val Arg Lys Ile Glu Gly Leu Val Arg Glu Met Asn Asp Phe Gly Phe
    130                 135                 140

Asn Gln Thr Gln Gln Ala Pro Pro Ser Lys Gln Trp Arg Asn Thr Asp
145                 150                 155                 160

Ser Ile Ile Ile Asp Ser Glu Lys Asp Ile Val Ser Arg Ser Arg Asn
                165                 170                 175

Glu Glu Lys Lys Lys Ile Val Asp Ile Leu Ile Asp Gln Ala Gly Asp
            180                 185                 190

Arg Asp Leu Ile Val Leu Pro Ile Val Gly Met Gly Gly Leu Gly Lys
        195                 200                 205

Thr Thr Phe Ala Gln Leu Val Tyr Asn Asp Pro Ile Ile Lys Glu His
    210                 215                 220

Phe Lys Leu Gln Arg Trp Cys Cys Val Ser Asp Asp Phe Asp Val Val
225                 230                 235                 240

Lys Ile Ala Asn Asn Ile Cys Glu Thr Asn Glu Ile His Arg Glu Lys
                245                 250                 255

Ala Leu Gln Asn Leu Gln Lys Glu Val Ser Gly Lys Arg Tyr Leu Ile
            260                 265                 270

Val Leu Asp Asp Val Trp Asn Glu Asp Ala Asp Lys Trp Glu Lys Leu
        275                 280                 285

Lys Thr Cys Leu Lys His Gly Gly Lys Gly Ser Ala Ile Leu Thr Thr
    290                 295                 300

Thr Arg Asn Val Gln Val Ala Arg Ile Met Lys Met Cys Ile Ala Asp
305                 310                 315                 320

Ser His Asn Leu Arg Asn Leu Asp Lys Val Phe Leu Lys Glu Ile Phe
                325                 330                 335

Glu Asn Arg Ala Phe Cys Leu Gln Lys Pro Lys Ala Ala Glu Leu Ser
            340                 345                 350

Asp Val Val Asp Lys Ile Met Asp Arg Cys Gly Gly Ser Pro Leu Ala
        355                 360                 365

Ala Lys Ala Phe Gly Ser Met Leu Ser Asn Lys Thr Ser Met Lys Glu
    370                 375                 380

Trp Thr Asp Ile Leu Ala Arg Ser Asn Thr Cys Asn Glu Gly Thr Lys
385                 390                 395                 400

Thr Phe Leu Val Leu Lys Leu Ser Tyr Asp Asp Leu Pro Ser His Leu
                405                 410                 415

Lys Gln Cys Phe Ala Phe Cys Ala Val Phe Pro Lys Asp Tyr Glu Ile
            420                 425                 430

Gly Val Glu Thr Leu Ile Gln Leu Trp Met Ala His Asp Phe Ile Pro
        435                 440                 445

Leu Lys Glu Gly Asp Asn Leu Glu Lys Val Gly Arg Glu Ile Phe Asp
    450                 455                 460

Glu Leu Thr Trp Arg Ser Phe Phe Gln Asp Val Lys Arg Ile Pro Arg
465                 470                 475                 480
```

```
Arg Glu Trp Trp Gly Glu Leu Arg Pro Arg Thr Ile Cys Lys Ile His
                485                 490                 495

Asp Leu Met His Asp Ile Ala Leu Ser Val Met Gly Lys Asp Cys Leu
            500                 505                 510

Thr Ile Val Asp Arg Pro Asn Glu Lys Glu Leu Leu Ser Thr Gly Pro
        515                 520                 525

Thr Arg Tyr Leu Phe Ser Ser Tyr Glu Tyr Ile Gly Thr Leu Leu Asp
    530                 535                 540

Asp Tyr Leu Lys Lys His Ser Pro Ala Leu Gln Thr Leu Leu Tyr Pro
545                 550                 555                 560

Tyr Pro Tyr Thr Ser Asp Ser Ala Pro His Leu Ser Lys Cys Asn Tyr
                565                 570                 575

Leu Arg Ala Leu Gln Leu Phe Ser Leu Arg Lys Leu Pro Leu Trp Pro
            580                 585                 590

Arg His Leu Gln His Leu Arg Tyr Leu Asp Leu Ser Asn Asn Met Leu
        595                 600                 605

Ile Glu Glu Leu Pro Lys Glu Ile Ser Ile Leu Tyr Asn Leu Gln Thr
    610                 615                 620

Leu Asn Leu Cys Asn Cys Arg Arg Leu Asp Gln Leu Pro Glu Asp Met
625                 630                 635                 640

Lys Tyr Met Glu Asn Leu Arg His Leu Tyr Thr Asn Gly Cys Ser Ser
                645                 650                 655

Leu Lys Cys Met Pro Pro Gly Leu Gly Gln Leu Thr Ser Leu Gln Thr
            660                 665                 670

Leu Thr Tyr Phe Val Val Ser Ser Ser Pro Gly Cys Ser Thr Ile Arg
        675                 680                 685

Glu Leu Gln Asp Leu Asn Leu Gly Gly Glu Leu Glu Leu Ser Arg Leu
    690                 695                 700

Gln Phe Ala Thr Glu Val Asp Ala Lys Ala Cys Ser Leu Gly Asn Lys
705                 710                 715                 720

Glu Lys Leu Thr His Leu Ser Leu Lys Trp Gly Asp Asp Ser Ser Asp
                725                 730                 735

Glu Leu Gly His His Arg Asn Val Leu Asp Ala Leu Lys Pro His Ala
            740                 745                 750

Val Leu Glu Phe Leu Arg Ile Arg Ser Tyr Arg Gly Thr Gly Phe Pro
        755                 760                 765

Ala Trp Val Val Ser Ile Asn Phe Leu Gln His Leu Thr Glu Leu Gln
    770                 775                 780

Leu Asp Gly Cys Thr Met Cys Glu Glu Phe Pro Gln Phe Gly Gln Phe
785                 790                 795                 800

Lys Ser Leu Glu Val Leu Val Leu Lys Arg Leu Asn Lys Leu Gln Ser
                805                 810                 815

Leu Cys Asn His Ser Ser Ser Ala Ile Phe Pro Ala Leu Lys Val Leu
            820                 825                 830

Arg Leu Lys Lys Leu Glu Ile Phe Glu Arg Trp Val Ala Thr Glu Gly
        835                 840                 845

Glu Glu Leu Ala Phe Pro Gln Leu Glu Asn Val Lys Ile Lys Asp Cys
    850                 855                 860

Pro Lys Leu Ala Ile Leu Pro Glu Ala Pro Lys Leu Lys Phe Ile Ala
865                 870                 875                 880

Leu Lys Glu Glu Lys Ala Gln Leu Ser Leu Ser Ile Phe Lys Ser Arg
                885                 890                 895

Tyr Met Ala Cys Leu Ser Gly Val Gly Leu Ser Val Arg Asp Thr Glu
```

```
            900                 905                 910

Ala Ala Pro Arg Thr Glu Leu Asp Gln Asp Cys Glu Val Ser Leu Ser
        915                 920                 925

Asn Leu Leu Leu Asp Gly Cys Asn Phe Leu Phe Cys Ser Thr Pro Leu
    930                 935                 940

Gln Pro Thr Val Gly Val Trp Lys Trp Phe Gly Gln Leu Val His Leu
945                 950                 955                 960

Glu Ile Lys Ser Cys Asp Met Leu Ile Tyr Trp Pro Glu Glu Glu Phe
                965                 970                 975

Arg Cys Leu Val Ser Leu Asn Ser Leu Ser Ile Asn Ser Cys Ser Lys
            980                 985                 990

Leu Val Gly His Thr Gln Gly Lys  Gly Cys Arg Thr Arg  Thr Gln Val
        995                 1000                1005

Arg Asp  Gln Leu Leu Pro Asn  Leu Lys Asn Leu Arg  Ile His His
    1010                 1015                 1020

Cys Gly  Ser Leu Thr Glu Leu  Phe Val Leu Pro Pro  Ser Leu Thr
    1025                 1030                 1035

Ser Ile  Asp Met Leu Asp Cys  Asn Ser Ile Glu Ser  Ile Leu Gly
    1040                 1045                 1050

Gln Asp  Asp Thr Glu Leu Glu  Ser Ile Leu His Phe  Asp Thr Ala
    1055                 1060                 1065

Ser Ser  Ser Glu His Phe Asn  Asp Leu Thr Ser Thr  Cys Leu Leu
    1070                 1075                 1080

Glu Gln  Ser Leu Ser Pro Arg  Ile Asn Pro Leu Pro  Cys Leu Asp
    1085                 1090                 1095

Tyr Leu  Arg Ile Val Ser Cys  Lys Lys Leu Arg Phe  Val Pro Val
    1100                 1105                 1110

Gln Leu  Asp Ala Leu Gln Phe  Leu Cys Ile Ser Asp  Cys Asn Gly
    1115                 1120                 1125

Leu Glu  Ser Leu Asp Cys Leu  Gly Asp Leu Pro Ser  Leu Glu Tyr
    1130                 1135                 1140

Leu Tyr  Leu Met Gly Cys Lys  His Leu Ala Ser Val  Pro Gly Ser
    1145                 1150                 1155

Leu Gly  Ser Tyr Ser Ala Leu  Gln Lys Leu Arg Ile  Glu Tyr Cys
    1160                 1165                 1170

Pro Ala  Leu Asn Met Lys Pro  Leu His Gly His Leu  Gln Gln Arg
    1175                 1180                 1185

Leu Asp  Ser Leu Glu Leu Lys  Asp Leu Ser Lys Ala  Gly Ser Ser
    1190                 1195                 1200

His Pro  Asn Glu Gly Pro Lys  Leu Trp Glu Pro Lys  Ser Trp Lys
    1205                 1210                 1215

Tyr Met  Ile Pro Ser Leu Arg  Lys Arg Glu Ser Glu
    1220                 1225                 1230


<210> SEQ ID NO 10
<211> LENGTH: 924
<212> TYPE: PRT
<213> ORGANISM: Aegilops tauschii

<400> SEQUENCE: 10

Met Ala Glu Ile Val Leu Leu Leu Val Ile Glu Lys Ile Gly Val Ala
1               5                   10                  15

Leu Ala Asn Gly Ala Ala His Gln Ala Gly Thr Gln Phe Ser Arg Tyr
            20                  25                  30
```

```
Ala Thr Arg Leu Ile Glu Leu Gln Gly Ser Met Gly Arg Val Val Arg
        35                  40                  45

Glu Leu Arg Ile Ile His Asp Val Leu Cys Gln Met Asp Ile Arg Asn
    50                  55                  60

Arg His Asn Gln Val Tyr Glu Gly Trp Leu Asp Glu Val Arg Lys Val
65                  70                  75                  80

Ala His Gly Met Glu Asp Met Val Asp Glu Tyr Met Tyr Gln Val Gly
                85                  90                  95

Arg Glu His Asp Thr Gly Cys Cys Phe Tyr Leu Lys Lys Gly Leu Arg
            100                 105                 110

Lys Pro Arg Ser Leu Leu Ser Leu Asn Gln Ile Ser Ser Lys Val Lys
        115                 120                 125

Glu Ile Glu Lys Asp Leu Ala His Leu Ser Glu Met Lys Asn Arg Trp
    130                 135                 140

Val Pro Met Ile Asn Asn Glu Asp Thr Ser Ser Leu Asn Tyr Met Ile
145                 150                 155                 160

Lys Lys Ser Gln Asp Leu Ala Asn Ile Ser Arg Ser Leu Asp Asp Glu
                165                 170                 175

Asp Leu Val Gly Val Asp Glu Asn Arg Gly Lys Leu Glu Gln Trp Leu
            180                 185                 190

Gly Ser Asp Asp Val Glu Arg Ser Leu Ile Thr Leu Thr Gly Met Gly
        195                 200                 205

Gly Leu Gly Lys Thr Ala Leu Ala Ser Asn Val Tyr Arg Lys Glu Arg
    210                 215                 220

Glu Lys Phe Gln Cys His Ala Trp Val Ser Ile Ser Gln Thr Tyr Ser
225                 230                 235                 240

Arg Glu Asp Val Leu Arg Asn Ile Ile Lys Glu Leu Phe Lys Asn Lys
                245                 250                 255

Val Ser Gly Pro Ser Asn Ile Ala Ala Met Asp Ile Thr Ser Leu Glu
            260                 265                 270

Glu Thr Leu Lys Arg Tyr Leu Gly Gln Met Lys Tyr Leu Ile Ile Leu
        275                 280                 285

Asp Asp Val Trp Thr Pro Asp Ala Phe Glu Asp Leu Ser Arg Ser Leu
    290                 295                 300

Val Cys Asn Gly Lys Gly Ser Arg Leu Ile Ile Thr Thr Arg Gln Gly
305                 310                 315                 320

Asp Val Ala Ala Leu Ala Ser Gln Gly His Ile Leu Thr Leu Glu Pro
                325                 330                 335

Leu Pro Glu Asp Lys Ala Trp Asp Leu Phe Cys Lys Lys Ser Phe Pro
            340                 345                 350

Lys Glu Thr Asn His His Cys Pro Glu Glu Leu Arg Leu Leu Ser Glu
        355                 360                 365

Glu Ile Leu Ser Lys Cys Lys Gly Leu Pro Leu Ala Ile Val Ser Ile
    370                 375                 380

Gly Ser Leu Leu His Val Arg Glu Lys Thr Val Glu Glu Trp Lys Arg
385                 390                 395                 400

Ile Asn Asp Gln Leu Ser Trp Glu Ile Leu Asn Asn Ser Arg Leu Asp
                405                 410                 415

His Ile Arg Asn Val Leu His Leu Ser Phe Ile Tyr Leu Pro Thr Tyr
            420                 425                 430

Leu Lys Ser Cys Phe Leu Tyr Cys Ser Leu Phe Pro Glu Asp Tyr Leu
        435                 440                 445

Phe His Arg Arg Lys Leu Val Arg Leu Trp Met Ala Glu Gly Phe Ile
```

```
    450                 455                 460

Val Glu Met Gly Ala Ser Thr Leu Glu Glu Val Ala Glu Ser Tyr Val
465                 470                 475                 480

Lys Glu Leu Val Asn Arg Asn Met Leu Gln Leu Val Gly Arg Asn Ser
                485                 490                 495

Phe Gly Arg Met Lys Arg Phe Arg Met His Asp Ile Ile Arg Glu Leu
            500                 505                 510

Ala Leu Asp Leu Cys Gln Lys Asp Arg Phe Gly Val Ile Tyr Glu Glu
        515                 520                 525

Asp Lys Cys Gly Gly Ser Leu Gln Arg Asp Gly Arg Arg Leu Val Val
    530                 535                 540

His Lys Leu Lys Gln Asp Ile Gln Gln Pro Phe Ser Ser Ile His Val
545                 550                 555                 560

Leu Arg Thr Phe Ile Thr Leu Glu Glu Ser Met Ser Ser Phe Pro Leu
                565                 570                 575

Leu Pro Leu Leu Ser Glu Lys Ser Arg Tyr Met Thr Val Leu Glu Leu
            580                 585                 590

Ser Gly Leu Pro Ile Glu Lys Ile Pro Asp Ala Ile Gly Asp Leu Phe
        595                 600                 605

Asn Leu Arg Tyr Leu Gly Leu Arg Tyr Ser Lys Val Lys Leu Leu Pro
    610                 615                 620

Lys Ser Ile Glu Lys Leu Ser Asn Leu Leu Thr Leu Asp Leu Cys Gly
625                 630                 635                 640

Ser Asp Ile His Glu Leu Pro Ala Gly Ile Gly Lys Leu Asn Lys Leu
                645                 650                 655

Arg His Leu Phe Ala Glu Lys Asn Ile Ile Ser Gly Arg Ile Gln Asn
            660                 665                 670

Ile Arg Tyr Ala Arg Gly Val Cys Phe Pro Ile Gly Leu Gly Asn Leu
        675                 680                 685

Thr Asn Leu Gln Thr Leu Gln Ala Leu Glu Val Gln Glu Val Asp Gly
    690                 695                 700

Ser Ile Arg Gln Leu Gly Glu Leu Arg Gln Leu Arg Ser Leu Arg Ile
705                 710                 715                 720

Trp Gly Met Lys Gly Ile Tyr Cys Glu Gln Leu Cys Lys Ser Leu Val
                725                 730                 735

Gln Met Gln Phe Leu Ser Asn Leu Asn Val Asn Ala Ser Asp Glu Asn
            740                 745                 750

Glu Val Leu Ala Leu Asn Ala Leu Pro Ala Asn Leu Gln Lys Leu Ser
        755                 760                 765

Leu Ser Gly Arg Leu Pro Glu Gly Ala Leu Leu Ala Glu Ser Pro Leu
    770                 775                 780

Phe Gln Ala Val Glu Lys Asn Leu Tyr Ser Leu Arg Leu Cys Trp Ser
785                 790                 795                 800

Gln Leu Arg Glu Asp Pro Leu Ser Ser Leu Ser Arg Leu Ala Asn Leu
                805                 810                 815

Thr Asp Leu Leu Leu Asp Arg Ala Tyr Asn Gly Glu Lys Leu Gln Phe
            820                 825                 830

Leu Thr Gly Trp Phe Pro Lys Leu Lys Asn Leu Tyr Leu Trp Asp Met
        835                 840                 845

Pro Asn Leu Lys Arg Leu Glu Ile His Gln Gly Ala Met Thr Ala Leu
    850                 855                 860

Glu Thr Leu Val Leu Gly Asn Leu Glu Ser Met Val Glu Val Pro Pro
865                 870                 875                 880
```

```
Gly Leu Glu Phe Leu Ile Pro Leu Gln Leu Leu Ile Phe Arg Glu Ile
                885                 890                 895

Thr Arg Asp Phe Leu Ala Leu Leu Arg Gln Ser Pro Gln Leu Val Gly
            900                 905                 910

Thr Gln Trp Arg His Ser Leu Arg Asp Asp Asp Gln
        915                 920


<210> SEQ ID NO 11
<211> LENGTH: 956
<212> TYPE: PRT
<213> ORGANISM: Secale cereale

<400> SEQUENCE: 11

Met Asn Ile Val Thr Gly Ala Met Gly Ser Leu Ile Pro Lys Leu Gly
1               5                   10                  15

Glu Leu Leu Met Asp Glu Tyr Lys Leu His Lys Arg Ile Lys Lys Asp
            20                  25                  30

Val Glu Phe Leu Lys Lys Glu Leu Glu Ser Met His Ala Ala Leu Ile
        35                  40                  45

Lys Val Gly Glu Val Pro Arg Asp Gln Leu Asp Arg Gln Val Lys Leu
    50                  55                  60

Trp Ala Asp Glu Val Arg Glu Leu Ser Tyr Asn Met Glu Asp Val Val
65                  70                  75                  80

Asp Lys Phe Leu Val Arg Val Asp Gly Asp Gly Ile Gln Gln Pro His
                85                  90                  95

Asp Asn Ser Gly Arg Phe Lys Glu Leu Lys Asn Lys Met Ile Gly Leu
            100                 105                 110

Phe Lys Lys Gly Arg Asn His His Arg Ile Ala Asp Ala Ile Lys Glu
        115                 120                 125

Ile Lys Glu Gln Leu Gln Glu Val Ala Ala Arg Arg Asp Arg Asn Lys
    130                 135                 140

Val Ala Val Pro Asn Pro Met Glu Pro Ile Thr Ile Asp Pro Cys Leu
145                 150                 155                 160

Arg Ala Leu Tyr Ala Glu Ala Thr Glu Leu Val Gly Ile Tyr Gly Lys
                165                 170                 175

Arg Asp Glu Glu Leu Met Arg Leu Leu Ser Met Glu Gly Asp Asp Ala
            180                 185                 190

Ser Asn Lys Arg Leu Lys Lys Val Ser Ile Val Gly Phe Gly Gly Leu
        195                 200                 205

Gly Lys Thr Thr Leu Ala Arg Ala Val Tyr Asp Lys Ile Lys Gly Asp
    210                 215                 220

Phe Asp Cys Arg Ala Phe Val Pro Val Gly Gln Asn Pro Asp Met Lys
225                 230                 235                 240

Lys Val Leu Arg Asp Ile Leu Ile Asp Leu Gly Asn Pro His Ser Asp
                245                 250                 255

Leu Ala Ile Leu Asp Asp Lys Gln Leu Val Lys Lys Leu His Asp Phe
            260                 265                 270

Leu Glu Asn Lys Arg Tyr Leu Val Ile Ile Asp Asp Ile Trp Asp Glu
        275                 280                 285

Met Leu Trp Glu Gly Ile Asn Phe Ala Phe Ser Asn Arg Asn Asn Leu
    290                 295                 300

Gly Ser Arg Leu Ile Thr Thr Thr Arg Asn Phe Asp Val Ser Lys Ser
305                 310                 315                 320

Cys Cys Leu Ser Ala Asp Asp Ser Ile Tyr Lys Met Lys Pro Leu Ser
```

```
                325                 330                 335

Thr Asp Asp Ser Arg Arg Leu Phe His Lys Arg Ile Phe Pro Asp Ala
            340                 345                 350

Gly Gly Cys Pro Ser Glu Phe Gln Gln Val Ser Glu Asp Ile Leu Lys
        355                 360                 365

Lys Cys Gly Gly Val Pro Leu Ala Ile Ile Thr Ile Ala Ser Ala Leu
    370                 375                 380

Ala Ser Gly Gln His Val Lys Pro Lys His Glu Trp Asp Ile Leu Leu
385                 390                 395                 400

Gln Ser Leu Gly Ser Gly Val Thr Lys Asp Asn Ser Leu Val Glu Met
                405                 410                 415

Arg Arg Ile Leu Ser Phe Ser Tyr Tyr Asn Leu Pro Ser His Leu Lys
            420                 425                 430

Thr Cys Leu Leu Tyr Leu Cys Ile Tyr Pro Glu Asp Ser Thr Ile Gly
        435                 440                 445

Arg Asp Arg Leu Ile Trp Lys Trp Val Ala Glu Gly Phe Val His His
    450                 455                 460

Gly Asp Gln Gly Thr Ser Leu Phe Leu Val Gly Leu Asn Tyr Phe Asn
465                 470                 475                 480

Gln Leu Ile Asn Arg Ser Met Ile Gln Pro Ile Tyr Asp Glu Leu Gly
                485                 490                 495

Gln Val His Ala Cys Arg Val His Asp Met Val Leu Asp Leu Ile Cys
            500                 505                 510

Asn Phe Ser His Glu Ala Lys Phe Val Asn Val Leu Asp Gly Thr Gly
        515                 520                 525

Asn Ser Ile Ser Ser Gln Ser Asn Val Arg Arg Leu Ser Leu Gln Asn
    530                 535                 540

Lys Met Glu Asp His Gln Ala Lys Pro Leu Thr Asn Ile Met Ser Met
545                 550                 555                 560

Ser Arg Val Arg Ser Ile Thr Ile Phe Pro Pro Ala Val Ser Ile Met
                565                 570                 575

Pro Ser Leu Ser Met Phe Glu Val Leu Arg Val Leu Asp Leu Ser Asn
            580                 585                 590

Cys Asp Leu Gly Lys Ser Ser Ser Leu Gln Leu Asn Leu Lys Gly Val
        595                 600                 605

Gly His Leu Ile His Leu Arg Tyr Leu Asp Leu Gln Gly Thr Gln Ile
    610                 615                 620

Ser Glu Leu Pro Thr Glu Ile Gly Asn Leu Gln Phe Leu Glu Val Leu
625                 630                 635                 640

Asp Leu Asp Asn Asn Tyr Glu Leu Asp Glu Leu Pro Ser Thr Leu Phe
                645                 650                 655

Lys Leu Arg Arg Leu Ile Tyr Leu Asn Val Met Leu Tyr Lys Val Val
            660                 665                 670

Pro Thr Pro Gly Val Leu Gln Asn Met Thr Ser Ile Glu Val Leu Arg
        675                 680                 685

Gly Val Leu Val Ser Leu Asn Ile Ile Ala Gln Glu Leu Gly Asn Leu
    690                 695                 700

Thr Arg Leu Arg Glu Leu Lys Ile Cys Phe Lys Asp Gly Asn Leu Asp
705                 710                 715                 720

Ser Tyr Lys Leu Phe Val Lys Ser Leu Gly Asn Leu His His Ile Glu
                725                 730                 735

Ser Leu Ser Ile Ser Tyr Asn Ser Lys Glu Thr Ser Phe Glu Leu Met
            740                 745                 750
```

```
Asp Leu Leu Gly Glu Arg Trp Val Pro Pro Val His Leu Arg Glu Phe
        755                 760                 765

Val Ser Trp Met Pro Ser Gln Leu Ser Ala Leu Arg Gly Trp Ile Lys
    770                 775                 780

Arg Asp Pro Ser His Leu Ser Asn Leu Ser Glu Leu Ile Leu Trp Pro
785                 790                 795                 800

Val Lys Glu Val Gln Gln Glu Asp Val Glu Ile Ile Gly Gly Leu Leu
                805                 810                 815

Ser Leu Arg Arg Leu Trp Ile Lys Ser Thr His Gln Thr Gln Arg Leu
            820                 825                 830

Leu Val Ile Arg Ala Asp Gly Phe Arg Cys Met Met Asp Phe Glu Leu
        835                 840                 845

Asn Cys Gly Ser Ala Ala Gln Ile Met Phe Glu Pro Gly Ala Leu Pro
    850                 855                 860

Arg Ala Glu Val Leu Val Phe Ser Leu Gly Val Arg Val Ala Gln Glu
865                 870                 875                 880

Asp Gly Asn Cys Gly Phe Asp Leu Gly Leu Gln Gly Asn Leu Leu Ser
                885                 890                 895

Leu Arg His Asp Val Phe Val Arg Ile Tyr Cys Gly Gly Ala Arg Val
            900                 905                 910

Gly Glu Ala Lys Glu Ala Glu Ala Ala Val Arg His Ala Leu Glu Ala
        915                 920                 925

His Pro Asn His Pro Pro Ile Asp Ile Glu Met Thr Pro Tyr Ile Ala
    930                 935                 940

Glu Gly Ala Arg Asp Asp Asp Leu Cys Glu Glu Asn
945                 950                 955
```

<210> SEQ ID NO 12
<211> LENGTH: 9
<212> TYPE: PRT
<213> ORGANISM: Artificial Sequence
<220> FEATURE:
<223> OTHER INFORMATION: P-loop consensus
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = Ser or Thr
<220> FEATURE:
<221> NAME/KEY: misc_feature
<222> LOCATION: (8)..(8)
<223> OTHER INFORMATION: Xaa can be any naturally occurring amino acid

<400> SEQUENCE: 12

```
Gly Xaa Xaa Gly Xaa Gly Lys Xaa Thr
1               5
```

<210> SEQ ID NO 13
<211> LENGTH: 9
<212> TYPE: PRT
<213> ORGANISM: Artificial Sequence
<220> FEATURE:

<223> OTHER INFORMATION: Sr61 p-loop

<400> SEQUENCE: 13

Gly Phe Gly Gly Leu Gly Lys Thr Thr
1 5

<210> SEQ ID NO 14
<211> LENGTH: 14
<212> TYPE: PRT
<213> ORGANISM: Artificial Sequence
<220> FEATURE:
<223> OTHER INFORMATION: Sr61 p-loop extended

<400> SEQUENCE: 14

Val Ser Ile Val Gly Phe Gly Gly Leu Gly Lys Thr Thr Leu
1 5 10

<210> SEQ ID NO 15
<211> LENGTH: 4
<212> TYPE: PRT
<213> ORGANISM: Artificial Sequence
<220> FEATURE:
<223> OTHER INFORMATION: kinase 2 motif consensus
<220> FEATURE:
<221> NAME/KEY: MISC_FEATURE
<222> LOCATION: (3)..(3)
<223> OTHER INFORMATION: Xaa = any amino acid

<400> SEQUENCE: 15

Asp Asp Xaa Trp
1

<210> SEQ ID NO 16
<211> LENGTH: 4
<212> TYPE: PRT
<213> ORGANISM: Artificial Sequence
<220> FEATURE:
<223> OTHER INFORMATION: Sr61 kinase 2 motif

<400> SEQUENCE: 16

Asp Asp Leu Trp
1

<210> SEQ ID NO 17
<211> LENGTH: 13
<212> TYPE: PRT
<213> ORGANISM: Artificial Sequence
<220> FEATURE:
<223> OTHER INFORMATION: Sr61 kinase motif 2 extended

<400> SEQUENCE: 17

Arg Tyr Leu Ile Ile Ile Asp Asp Leu Trp Asp Val Ser
1 5 10

<210> SEQ ID NO 18
<211> LENGTH: 9
<212> TYPE: PRT
<213> ORGANISM: Artificial Sequence
<220> FEATURE:
<223> OTHER INFORMATION: kinase 3a motif consensus
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = any amino acid
<220> FEATURE:

<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = any amino acid

<400> SEQUENCE: 18

Gly Xaa Xaa Xaa Xaa Xaa Thr Xaa Arg
1               5

<210> SEQ ID NO 19
<211> LENGTH: 9
<212> TYPE: PRT
<213> ORGANISM: Artificial Sequence
<220> FEATURE:
<223> OTHER INFORMATION: Sr61 kinase 3a motif

<400> SEQUENCE: 19

Gly Ser Arg Val Val Val Thr Thr Arg
1               5

<210> SEQ ID NO 20
<211> LENGTH: 13
<212> TYPE: PRT
<213> ORGANISM: Artificial Sequence
<220> FEATURE:
<223> OTHER INFORMATION: Sr61 kinase 3a motif extended

<400> SEQUENCE: 20

Gly Ser Arg Val Val Val Thr Thr Arg Ile Gln Glu Val
1               5                   10

<210> SEQ ID NO 21
<211> LENGTH: 9
<212> TYPE: PRT
<213> ORGANISM: Artificial Sequence
<220> FEATURE:
<223> OTHER INFORMATION: LRR domain consensus
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = any amino acid
<220> FEATURE:

<221> NAME/KEY: MISC_FEATURE
<222> LOCATION: (9)..(9)
<223> OTHER INFORMATION: Xaa = any amino acid

<400> SEQUENCE: 21

Xaa Xaa Leu Xaa Leu Xaa Xaa Xaa Xaa
1               5

<210> SEQ ID NO 22
<211> LENGTH: 3519
<212> TYPE: DNA
<213> ORGANISM: Thinopyrum ponticum

<400> SEQUENCE: 22
atcaaatata ataaatcata tgtgtattca gttttagttc ccatattatt aatgtaaata 60
ttcatgttcc aaacattcaa atttcgttga aatatattgc agtcaattcc cttgcaacgt 120
gcggggtatc atctagtgtt ttccaatgga ggaacagtag aaatatcttt tggaatgtgt 180
tatgctttct ttctattaaa aaatccttcg attccagcct gctatccaac acaaagtctg 240
gcctatataa tgtgcatatt gcaggtaact cacaagcata actaggaggc caagataaac 300
attctttttc cctcaaaaat agggaaacca agataaatag ttatccagca agagatggtc 360
ggaataatgg tgagcgcttc tactggtgcc atgaactccc tgctgggtaa gttgaccgcc 420
ctcatggggg aggagtttgc taagctgaaa aacatgcgaa aggaggtgca gttcattagg 480
gatgagcttg gcagcatgaa ggatgctcta gagaggcttg cagatgtgga cgagctagat 540
ccacaaacca agagctggag aaacacactg agggagatct cttatgatat cgaggacatc 600
attgatgact tcatgcaaaa cattggggag aaagacaaga actccgggtt tatccataag 660
accattcgac gtctcagaac tttgagatgc cgtcaccgga ttgtgggcca gattcaagag 720
ataaagaaac ttgtccatga gacaagcggt cgtcgcaaaa gatatgcgct tcatactatt 780
atcccaccat cgaacaatga tgttgccatt gacccacgag ttataacact ttatggaatg 840
gcggctaacc ttgttggcat ggaggggtca aagaatgagc ttgttaattg gctagaagac 900
aaggataagc agttgaaggt ggtatcaatt gtgggatttg gaggtctagg taaaacaaca 960
cttgccaatg aggtgtacca tatgctcagg ccaggatcta cctttagtgc atttgtgcca 1020
gtttctcaaa aacctaacat tctaaatctt cttcgtagtt tactatccca acttgggata 1080
gagccaacta tttatgcttg cgtgtcagac cttatcgaca agcttagaga acgtctccaa 1140
actaagaggt acatattctt gcttcatgtc attctgtttg ctgttgtgtt tgatgatcag 1200
atttttatca gagatatcta tgttgtgtat atgcttaatt aattctaaga aaaggaaata 1260
tgttgcatca gtacagactt gggaggaatt catttgagac taataaacaa aaaaaaaaga 1320
taggcatcta ttagttgcat ttaacatacc tctacgagaa aatctgctta gtttcaaact 1380
ttgaattttc tgctaggttt cttatgagca agtaactttt tcctaaacaa aatgtgttaa 1440
ctaattttat ttgtgtatta tgagtttttg ctttaataaa tctagtttat tagcaatcag 1500
tagctgatta atgatctatt ttttctattc aaccacatct aatatttgat taattggtga 1560
atttctgcta ccttggacgt aacattatgc taaatgttgg caggtacttg attataattg 1620
atgatctatg ggatgtatca gcctggaata ttattaaatg tgcactccca gataatgatt 1680
gtggcagcag agtagtagta actacaagaa ttcaagaagt ggctacagca tgttgctccc 1740
atcgccgtga ttacatttta caaatgaagc cccttagcga cgaagattca aaaaggttgt 1800
tttatggcag gatatttggc tccacagaag cttgccctcg gcaccttaga gacgtttcac 1860

-continued ttgaagttct aaaaaaatgt ggtggtttgc ctcttgcaat tactagtata gctagcatgc 1920
ttgccaccga aggtttcgaa caaaaggaaa ggtggaagga tgtacgaaat tctttgggtt 1980
caggaacaaa tggcacgttg aatggggtgc ggcaaatctt aaacctcagc tacaaagatc 2040
ttccttgtta cctaaagaca tgcttcttgt atcttggtat gtatcctgag gactacacca 2100
taaagaggtc tgatctagaa tgccaatgga tggcagaagg ctttgttagt aaagaaaatg 2160
gacatagtgt ggagaaaact gcaagaagtt atttcaacga gcttgtcaat aggagcctta 2220
ttcaacccgt agaatttgac aatacgggat ctgtgacaca atgtagagta catgatatga 2280
tgcttgatct tatcatgctc aagtctgtag aagagaattt tctcacggta gtggatgaca 2340
caaaggacat tacgggattg gattacaagg ctcgtcggct gtctatccgc ttggatggtg 2400
ccagtaatga tctaacaaca ttactgaata acattagtat gtcacatgtt cggtcggtta 2460
tgttctttgg gagctctcag aatacacctc ctctatcaaa gttcaagttc ctccgagttc 2520
tttttattaa cctccatcgt gctacaattg acctcactgg actgtgcaaa ttatatcagt 2580
tgaggtattt atggattagt gacacttgtc attaccaagt accaacacgg attagagagt 2640
tacaacactt ggaaacactg aatgttaaaa gagggctgcc tgatgggatt ggcaacatga 2700
aatccctacg atatctacgt gcatttgatt tacggttgaa caccctagac aatatcaaga 2760
gccttggaga gctgaccaat ctgagatgtt tatttcttga agacagattt tcattaagtt 2820
gtcggaagaa aggcatggat gctctatgct tttccttggg aaggctttgt agcctagaga 2880
ccctgtctgt caatctcagc gaatgcatag atgacttgat gctctgtttt cctccctcaa 2940
ctccctacca ccttgagaga ctccttgtgt catcgaattg ttggttttct aaggtcccta 3000
cctggatggg agaactatgt tacctgcgag agttacaatg tcatcttgat gaatggctaa 3060
atgatggcgt cggtatcctt gcagagctgc ctgccctcac tgacctcgat ttagtaatcc 3120
aaagactacg acacaaaaag attgtcatct acaagaaagc attccctgct ctaaggcgtt 3180
ttgaacttgt attaagcgac ccctcgtacc taaccttccg ggccggtgca atgcccaagc 3240
tccaaaggct gaagctaacg tttgagtgct atgaatgggg gaaccatggg gtcgcaccta 3300
ccggcatcgg gtacttatta gcacttgaag atttgtctgc agttatcatc tgtcaaactg 3360
ctgaagctga tacggaatgg gcagagtctg ccttgaggga cgctattgcc aggcatccaa 3420
ggtgtcctcg tcttcaaata tcaagcggct agtatgtgca aaatttctcc ctcacttcct 3480
ccatcctccc tcccaccatg cttgtttgtt tcgtagagc 3519

<210> SEQ ID NO 23
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 23
tcggaatcgt tcccgtgaat tgaagcta 28

<210> SEQ ID NO 24
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 24
atgctcagga taaggcgtgg atgaatgagg t 31

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 25
ggggagatca aatcgctcac tcat 24

<210> SEQ ID NO 26
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 26
gtacaatttc agttttaact tctcatcctt gag 33

<210> SEQ ID NO 27
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 27
tacagtatga gctgacccag cgg 23

<210> SEQ ID NO 28
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 28
ggatagacaa tgaaaaatga gga 23

<210> SEQ ID NO 29
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 29
gcttttcttg atttaaaatc ataggatgt 29

<210> SEQ ID NO 30
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 30
gatattattg tcgcttccct taaaaac 27

<210> SEQ ID NO 31
<211> LENGTH: 23
<212> TYPE: DNA
<213> ORGANISM: Artificial Sequence
<220> FEATURE:

<223> OTHER INFORMATION: Oligonucleotide primer

<400> SEQUENCE: 31
ttccgagggt catagtctct ggc 23

<210> SEQ ID NO 32
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 32
tctcccacaa aaggccatgt acttctttaa ttcacaag 38

<210> SEQ ID NO 33
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 33
ggaatactcg aataccaggc cat 23

<210> SEQ ID NO 34
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 34
ttgccactgt gaacatgttt atagat 26

<210> SEQ ID NO 35
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 35
gcaggtaact cacaagcata actaggag 28

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 36
gccaatgagg tgtaccatat g 21

<210> SEQ ID NO 37
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 37
atgcactaaa ggtagatcct gg 22

<210> SEQ ID NO 38
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 38
attataatca agtacctgcc aacatt 26

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 39
acaaaaggaa aggtggaagg 20

<210> SEQ ID NO 40
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 40
gacgagcctt gtaatccaa 19

<210> SEQ ID NO 41
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 41
cgatatctac gtgcatttga tttacg 26

<210> SEQ ID NO 42
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 42
aaccaacaat tcgatgacac aagg 24

<210> SEQ ID NO 43
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 43
cagactctgc ccattccgt 19

<210> SEQ ID NO 44
<211> LENGTH: 25
<212> TYPE: DNA
<213> ORGANISM: Artificial Sequence
<220> FEATURE:
<223> OTHER INFORMATION: Oligonucleotide primer -continued

```
<400> SEQUENCE: 44

tgcacatact agccgcttga tattt                                         25


<210> SEQ ID NO 45
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 45

aaccaacaat tcgatgacac aagg                                          24


<210> SEQ ID NO 46
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 46

cgatatctac gtgcatttga tttacg                                        26
```

*PUCCINIA* RESISTANCE GENE

FIELD OF THE INVENTION

The present invention relates to a plant which has integrated into its genome an exogenous polynucleotide encoding a polypeptide which confers resistance to at least one strain of *Puccinia graminis.*

BACKGROUND OF THE INVENTION

Over the past two decades, the emergence of widely virulent Pgt races, like the Ug99 race group (with origins in southern and eastern Africa) (Singh et al., 2015; Li et al., 2019) has motivated global efforts to identify effective rust resistance genes.

During the last seven years, nine seedling (or all stage) Sr genes (viz. Sr13, Sr21, Sr22, Sr33, Sr35, Sr45, Sr46, Sr50 and Sr60) have been cloned, eight of which encode nucleotide-binding, leucine-rich-repeat (NLR) immune receptors (Saintenac et al., 2013: Mago et al., 2015; Zhang et al., 2017; Chen et al., 2018; Periyannan et al., 2013: Steuemagel et al., 2016; Chen et al., 2019 and Arora et al., 2019). Sr60 is the exception and encodes a tandem kinase protein (Chen et al., 2019).

These genes were targeted due to their effectiveness against Ug99 and other Pgt races and their sequences now provide diagnostic tools for marker-assisted breeding and opportunities for potential transgene deployment. However, the subsequent appearance of new, diverse virulent races means that most of these cloned Sr genes have been overcome by at least one Pgt race, including new races both within and outside the Ug99 lineage. For instance, Sr21 has been overcome by many races within the Ug99 lineage (Singh et al., 2015).

No virulence has so far been found for Sr13a, but an allelic variant Sr13b is ineffective against races TTRTF and JRCQC (Olivera et al., 2012). The causal race (TTRTF) of the Sicilian stem rust epidemic in 2016 is virulent on seedlings carrying Sr35 and putatively Sr33 and has an unusually high infection type on adult plants carrying Sr50 (Patpour et al., 2018). Resistance conferred by Sr46 is insufficient to protect crop yield loss (Singh et al., 2015).

The emergence of other stem rust races shows that the threat is not only from the Ug99 lineage, but that single Sr genes are vulnerable to defeat by new Pgt races. Consequently there is an ongoing need to expand resistance genetic resources, and to enhance gene stewardship through codeployment of multiple resistance genes to increase resistance durability.

SUMMARY OF THE INVENTION

The present inventors have identified a new polypeptide and gene which confer some level of resistance to plants against *Puccinia graminis.*

Thus, in a first aspect, the present invention provides a plant comprising an exogenous polynucleotide encoding a polypeptide which confers resistance to at least one strain ofPuccinia *graminis*, wherein the polypeptide comprises amino acids having a sequence as provided in SEQ ID NO:I. a biologically active fragment thereof, or an amino acid sequence which is at least 60% identical to SEQ ID NO:1.

In an embodiment, the polynucleotide is operably linked to a promoter capable of directing expression of the polynucleotide in a cell of the plant.

In another aspect, the present invention provides a transgenic plant which has integrated into its genome an exogenous polynucleotide encoding a polypeptide which confers resistance to at least one strain of *Puccinia graminis*, wherein the polypeptide comprises amino acids having a sequence as provided in SEQ ID NO:1, a biologically active fragment thereof, or an amino acid sequence which is at least 60% identical to SEQ ID NO:1, and wherein the polynucleotide is operably linked to a promoter capable of directing expression of the polynucleotide in a cell of the plant.

In an embodiment, the *Puccinia graminis* is *Puccinia graminis* f. sp. *tritici.*

In an embodiment, the *Puccinia graminis* f sp. *tritici* is a race of Ug99 or DIGALU.

In an embodiment, the strain is one or more or all of race TTRTF, PTKST, TKKTF, TKTTF, TTKTT and TTKTF of *Puccinia graminis* f. sp. *tritici.*

In an embodiment, the transgenic plant has enhanced resistance to at least one strain of *Puccinia graminis* when compared to an isogenic plant lacking the exogenous polynucleotide.

In an embodiment, the polypeptide is an Sr61 polypeptide.

In an embodiment, the polynucleotide comprises nucleotides having a sequence as provided in SEQ ID NO:2, a sequence which is at least 60% identical to SEQ ID NO:2, or a sequence which hybridizes to SEQ ID NO:2. In a further embodiment, i) the polypeptide comprises amino acids having a sequence which is at least 90% identical to SEQ ID NO:1, and/or ii) the polynucleotide comprises a sequence which is at least 90% identical to SEQ ID NO:2.

In an embodiment, the polypeptide comprises one or more, preferably all, of a coiled coil (CC) domain, an nucleotide binding (NB) domain and a leucine rich repeat (LRR) domain.

In a further embodiment, the polypeptide comprises one or more, preferably all, of a p-loop motif, a kinase 2 motif and a kinase3a motif in the NB domain.

In an embodiment, the p-loop motif comprises the sequence GxxGxGK(T/S)T (SEQ ID NO:12), more preferably the sequence GFGGLGKTT (SEQ ID NO:13). In an embodiment, the p-loop motif comprises the sequence VSIVGFGGLGKTTL (SEQ ID NO:14).

In an embodiment, the kinase 2 motif comprises the sequence DDxW (SEQ ID NO:15), more preferably the sequence DDLW (SEQ ID NO:16). In an embodiment, the kinase 2 motif comprises the sequence RYLIIIDDLWDVS (SEQ ID NO:17).

In an embodiment, the kinase 3a motif comprises the sequence GxxxxxTxR (SEQ ID NO:18), more preferably the sequence GSRVVVTTR (SEQ ID NO:19). In an embodiment, the kinase 3a motif comprises the sequence GSRVVVTTRIQEV (SEQ ID NO:20).

In a further embodiment, the LRR domain comprises about 2 to about 10, or about 6, imperfect repeats of the sequence xxLxLxxxx (SEQ ID NO:21).

Preferably, the plant is a cereal plant. Examples of transgenic cereal plants of the invention include, but are not limited to wheat, barley, maize, rice, oats and triticale. In a particularly preferred embodiment, the plant is wheat.

In a further embodiment, the plant comprises one or more further exogenous polvnucleotides encoding another plant pathogen resistance polypeptide. Examples of such other plant pathogen resistance polypeptides include, but are not limited to, Lr34, Lr1, Lr3, Lr2a, Lr3ka, Lr11, Lr13, Lr16, Lr17, Lr18, Lr21, LrB, Lr67, Lr46, Sr50, Sr33, Sr13, Sr26 and Sr35. In an embodiment, the plant further comprises Lr34, Lr67 and Lr46.

Preferably, the plant is homozvgous for the exogenous polynucleotide.

In an embodiment, the plant is growing in a field.

Also provided is a population of at least 1(x) transgenic plants of the invention growing in a field.

In another aspect, the present invention provides a process for identifying a polynucleotide encoding a polypeptide which confers resistance to at least one strain of *Puccinia graminis* comprising:

i) obtaining a polynucleotide operably linked to a promoter, the polynucleotide encoding a polypeptide comprising amino acids having a sequence as provided in SEQ ID NO:1. a biologically active fragment thereof, or an amino acid sequence which is at least 60% identical to SEQ ID NO:1,
ii) introducing the polynucleotide into a plant,
iii) determining whether the level of resistance to *Puccinia graminis* is modified relative to an isogenic plant lacking the polynucleotide, and
iv) optionally, selecting a polynucleotide which when expressed confers resistance to *Puccinia graminis.*

In an embodiment, the polynucleotide comprises nucleotides having a sequence as provided in SEQ ID NO:2, a sequence which is at least 82% identical to SEQ ID NO:2, or a sequence which hybridizes to SEQ ID NO:2.

In another embodiment, the plant is a cereal plant such as a wheat, barley or triticale plant.

In another embodiment, the polypeptide is a plant polypeptide or mutant thereof.

In another embodiment, step ii) further comprises stably integrating the polynucleotide operably linked to a promoter into the genome of the plant.

In an embodiment, the strain is one or more or all of race TTRTF, PTKST, TKKTF, TKTTF, TTKTT and TTKTF of *Puccinia graminis* f. sp. tritici.

Also provided is a substantially purified and/or recombinant polypeptide which confers resistance to at least one strain of *Puccinia graminis*, wherein the polypeptide comprises amino acids having a sequence as provided in SEQ ID NO:1, a biologically active fragment thereof, or an amino acid sequence which is at least 60% identical to SEQ ID NO:1 In an embodiment, the polypeptide is an Sr61 polypeptide.

In an embodiment, the polypeptide comprises amino acids having a sequence which is at least 80% identical, at least 90% identical, or at least 95% identical, to SEQ ID NO:1.

In an embodiment, a polypeptide of the invention is a fusion protein further comprising at least one other polypeptide sequence. The at least one other polypeptide may be, for example, a polypeptide that enhances the stability of a polypeptide of the present invention, or a polypeptide that assists in the purification or detection of the fusion protein.

In a further aspect, the present invention provides an isolated and/or exogenous polynucleotide comprising nucleotides having a sequence as provided in SEQ ID NO:2, a sequence which is at least 60% identical to SEQ ID NO:2, a sequence encoding a polypeptide of the invention, or a sequence which hybridizes to SEQ ID NO:2.

In another aspect, the present invention provides a chimeric vector comprising the polynucleotide of the invention. Preferably, the polynucleotide is operably linked to a promoter.

In an embodiment, the vector further comprises one or more further exogenous polynucleotides encoding another plant pathogen resistance polypeptide as described herein.

In a further aspect, the present invention provides a recombinant cell comprising an exogenous polynucleotide of the invention and/or a vector of the invention.

The cell can be any cell type such as, but not limited to, a plant cell, a bacterial cell, an animal cell or a yeast cell.

Preferably, the cell is a plant cell. More preferably, the plant cell is a cereal plant cell. Even more preferably, the cereal plant cell is a wheat cell.

In a further aspect, the present invention provides a method of producing the polypeptide of the invention, the method comprising expressing in a cell or cell free expression system the polynucleotide of the invention.

Preferably, the method further comprises isolating the polypeptide.

In yet another aspect, the present invention provides a transgenic non-human organism comprising an exogenous polynucleotide of the invention, a vector of the invention and/or a recombinant cell of the invention.

Preferably, the transgenic non-human organism is a plant. Preferably, the plant is a cereal plant. More preferably, the cereal plant is a wheat plant.

In another aspect, the present invention provides a method of producing the cell of the invention, the method comprising the step of introducing the polynucleotide of the invention, or a vector of the invention, into a cell.

Preferably, the cell is a plant cell.

In a further aspect, the present invention provides a method of producing a transgenic plant of the invention, the method comprising the steps of i) introducing a polynucleotide of the invention and/or a vector of the invention into a plant cell,
ii) regenerating a transgenic plant from the cell, and
iii) optionally harvesting seed from the plant, and/or
iv) optionally producing one or more progeny plants from the transgenic plant, thereby producing the transgenic plant.

In an embodiment, the method further comprises screening the plant obtained from step ii) for resistance to a biotrphoc fungus, such as at least one strain of *Puccinia graminis.*

In a further aspect, the present invention provides a method of producing a transgenic plant of the invention, the method comprising the steps of i) crossing two parental plants, wherein at least one plant is a transgenic plant of the invention,
ii) screening one or more progeny plants from the cross for the presence or absence of the polynucleotide, and
iii) selecting a progeny plant which comprise the polynucleotide, thereby producing the plant.

In an embodiment, at least one of the parental plants is a transgenic plant of the invention, and the selected progeny plant comprises an exogenous polynucleotide encoding a polypeptide which confers resistance to at least one strain *Puccinia graminis.*

In a further embodiment, at least one of the parental plants is a tetraploid or hexaploid wheat plant.

In yet another embodiment, step ii) comprises analysing a sample comprising DNA from the plant for the polynucleotide.

In another embodiment, step iii) comprises i) selecting progeny plants which are homozygous for the polynucleotide, and/or ii) analysing the plant or one or more progeny plants thereof for resistance to at least one strain of *Puccinia graminis*.

In an embodiment, the strain is one or more or all of race TTRTF, PTKST, TKKTF, TKTTF, TKTT and TTKTF of *Puccinia graminis* f. sp. *tritici*.

In an embodiment, the method further comprises iii) backcrossing the progeny of the cross of step i) with plants of the same genotype as a first parent plant which lacked a polynucleotide encoding a polypeptide which confers resistance to at least one strain of *Puccinia graminis* for a sufficient number of times to produce a plant with a majority of the genotype of the first parent but comprising the polynucleotide, and iv) selecting a progeny plant which has resistance to the at least one strain of *Puccinia graminis*.

In vet another aspect, a method of the invention further comprises the step of analysing the plant for at least one other genetic marker.

Also provided is a plant produced using a method of the invention.

Also provided is the use of the polynucleotide of the invention, or a vector of the invention, to produce a recombinant cell and/or a transgenic plant. In an embodiment, the transgenic plant has enhanced resistance to at least one strain of *Puccinia graminis* when compared to an isogenic plant lacking the exogenous polynucleotide and/or vector.

In a further aspect, the present invention provides a method for identifying a plant comprising a polynucleotide encoding a polypeptide which confers resistance to at least one strain of *Puccinia graminis*, the method comprising the steps of i) obtaining a nucleic acid sample from a plant, and ii) screening the sample for the presence or absence of the polynucleotide, wherein the polynucleotide encodes a polypeptide of the invention.

In an embodiment, the polynucleotide comprises nucleotides having a sequence as provided in SEQ ID NO:2, a sequence which is at least 60% identical to SEQ ID NO:2, or a sequence which hybridizes to SEQ ID NO:2.

In an embodiment, the step of screening comprises amplifying the polynucleotide. In an embodiment, the amplification is achieved using an oligonucleotide comprising a sequence of nucleotide provided as SEQ ID NO:45 and/or SEQ ID NO:46, or a variant of one or both primers which can be used to amplify the same region of the genome.

In an embodiment, the method identifies a transgenic plant of the invention.

In another embodiment, the method further comprises producing a plant from a seed before step i).

Also provided is a plant part of the plant of the invention.

In an embodiment, the plant part is a seed that comprises an exogenous polynucleotide which encodes a polypeptide which confers resistance to at least one strain of *Puccinia graminis*.

In a further aspect, the present invention provides a method of producing a plant part, the method comprising, a) growing a plant of the invention, and b) harvesting the plant part.

In another aspect, the present invention provides a method of producing flour, wholemeal, starch or other product obtained from seed, the method comprising;

a) obtaining seed of the invention, and b) extracting the flour, wholemeal, starch or other product.

In another aspect, the present invention provides a method of producing flour, the method comprising:

i) obtaining cereal grain, ii) grinding the grain, iii) sifting the ground grain, and iv) recovering the flour, wherein the cereal grain has a genetically modified gene encoding an Sr61 polypeptide.

In a further aspect, the present invention provides a method of producing malt, the method comprising:

i) obtaining cereal grain, ii) steeping the grain, iii) germinating the steeped grains, iv) drying the germinated grain, and v) recovering the malt, wherein the cereal grain has a genetically modified gene an Sr61 polypeptide.

In a further aspect, the present invention provides a product produced from a plant of the invention and/or a plant part of the invention.

In an embodiment, the part is a seed.

In an embodiment, the product is a food product or beverage product. Examples include, but are not limited to, i) the food product being selected from the group consisting of: flour, starch, leavened or unleavened breads, pasta, noodles, animal fodder, animal feed, breakfast cereals, snack foods, cakes, malt, beer, pastries and foods containing flour-based sauces, or ii) the beverage product being beer or malt.

In an alternative embodiment, the product is a non-food product. Examples include, but are not limited to, films, coatings, adhesives, building materials and packaging materials.

In a further aspect, the present invention provides a method of preparing a food product of the invention, the method comprising mixing seed, or flour, wholemeal or starch from the seed, with another food ingredient.

In another aspect, the present invention provides a method of preparing malt, comprising the step of germinating seed of the invention.

Also provided is the use of a plant of the invention, or part thereof, as animal feed, or to produce feed for animal consumption or food for human consumption.

Also provided is the use of a plant of the invention for controlling or limiting *Puccinia graminis* in crop production.

In a further aspect, the present invention provides a composition comprising one or more of a polypeptide of the invention, a polynucleotide of the invention, a vector of the invention, or a recombinant cell of the invention, and one or more acceptable carriers.

In another aspect, the present invention provides a method of identifying a compound that binds to a polypeptide comprising amino acids having a sequence as provided in SEQ ID NO:1, a biologically active fragment thereof, or an amino acid sequence which is at least 60% identical to SEQ ID NO:1, the method comprising:

i) contacting the polypeptide with a candidate compound, and ii) determining whether the compound binds the polypeptide.

Any embodiment herein shall be taken to apply mutatis mutandis to any other embodiment unless specifically stated otherwise.

The present invention is not to be limited in scope by the specific embodiments described herein, which are intended for the purpose of exemplification only.

Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1—Rust phenotypes of Sr26 and Sr61 parental lines and mutants, and gene structures of the Sr26 and Sr6l candidate genes. Lower and upper seedling leaf surfaces of wild-type and representative EMS-derived susceptible mutants for Sr26 and Sr61, together with the recombinant inoculated with Pgt race PTKST. Avocet, Kite, Avocet+ Lr46, W3757, recombinant 376/15 showed low infection types (small pustules or flecking), while Sr26 mutant 12S, Sr61 mutant M4, and susceptible control 37-07 all showed high infection types (large pustules).

Figure 2:
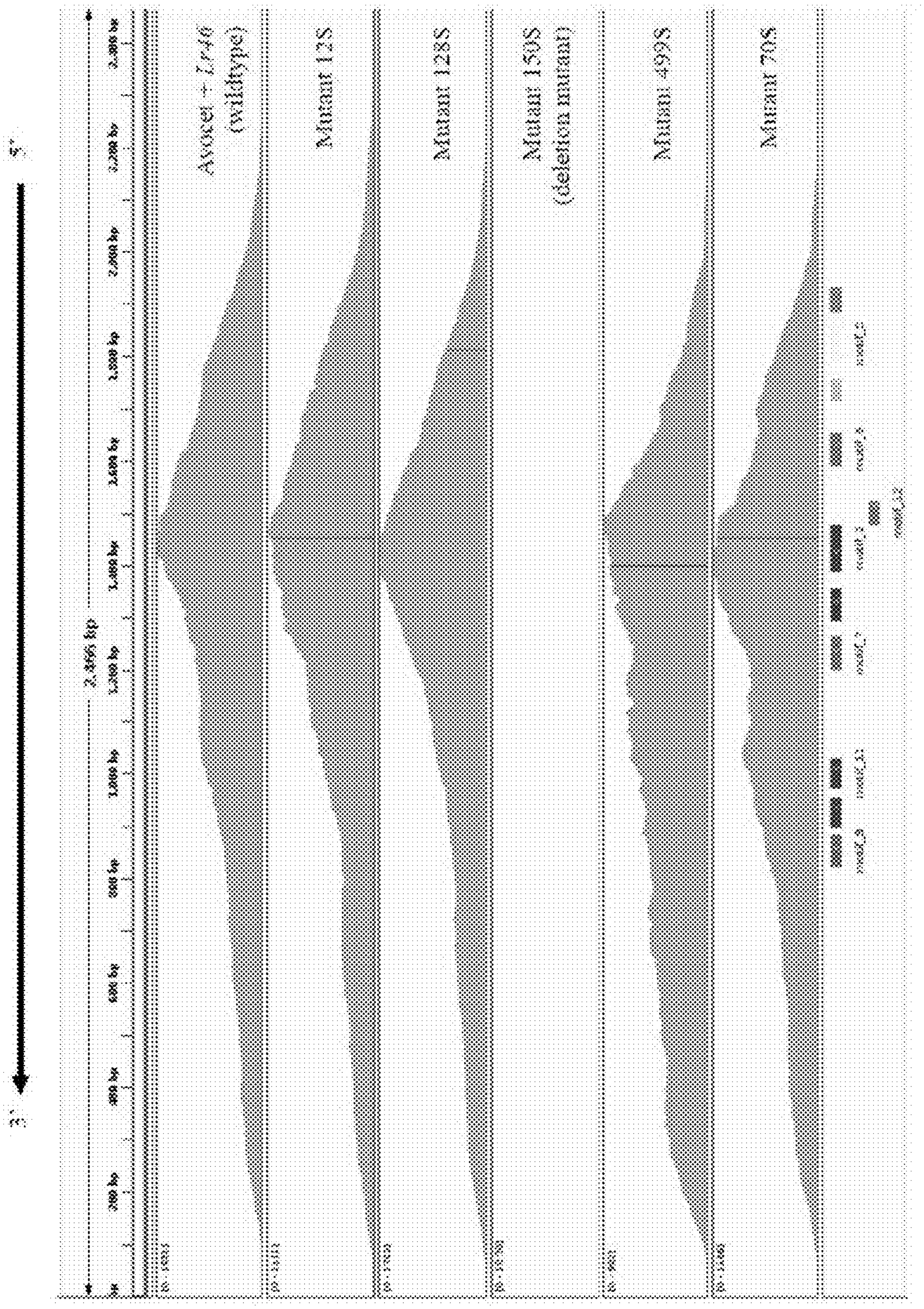

FIG. 2—IGV snapshot indicating SNP changes in each mutant used for identifying the Sr26 candidate gene. The screen capture illustrates the Sr26 locus with four identified susceptible mutants all carrying a mutation in the candidate contig, and one deletion mutant without any reads mapping to the wild-type assembly. The full locus was de novo assembled. From the top to the bottom: Horizontal black lines represent the orientation of the identified contig, read coverages (grey histograms) are indicated on the left, e.g. [0-1651], and the name of line from which the reads were derived are on the right. Vertical bars represent the positions of the SNPs identified between the reads and reference assembly—red shows C to T transitions. Coloured rectangles depict the motifs identified by NLR-Parser (each motif is specific to a conserved NLR domain). Note the orientation of this IGV snapshot view is 3' to 5', therefore all the SNPs have G to A mutation. Mutants 12S and 70S were likely to be siblings due to possessing identical SNPs.

Figure 3:
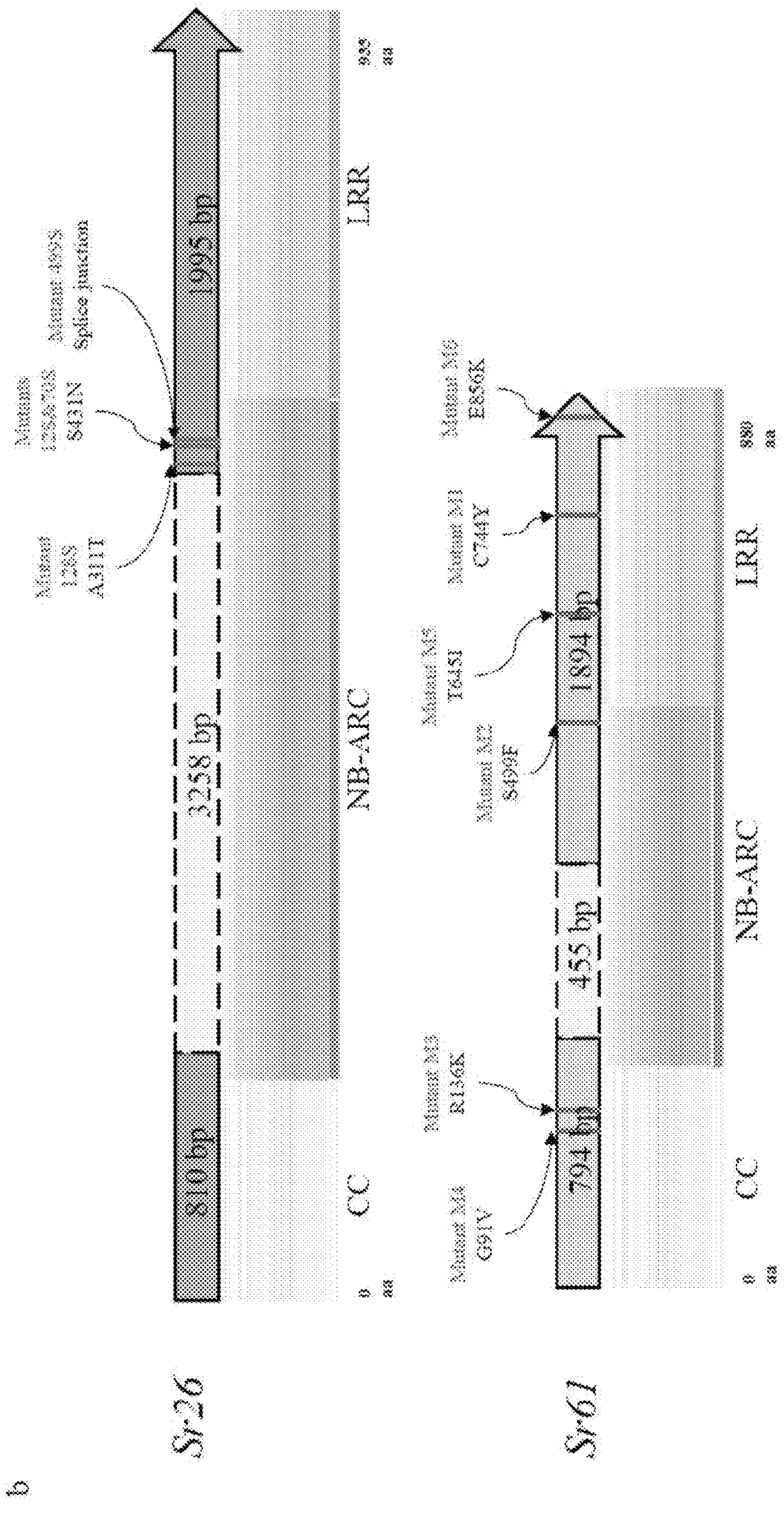

FIG. 3—Candidate gene structures with mutations highlighted, and their predicted locations and effects in the predicted translated Sr26 and Sr6l proteins. Solid blocks represent the exons, while doted blocks represent introns.

Figure 4:
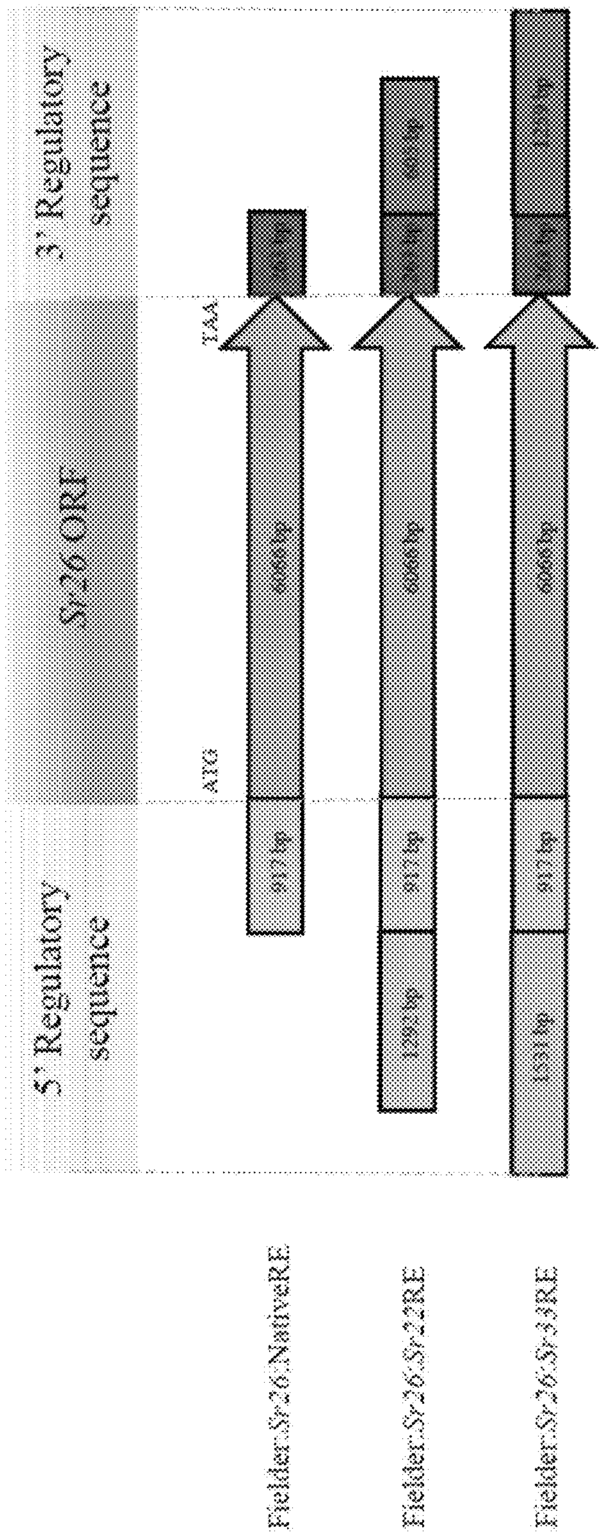
Figure 4:
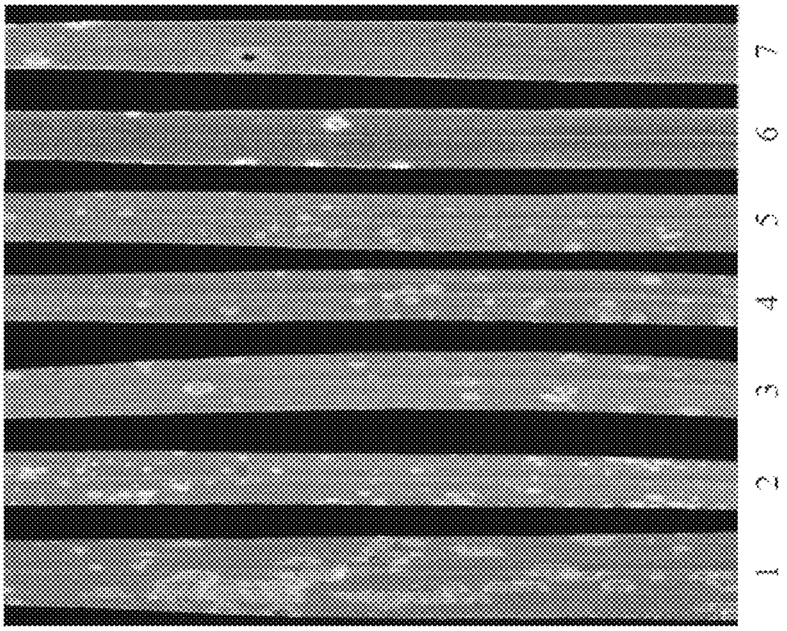

FIG. 4—Validation of the Sr26 candidate gene by transformation. Three constructs used for transformation. (b) Phenotypic responses of representative TO plants derived from all three constructs when inoculated with Pgt race 98-1,2(3)(5),6 along with non-transgenic Fielder lines. Names of the lines: 1. Fielder control; 2. Fielder:Sr26:Sr22RE TO-12; 3. Fielder:Sr26:Sr22RE TO-17; 4. Fielder:Sr26:Sr33RE TO-3; 5. Fielder:Sr26:Sr33RE TO-7; 6. Fielder:Sr26:NativeRE TO-15; 7. Fielder:Sr26:NativeRE TO-6. All lines showed low infection types, except the susceptible Fielder control.

Figure 5:
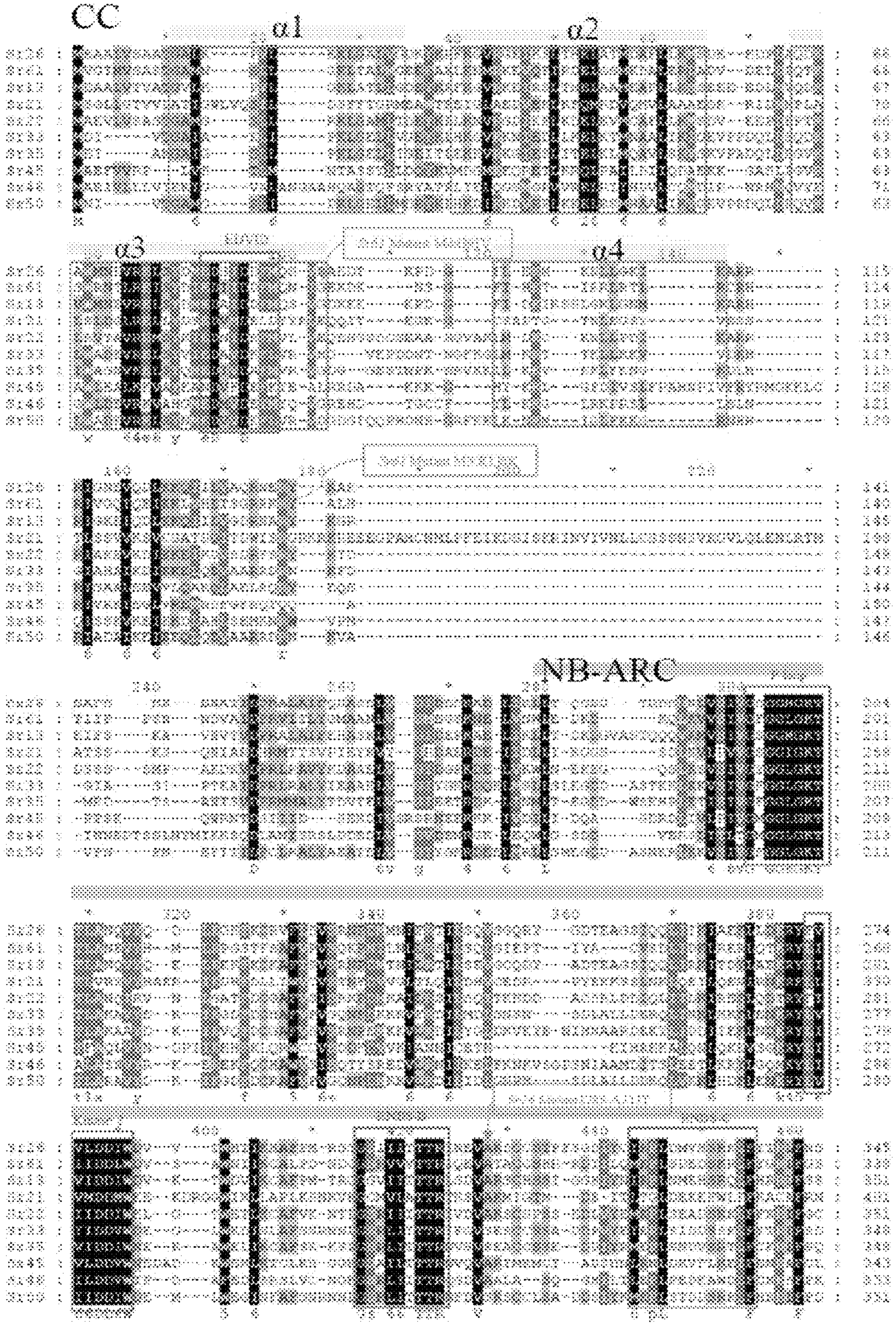
Figure 5:
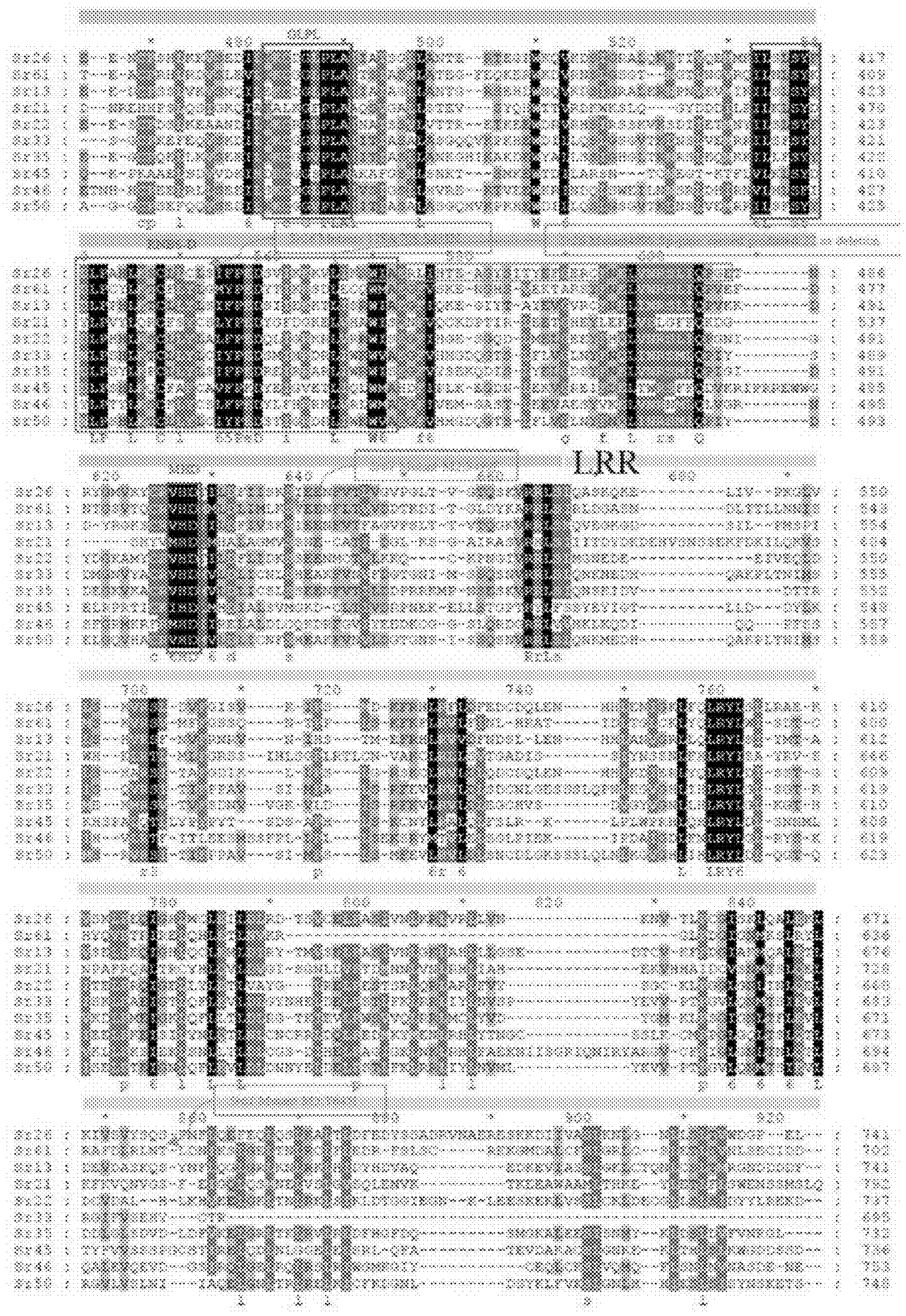
Figure 5:
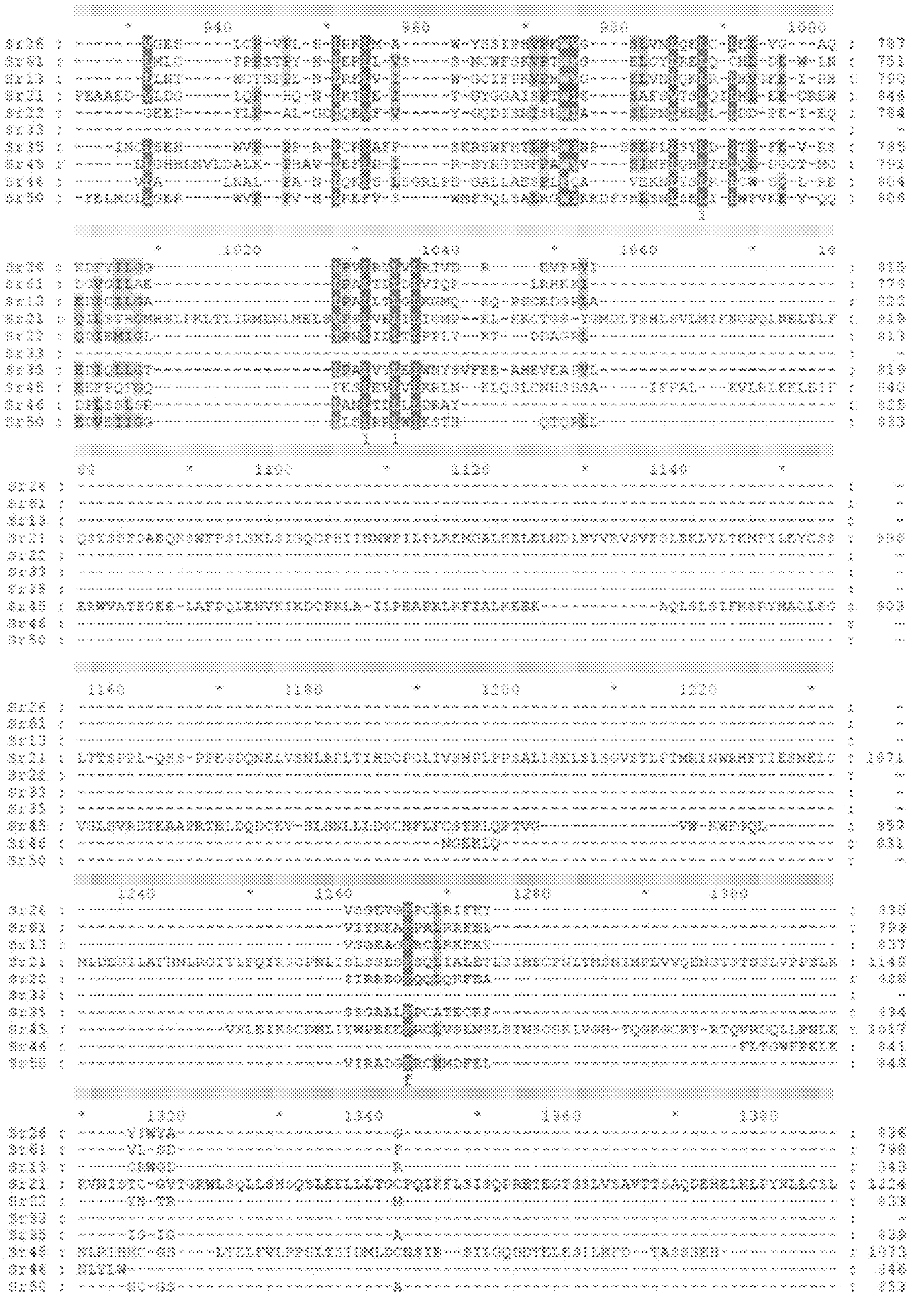
Figure 5:
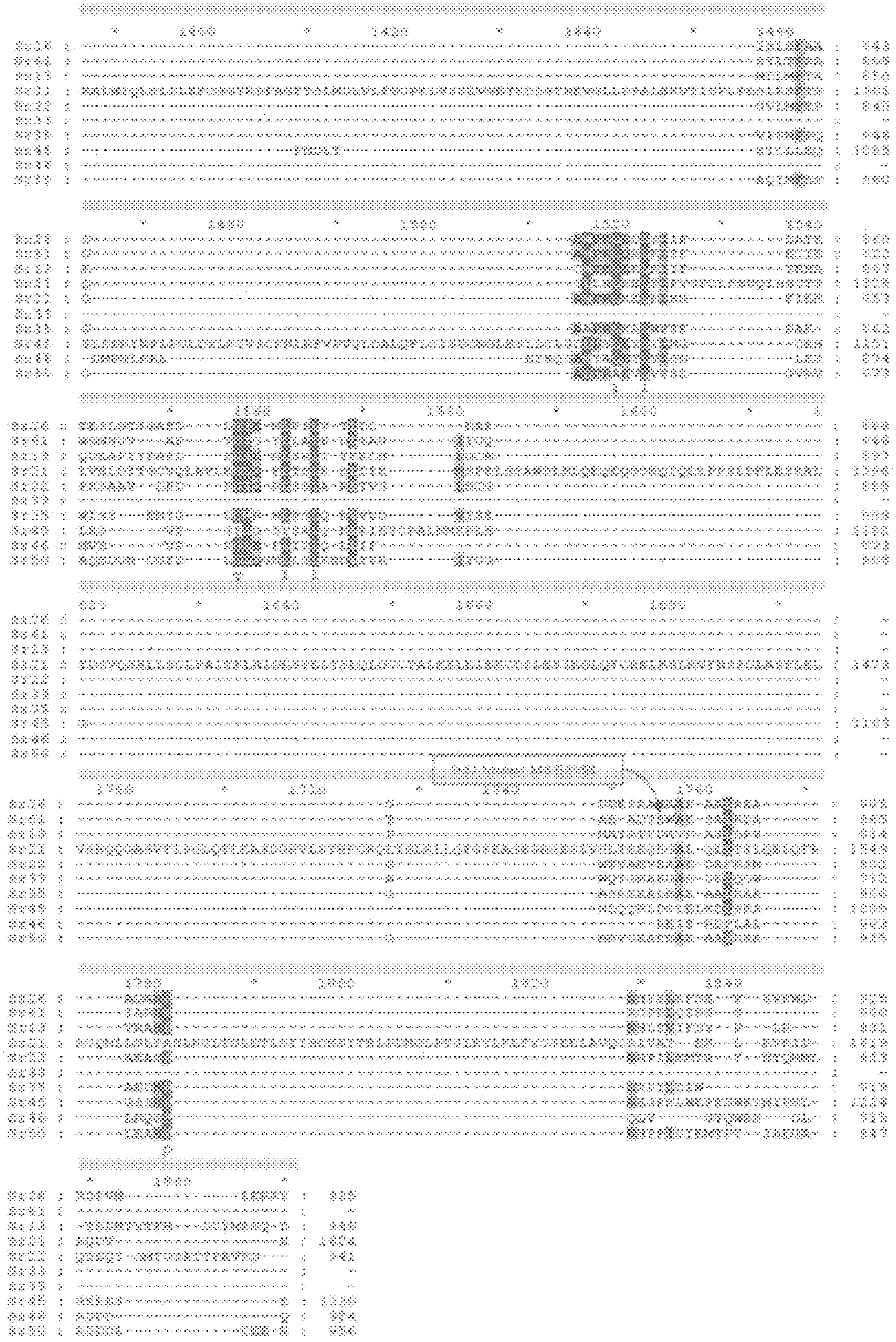

FIG. 5—Amino acid sequence alignment of cloned wheat Sr genes encoded proteins and protein structure modelling of Sr26 (SEQ ID NO: 3), Sr13 (SEQ ID NO: 4), Sr21 (SEQ ID NO: 5), Sr22 (SEQ ID NO: 6), Sr33 (SEQ ID NO: 7), Sr35 (SEQ ID NO: 8), Sr45 (SEQ ID NO: 9), Sr46 (SEQ ID NO: 10), S550 (SEQ ID NO: 11) and Sr61 (SEQ ID NO: 1). The CC (coiled-coil), NB (nucleotide binding)-ARC, and LRR (leucine-rich-repeat) domains are indicated by bars in yellow, peach, and pink, respectively. The conserved motifs (EDVID, P-loop, Kinase 2, RNBS-B, RNBS-C, GLPL, RNBS-D, and MHD) were indicated by red frames and labelled below the sequence alignment. Four α-helixes based on the Sr33 CC domain structure are labelled in purple frames. Sequences in blue frames with pointed arrowheads show the positions of amino acid changes that caused loss-of-function mutations of Sr26 or Sr61.

Figure 6:
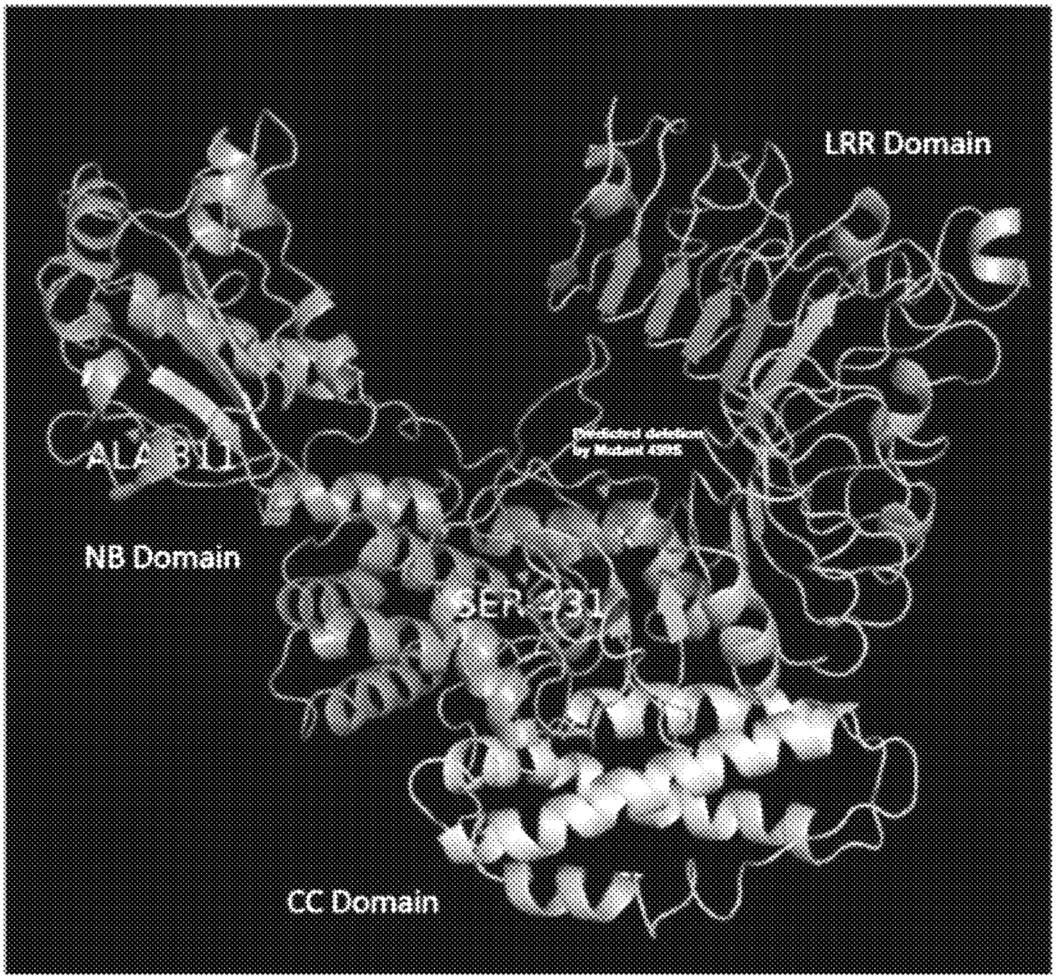

FIG. 6—Positions of all point mutants are indicated, pointed by arrowheads, on the structure modelling of Sr26 based on 6J5V (intermediate state of ZARI-RSK1-PBL2UPM complex). Predicted CC, NB, and LRR domains were shaded in yellow, orange, and cyan, respectively.

Figure 7:
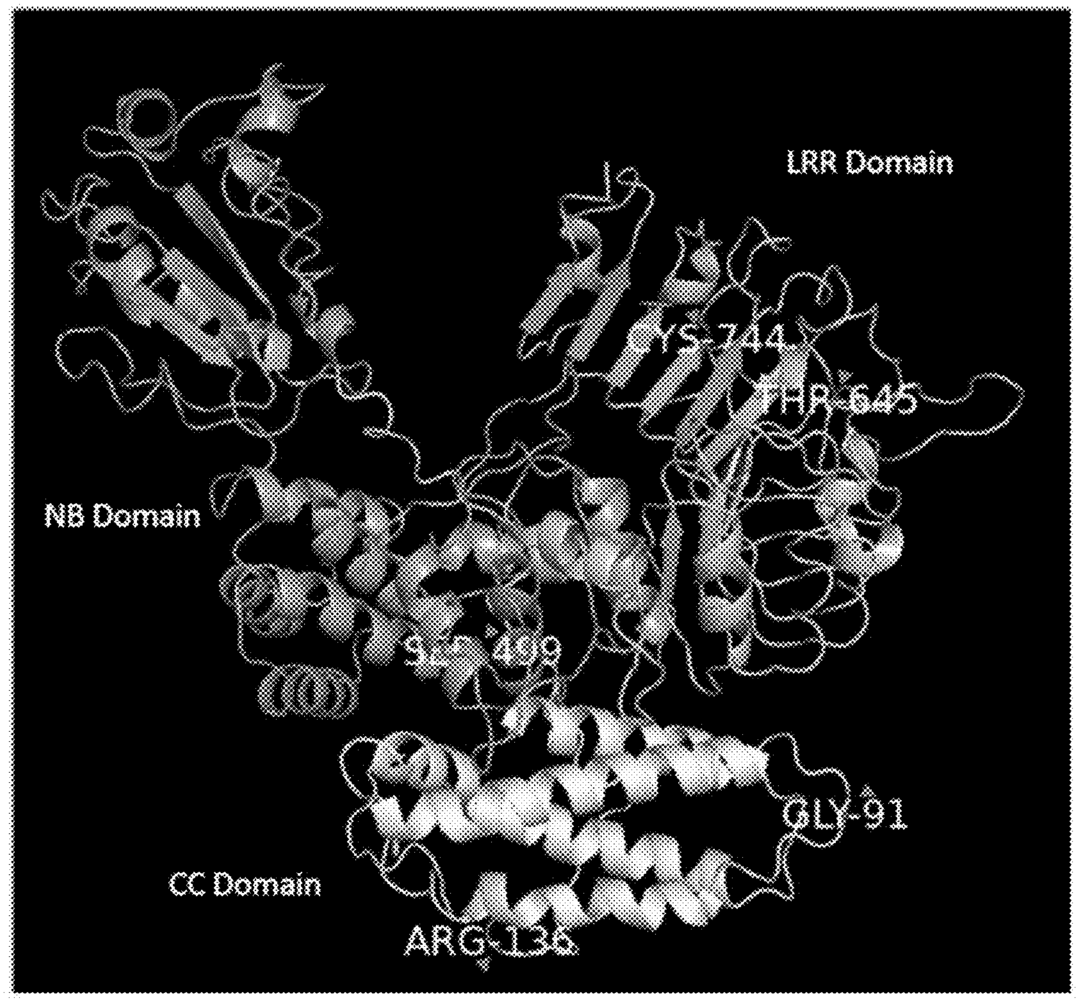

FIG. 7—Positions of all point mutants, except for mutant M6 (E856K), are indicated and pointed by arrows on the structure modelling of Sr61 based on 6J5V (intermediate state of ZAR1-RSK1-PBL2UPM complex). Predicted CC, NB, and LRR domains were shaded in yellow, orange, and cyan, respectively.

Figure 8:
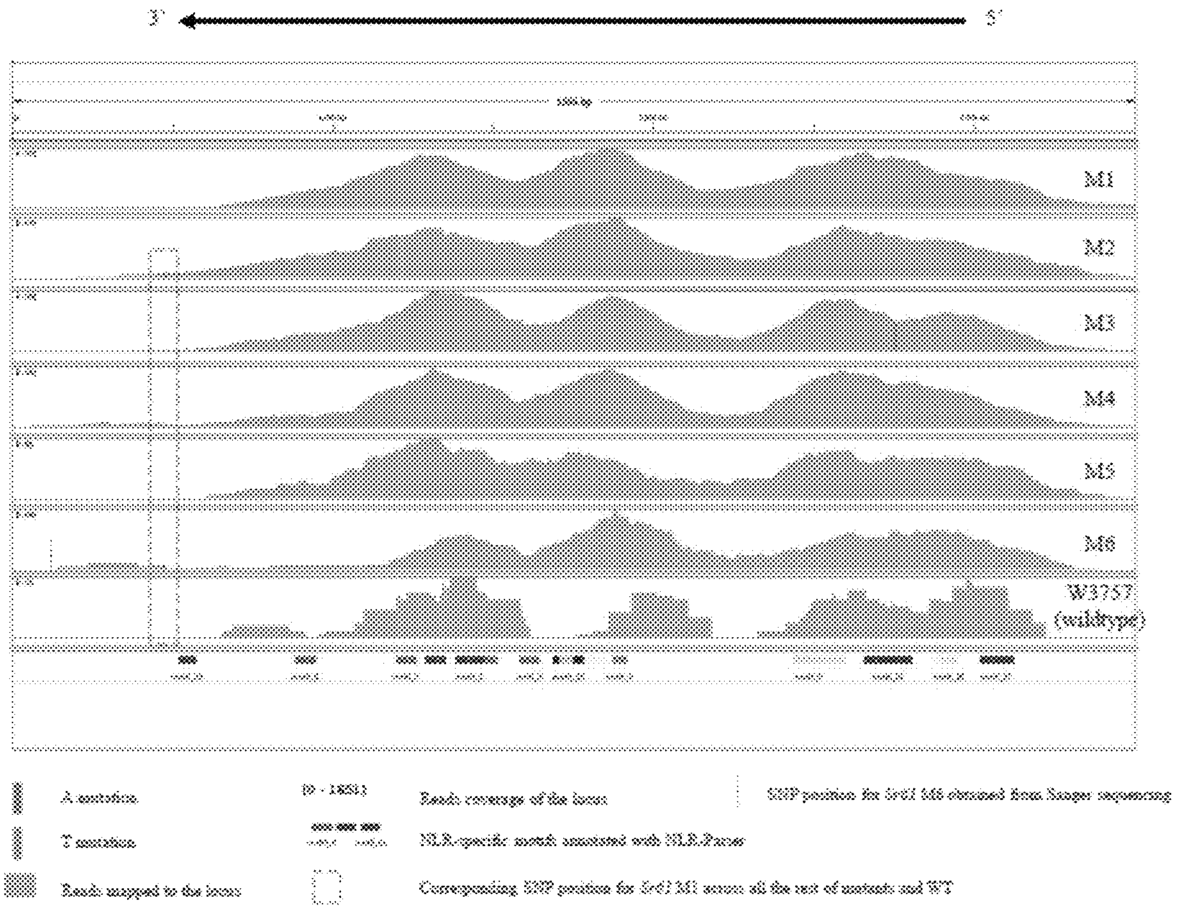

FIG. 8—IGV snapshot indicating SNP changes in each mutant used for identifying the Sr61 candidate gene. The screen capture illustrates the Sr61 locus with five of six identified susceptible mutants carrying a mutation in the candidate contig; the SNP mutant in M6 was identified from the whole gene sequence alignment by Sanger sequencing and the position is indicated in the respective mutant. The complete locus was de novo assembled based on mutant MI, therefore, the SNP for M1 is indicated by dotted frame.

Figure 9:
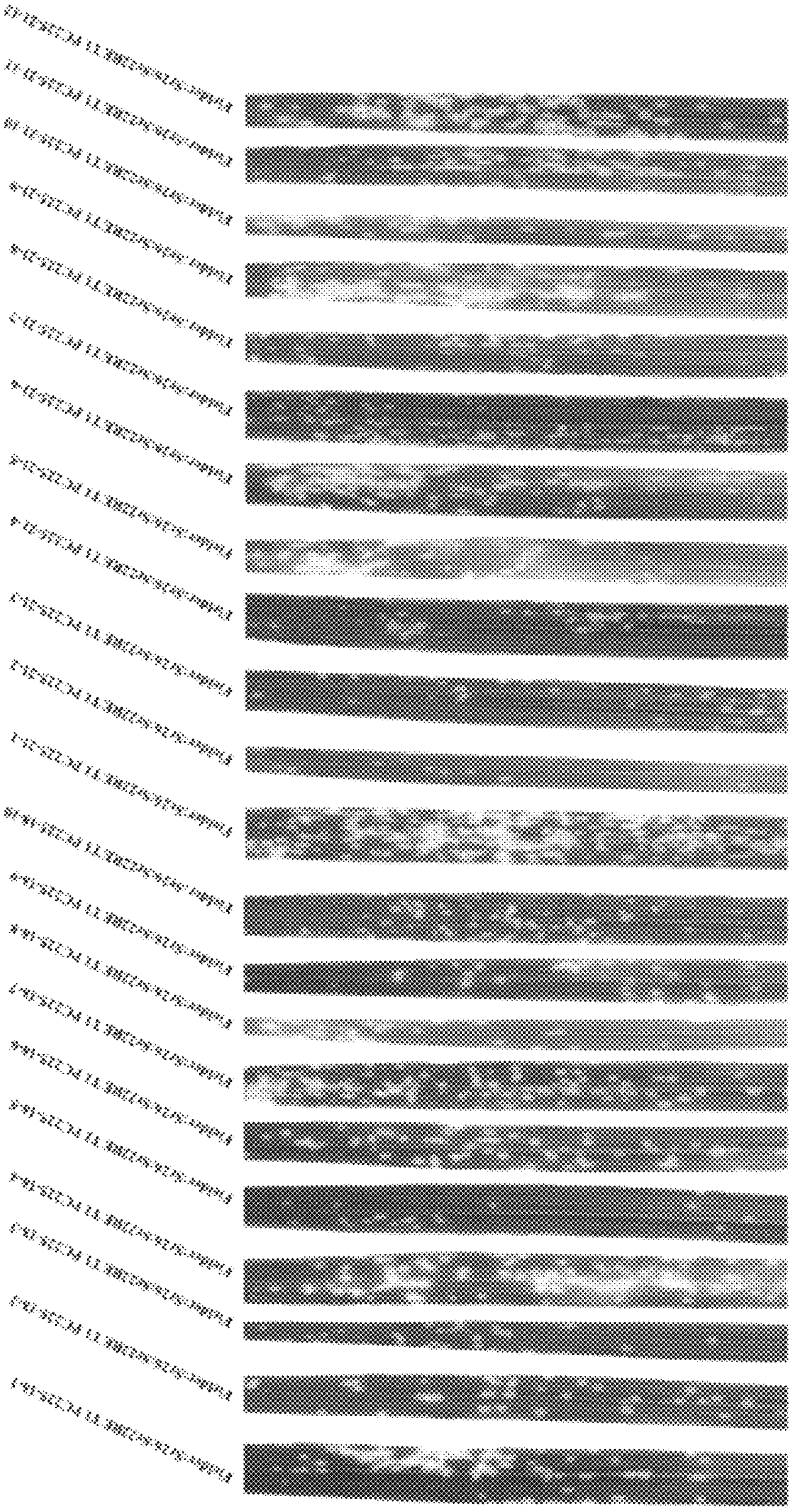

FIG. 9—Validation of the Sr26 candidate gene by transformation validation at the T1 generation of four independent TO families inoculated with Pgt race 98-1,2(3)(5),6. Phenotypic responses of Fielder:Sr26:Sr22RE T1 plants from TO families PC225-18 (10 plants) and PC225-21 (12 plants) with susceptible control Fielder.

Figure 10:
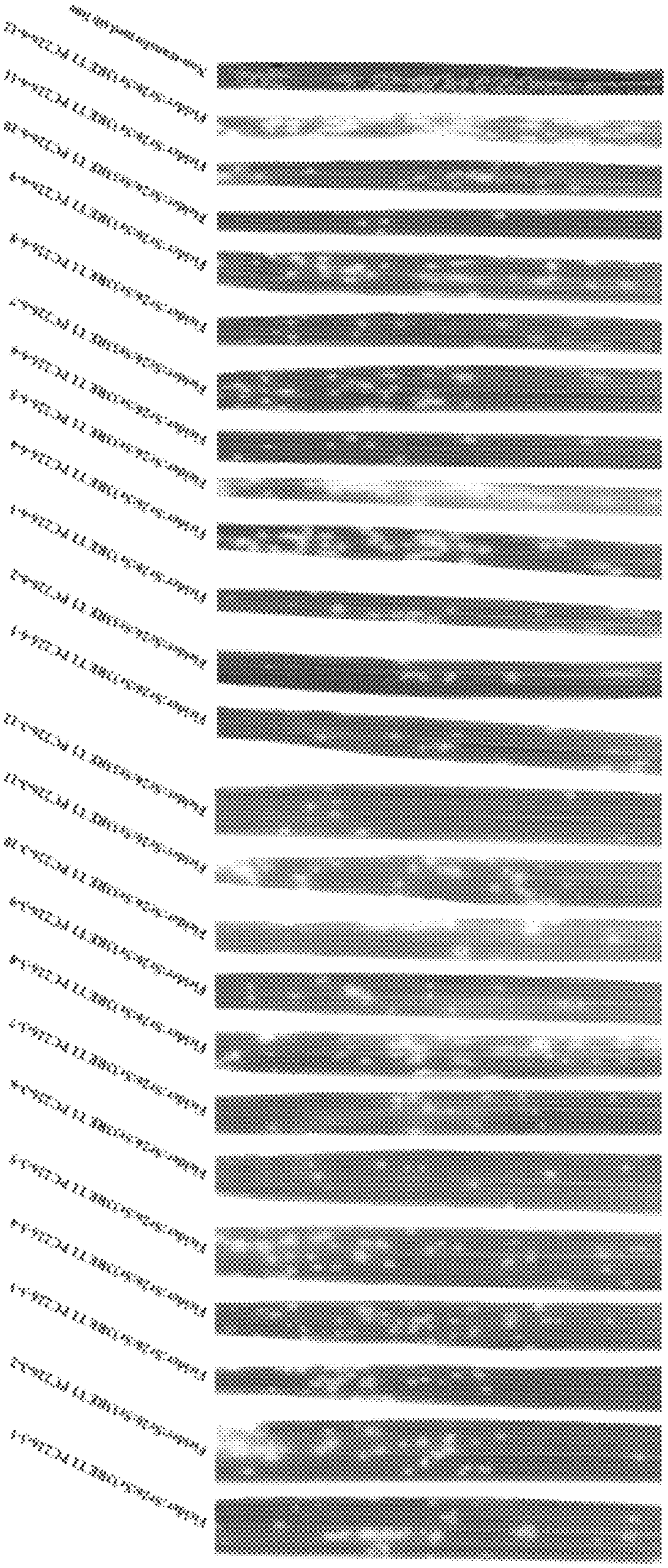

FIG. 10—Validation of the Sr26 candidate gene by transformation validation at the T1 generation of four independent TO families inoculated with Pgt race 98-1,2(3)(5),6. Phenotypic responses of Fielder:Sr26:Sr33RE TI plants from TO families PC226-3 (12 plants) and PC226-6 (12 plants) together with susceptible control Fielder.

Figure 11:
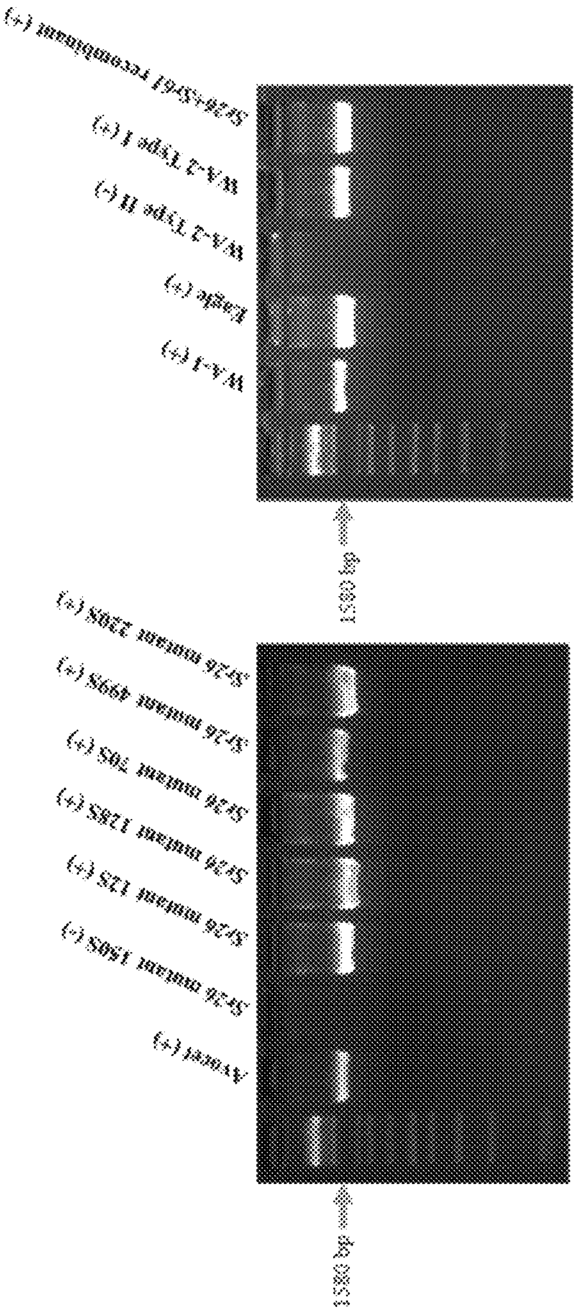
Figure 11:
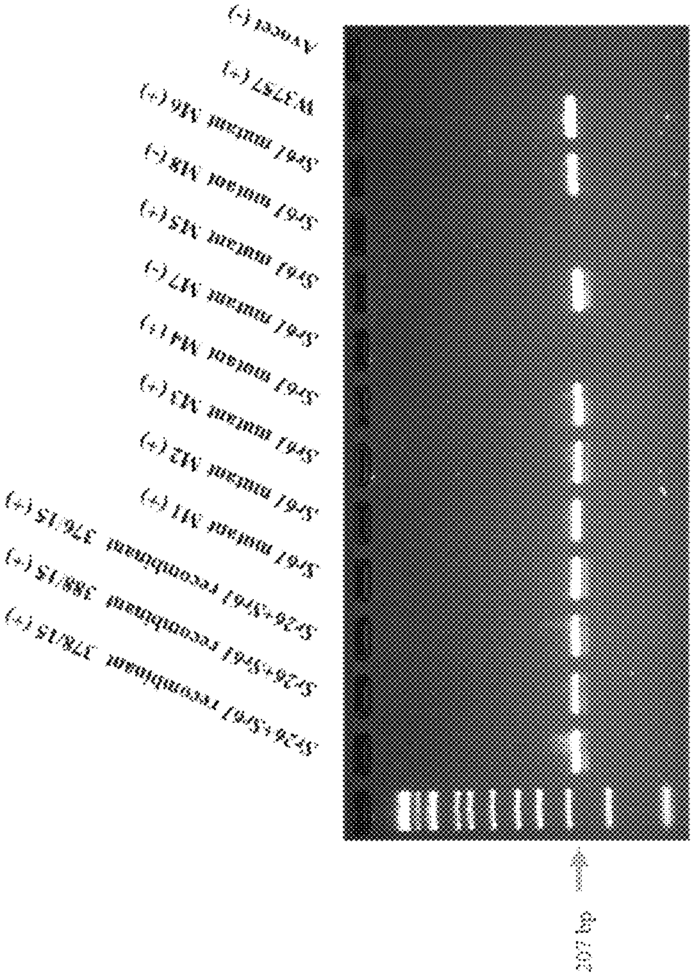

FIG. 11—Agarose gel images showing PCR products amplified from genetic stocks and mutant lines by Sr26 and Sr61 gene-specific markers. (a) Gene specific marker for Sr26. Plus and minus inside the brackets indicate the presence and absence of the respective target gene in each genotype. (b) Gene specific marker for Sr61. Plus and minus inside the brackets indicate the presence and absence of the respective target gene in each genotype.

Figure 12:
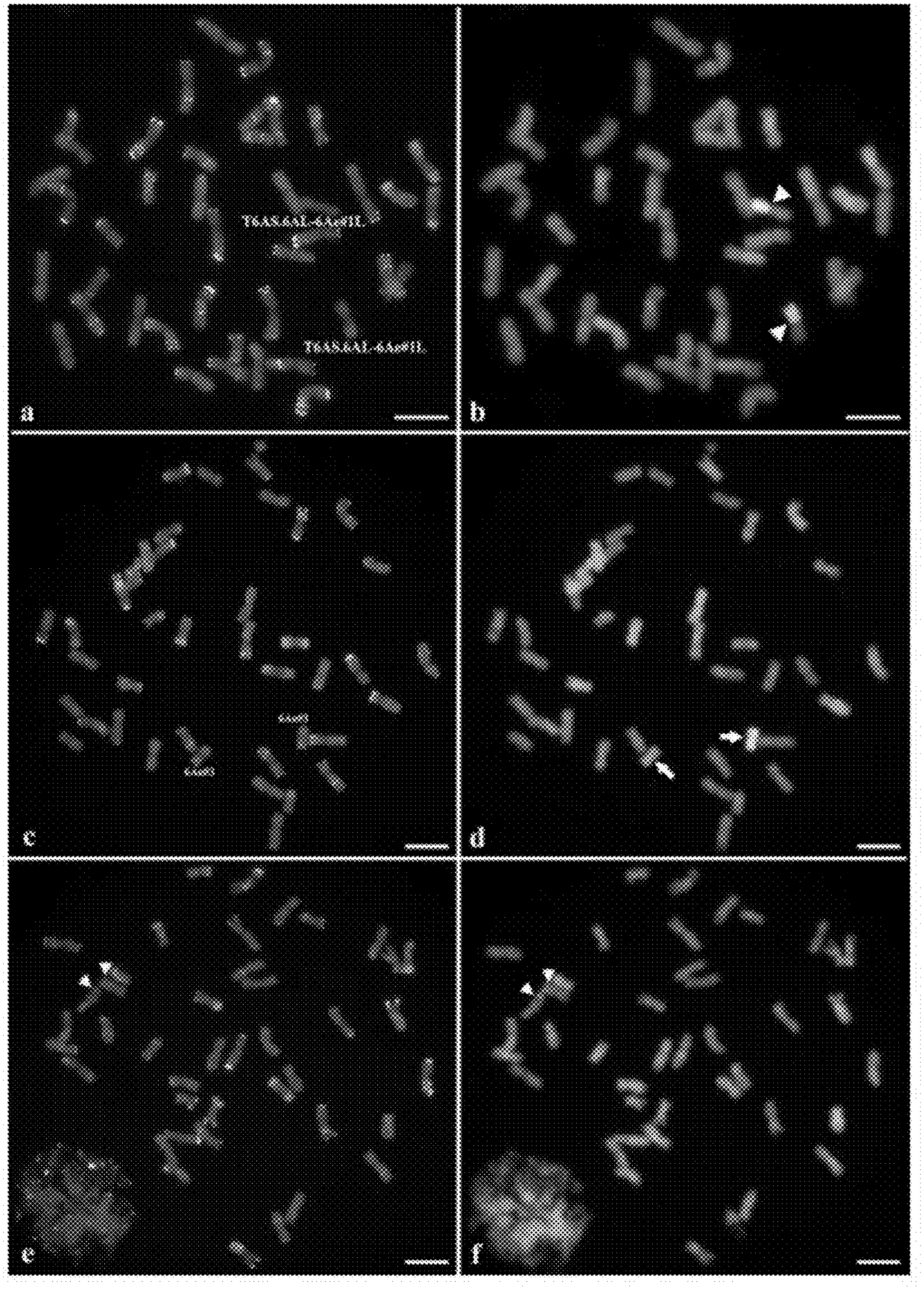

FIG. 12—Sequential fluorescence in situ hybridization (ND-FISH) and genomic in situ hybridization (GISH) of metaphase chromosomes of Avocet+Lr46 (a and b), W3757 (c and d), recombinant 378/15 (e and f). For FISH (a, c, and e), Oligo-pScI19.2-1 and Oligo-pTa535-1 were labelled with 6-carboxyfluorescein (6-FAM) and 6-carboxytetramethylrhodamine (Tamra), generating green and red signals, respectively, and allowing us to identify individual chromosomes. Chromosomes were counterstained with 4',6-diamidino-2-phenylindole (DAPI) and fluoresced blue. For GISH (b, d, and f). Pseuduroegneria stipifolia DNA was labeled with biotin-16-dUTP and detected with fluorescein-avidin DN, which fluoresced yellow-green. Chromosomes were pseudocolored red. Arrowheads point to the translocation breakpoints (b, e, and f) and arrows point to the centromeres (d). Bars, 10 μm.

Figure 13:
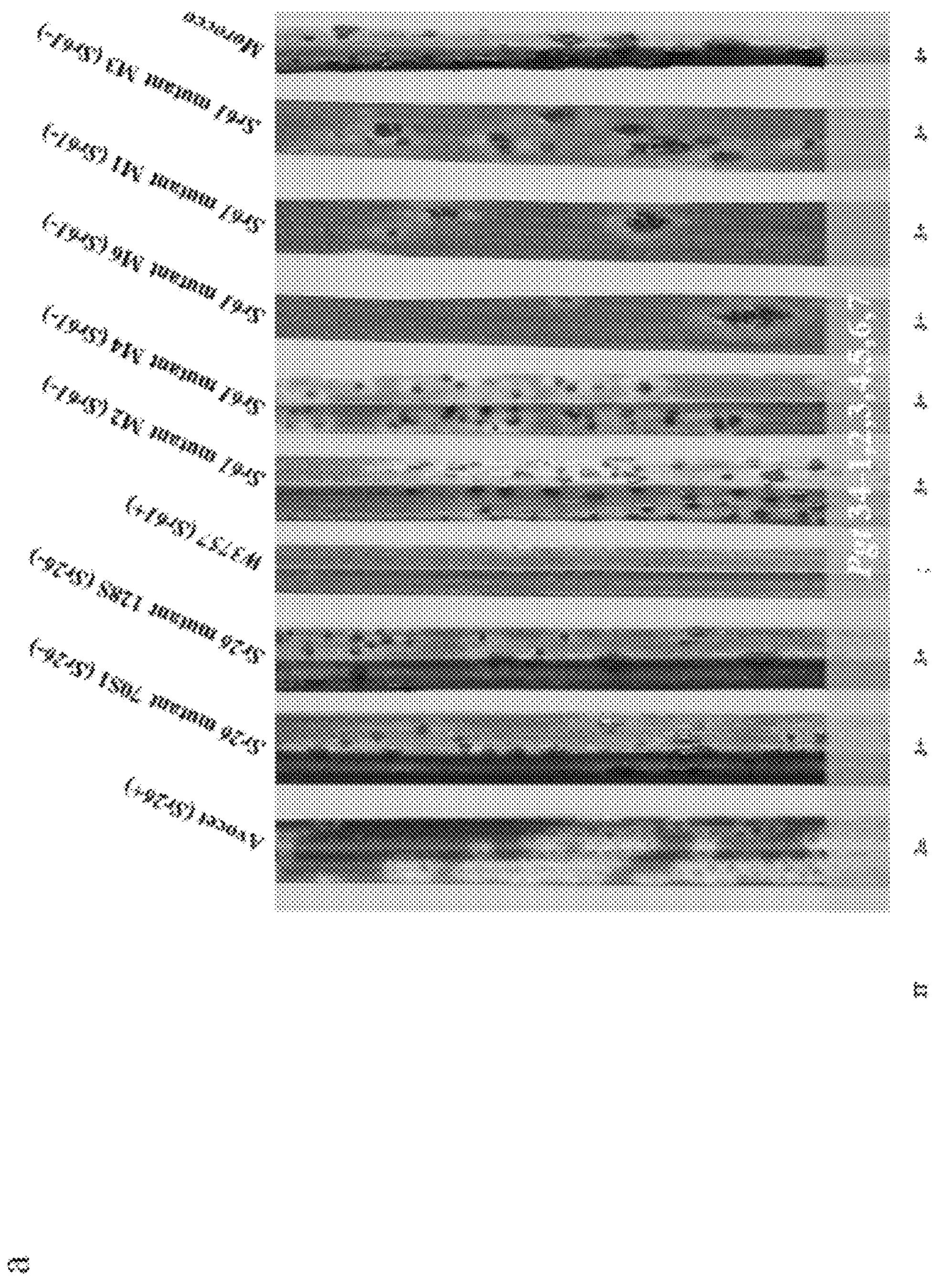
Figure 13:
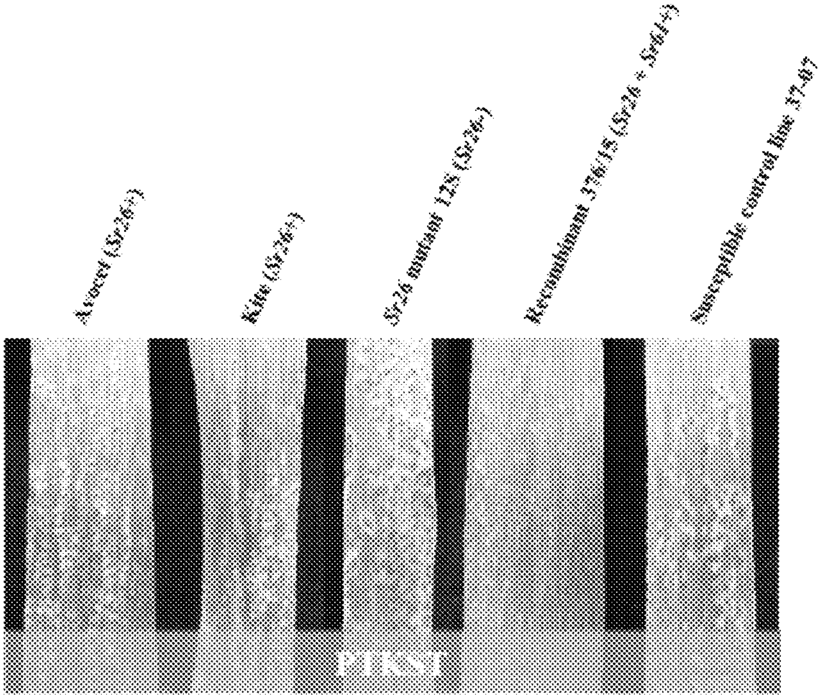
Figure 13:
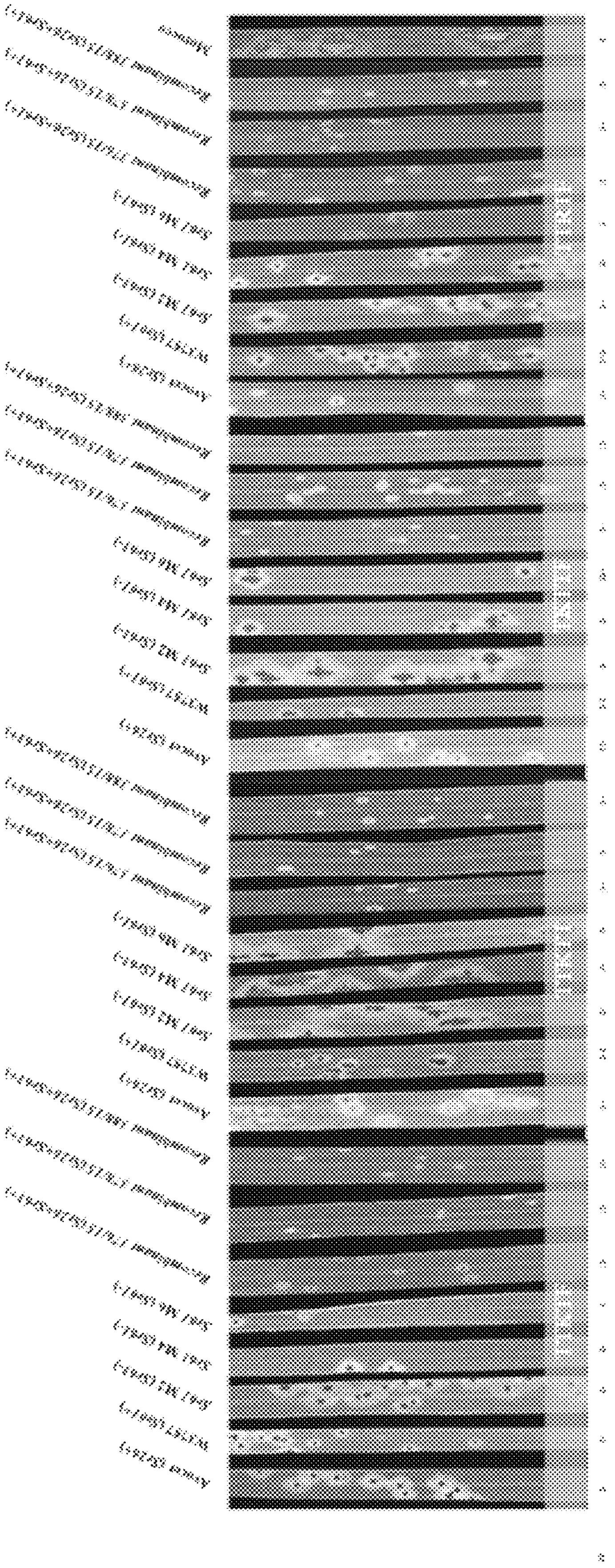

FIG. 13—Seedling and adult plant stem rust responses in lines containing Sr26 and Sr61 when infected with multiple Pgt races (a) Stem rust response of seedlings infected with Pgt 34-1,2,3,4,5,6,7 at 12 days post inoculation (dpi) under greenhouse conditions; (b) Stem rust response at 14 dpi on flag leaves infected with Pgt PTKST under greenhouse conditions at adult plant stage: (c) Stem rust responses on seedlings infected with Pgt pathotypes TTKTF, TTKTT, TKTTF, and TTRTF.

Figure 14:
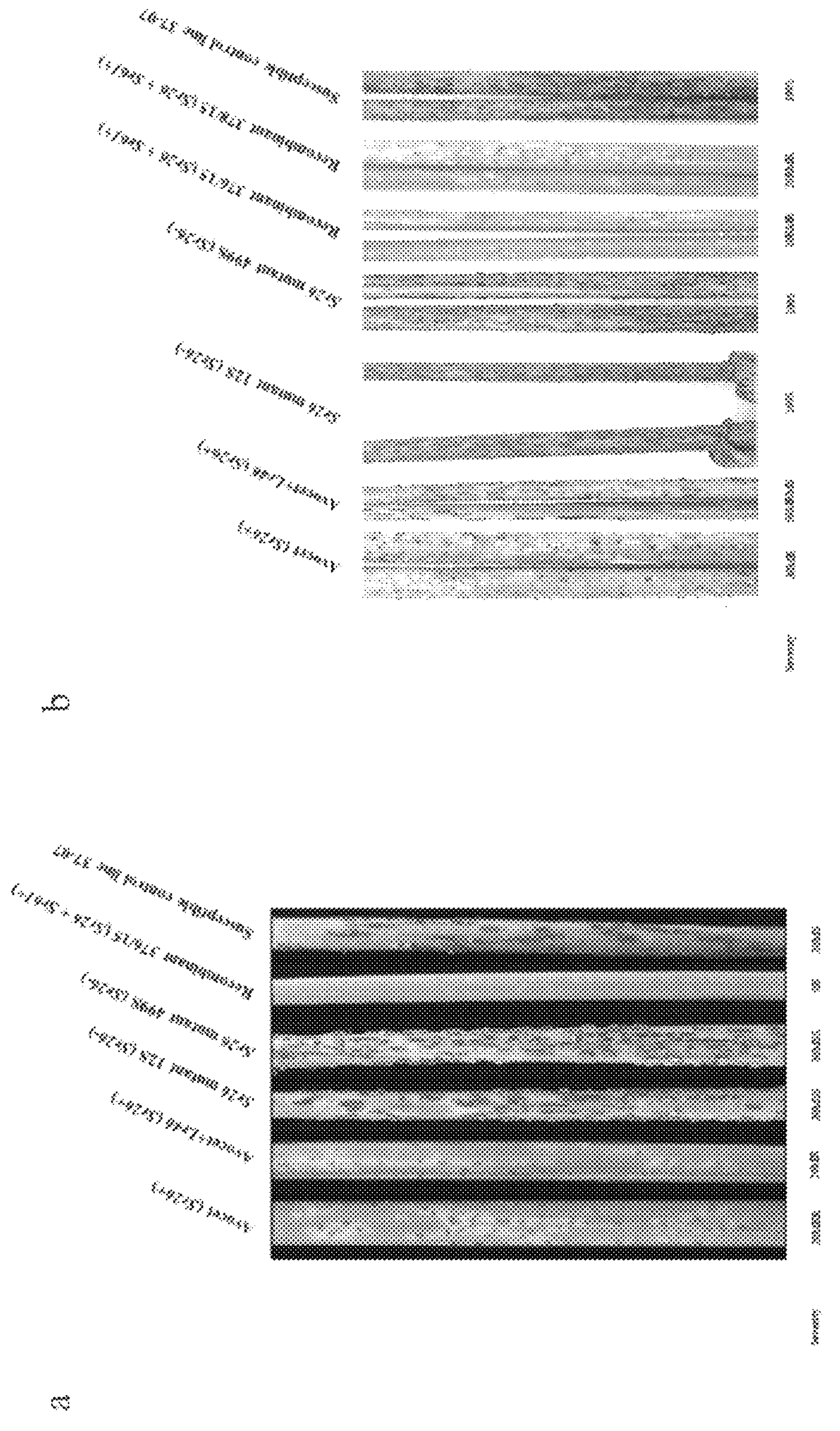
Figure 14:
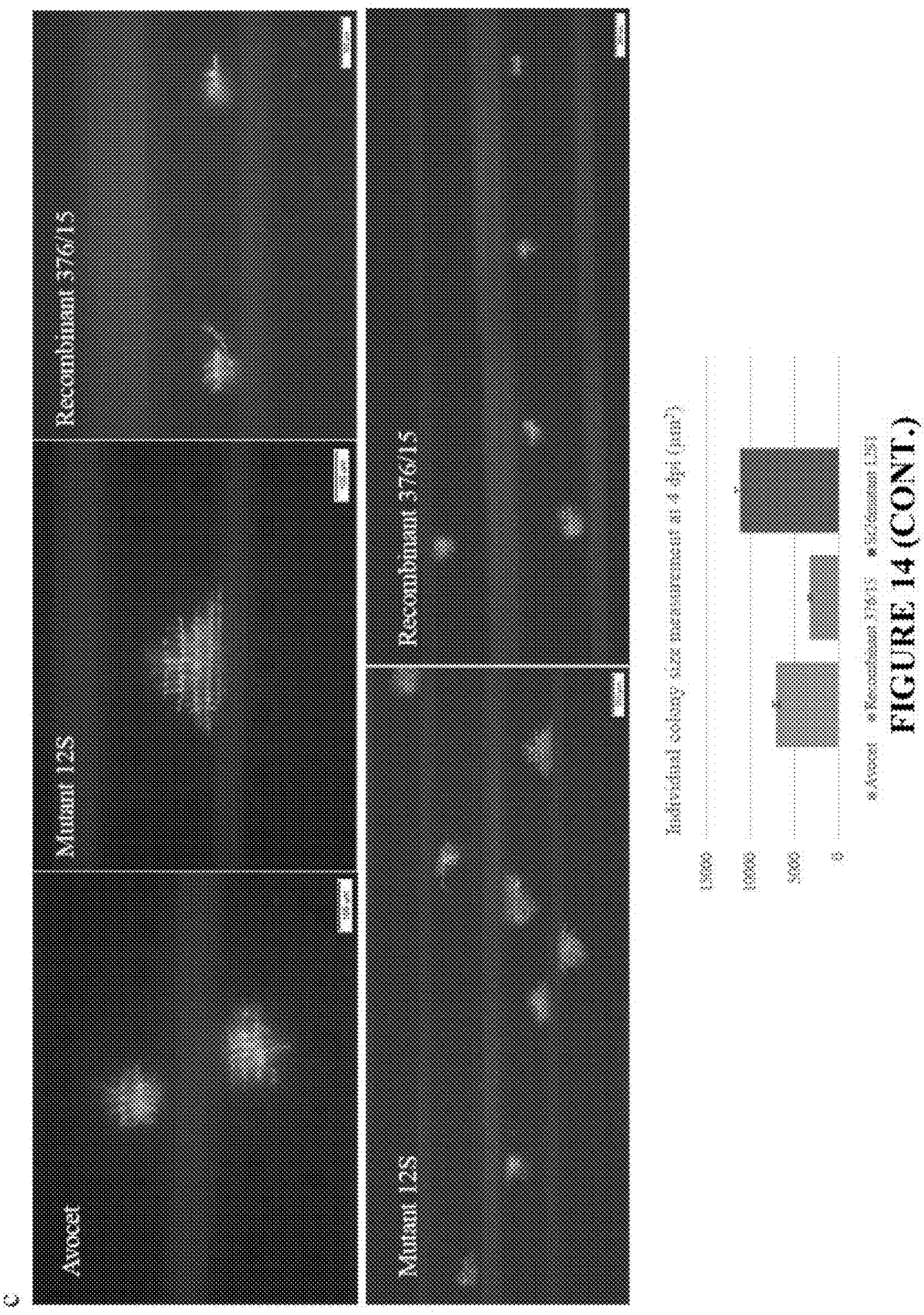
Figure 14:
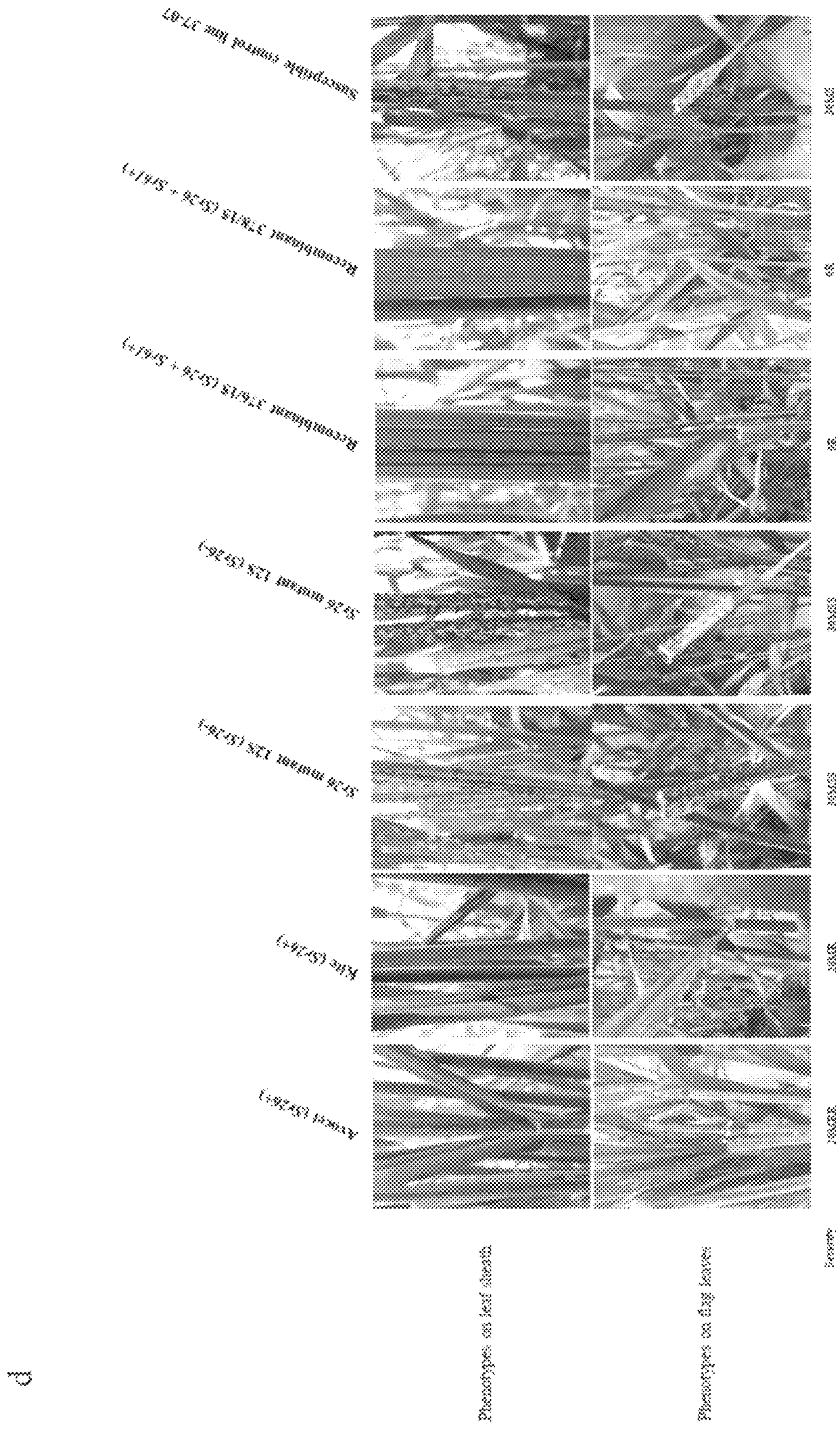

FIG. 14—Stem rust responses of leaf sheaths and stems inoculated with Pgt race PTKST. (a) Stem rust responses at 20 dpi on leaf sheaths of adult plants under greenhouse condition; (b) Stem rust responses at 20 dpi on adult plant stems under field conditions: (c) Microscopic observations and the measurements of average individual colony sizes (30 colonies on average per entry) on the adult plant leaf sheath at 4 dpi under greenhouse conditions; (d) Adult plant responses on leaf sheaths and flag leaves under greenhouse conditions. Disease severities are labelled under each entry and all results were obtained based on three biological and technical replicates.

Figure 15:
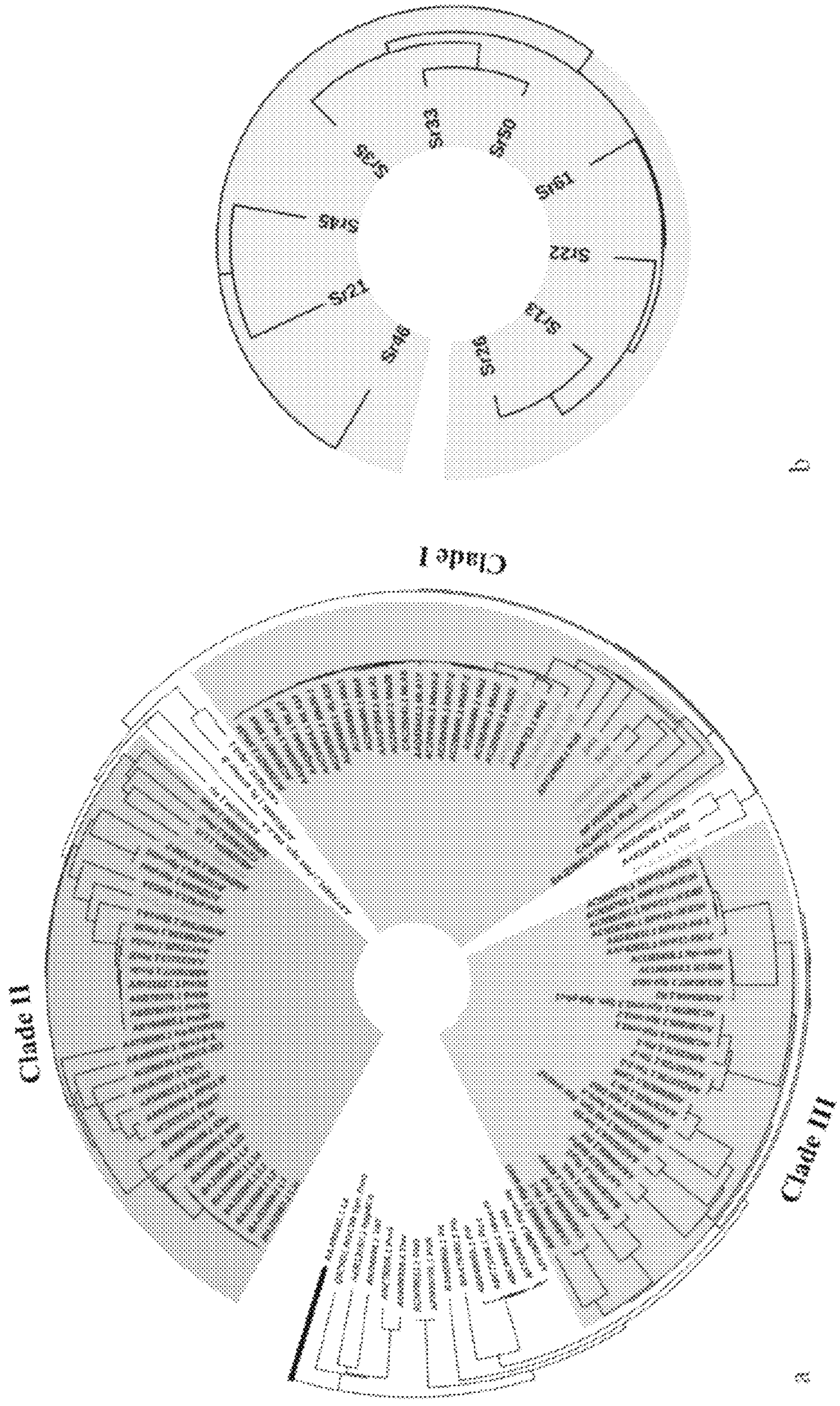

FIG. 15—Phylogenetic analysis of the relationship of Sr26, Sr61 and CNL type immune receptors from plants. (a) TIR type immune receptor L6 added for comparison is shown as root, all the previously cloned wheat stem rust R genes are labelled in orange, Sr26 and Sr61 are in green. Clades 1, II, and Ill are shaded in blue, green, and pink, respectively; (b) Evolutionary relationship between all cloned CNL type wheat stem rust R genes.

Figure 16A:
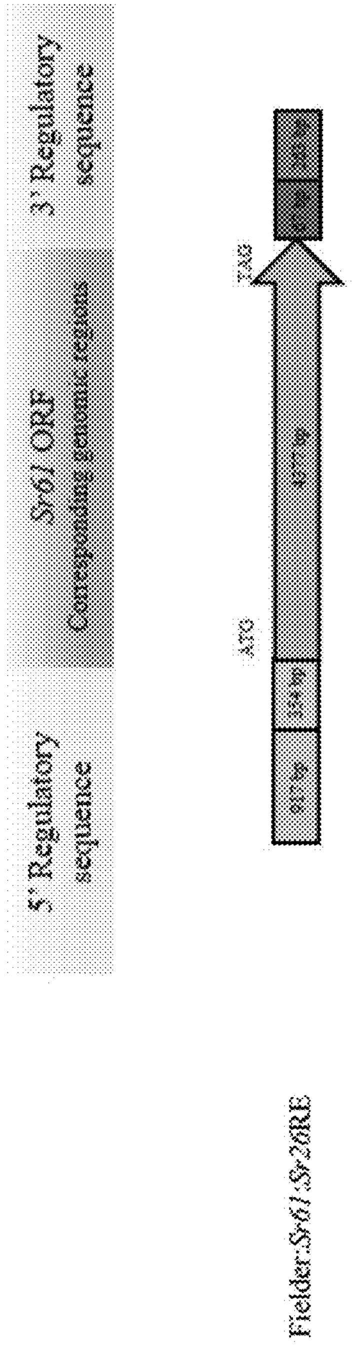

FIG. 16—Validation of the Sr61 candidate gene by transformation. (a) construct used for transformation. (b) Phenotypic responses of representative TO plants when inoculated with Pgt race 98-1,2,(3),(5),6 (isolate 98-1,2,(3),(5),6-7) along with non-transgenic Fielder lines.

Figure 17:
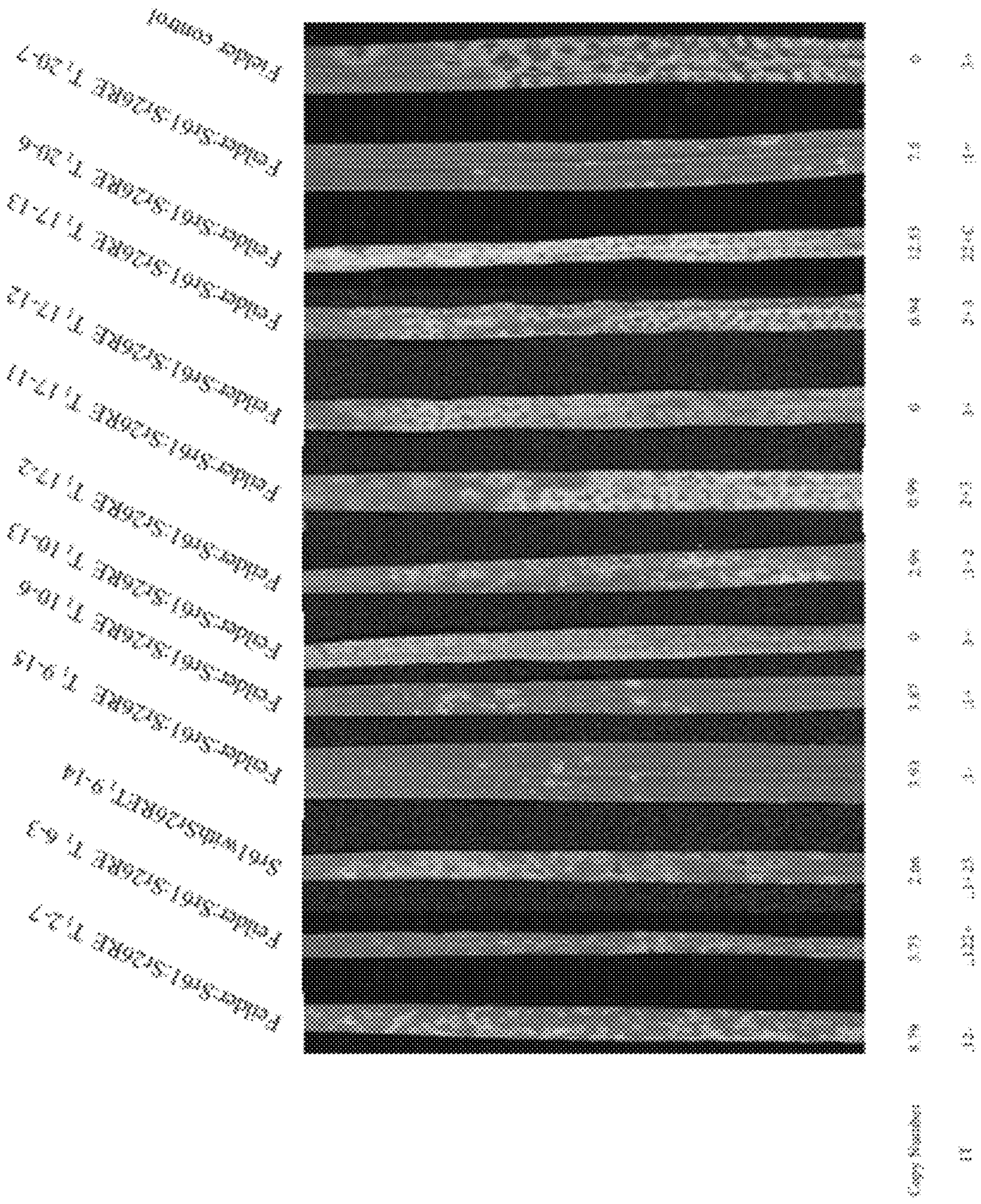

FIG. 17—Validation of the Sr61 candidate gene by transformation at the TI generation of six independent TO families inoculated with Pgt race 98-1,2,(3),(5),6. Phenotypic responses of Fielder:Sr61:Sr26RE TI plants from TO families together with susceptible control Fielder labelled with copy numbers and infection types.

KEY TO THE SEQUENCE LISTING

SEQ ID NO:1—Amino acid sequence of stem rust resistance polypeptide Sr61 polypeptide.

SEQ ID NO:2—Open reading frame encoding Sr61 polypeptide.

SEQ ID NO:3—Amino acid sequence of Sr26 polypeptide.

SEQ ID NO:4—Amino acid sequence of Sr13 polypeptide (ATE88995.1).

SEQ ID NO:5—Amino acid sequence of Sr2l polypeptide (AVK42833.1).

SEQ ID NO:6—Amino acid sequence of Sr22 polypeptide (CUM44200.1).

SEQ ID NO:7—Amino acid sequence of Sr33 polypeptide (AGQ17386.1).

SEQ ID NO:8—Amino acid sequence of Sr35 polypeptide (AGP75918.1).

SEQ ID NO:9—Amino acid sequence of Sr45 polypeptide (CUM44213.1).

SEQ ID NO:10—Amino acid sequence of Sr46 polypeptide.

SEQ ID NO:11—Amino acid sequence of Sr50 polypeptide (ALO61074.1).

SEQ ID NO:12—p-loop consensus motif.

SEQ ID NO:13—Sr61 p-loop motif.

SEQ ID NO:14—Sr61 p-loop motif extended.

SEQ ID NO:15—kinase 2 consensus motif

SEQ ID NO: 16—Sr61 kinase 2 motif.

SEQ ID NO: 17—Sr61 kinase 2 motif extended.

SEQ ID NO:18—kinase 3a consensus motif.

SEQ ID NO:19—Sr61 kinase 3a motif.

SEQ ID NO:20—Sr61 kinase 3a motif extended.

SEQ ID NO:21—LRR domain repeat consensus sequence.

SEQ ID NO:22—Genomic region encoding Sr61 polypeptide.

SEQ ID NO's 23 to 46—Oligonucleotide primers.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, plant molecular biology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984). J. Sambrook et al., Molecular Cloning: A Laboratory Manual, Cold Spring Harbour Laboratory Press (1989), T.A. Brown (editor), Essential Molecular Biology: A Practical Approach, Volumes 1 and 2, IRL Press (1991), D.M. Glover and B.D. Hames (editors), DNA Cloning: A Practical Approach. Volumes 1-4, IRL Press (1995 and 1996), and F.M. Ausubel et al. (editors), Current Protocols in Molecular Biology, Greene Pub. Associates and Wiley-Interscience (1988, including all updates until present). Ed Harlow and David Lane (editors) Antibodies: A Laboratory Manual, Cold Spring Harbour Laboratory. (1988), and J.E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10%, more preferably 5%, of the particular term.

Polypeptides

As used herein, the term "Sr61" relates to a protein family which share high primary amino acid sequence identity, for example at least 60%, at least 70%, least 80%, at least 90%, or at least 95% identity with the amino acid sequences provided as SEQ ID NO:1. The present inventors have determined that some variants of the Sr61 protein family, when expressed in a plant, confer upon the plant resistance to at least one strain of *Puccinia graminis*. An example of such a variant comprises an amino acid sequence provided as SEQ ID NO:1. Thus, variants which confer resistance are referred to herein as Sr61 (resistant) polypeptides or proteins, whereas those which do not (see as the mutants mentioned in FIG. 3) are referred to herein as Sr61 (susceptible) polypeptides. In a preferred embodiment, Sr61 (resistant) proteins do not comprise a mutation, such as a valine, at a position corresponding to amino acid number 91 of SEQ ID NO: 1, or a mutation, such as a lysine, at a position corresponding to amino acid number 136 of SEQ ID NO:1, or a mutation, such as a phenylalanine, at a position corresponding to amino acid number 499 of SEQ ID NO: 1, or a mutation, such as a isoleucine, at a position corresponding to amino acid number 645 of SEQ ID NO:1, or a mutation, such as a tyrosine, at a position corresponding to amino acid number 744 of SEQ ID NO:1, or a mutation, such as a lysine, at a position corresponding to amino acid number 856 of SEQ ID NO:1.

Polypeptides of the invention typically comprise a coiled coil (CC) domain towards the N-terminus, followed by a nucleotide binding (NB) domain and a leucine rich repeat (LRR) domain towards the C-terminus (see FIGS. 3 and 5). Each of these three types of domains are common in polypeptides that confer resistance to plant pathogens. In addition, CC-NB-LRR containing polypeptides are a known large class of polypeptides which, as a class, confer resistance across a wide variety of different plant pathogens (see, for example, Bulgarelli et al., 2010; McHale et al., 2006; Takken et al., 2006; Wang et al., 2011; Gennaro et al., 2009; and Dilbirligi et al., 2(03), although each CC-NB-LRR polypeptides is specific to a particular species or sub-species of pathogen. Accordingly, by aligning the polypeptides of the invention with other CC-NB-LRR polypeptides, combined with the large number of studies on these types of proteins as well as CC domains, NB domains and LRR domains, the skilled person has a considerable amount of guidance for designing functional variants of the specific polypeptides provided herein (such as provided in FIGS. 3 and 5).

A coiled-coil domain or motif is a structural motif which is one of the most common tertiary structures of proteins where α-helices are coiled together like the strands of a rope. Computer programs have been devised to detect heptads and resulting in coiled-coil structures (see, for example Delorenzi and Speed, 2002). Coiled coils typically comprise a repeated pattern, hxrhcxc, of hydrophobic (h) and charged (c) amino-acid residues, referred to as a heptad repeats. The positions in the heptad repeat are usually labeled abcde/j, where a and d are the hydrophobic positions, often being occupied by isoleucine, alanine, leucine or valine. Folding a protein with these heptads into an α-helical secondary structure causes the hydrophobic residues to be presented as a 'stripe' that coils gently around the helix in left-handed fashion, forming an amphipathic structure.

The NB domain is present in resistance genes as well as several kinases such as ATP/GTP-binding proteins. This domain typically contains three motifs: kinase-1a (p-loop), a kinase-2, and a putative kinase-3a (Traut 1994: Tameling et al., 2(X2). The consensus sequence of GxxGxGK(T/S)T (SEQ ID NO:12) (GFGGLGKTT (SEQ ID NO:13), more preferably VSIVGFGGLGKTTL (SEQ ID NO:14), in the polypeptide which confers resistance to *Puccinia graminis* provided as SEQ ID NO:1), DDxW (SEQ ID NO: 15) (DDLW (SEQ ID NO:16), more preferably RYLIIID-DLWDVS (SEQ ID NO:17), in the polypeptide which confers resistance to *Puccinia graminis* provided as SEQ ID NO:1) and GxxxxxTxR (SEQ ID NO:18) (GSRVVVTTR (SEQ ID NO:19), more preferably sequence GSRVVVT-TRIQEV (SEQ ID NO:20), in the polypeptide which confers resistance to *Puccinia graminis* provided as SEQ ID NO:1) for the resistance gene motifs p-loop, kinase-2, and the putative kinase-3a, respectively, are different from those present in other NB-encoding proteins. Other motifs present in the NB domain of NB/LRR-type resistance genes are GLPL, RNBS-D and MHD (Meyers et al., 1999). The sequences interspersing these motifs and domains can be very different even among homologues of a resistance gene (Michelmore and Meyers, 1998: Pan et al., 2000).

A leucine-rich domain is a protein structural motif that forms an α/β horseshoe fold (Enkhbayar et al., 2004). The LRR domain contains 2-41 imperfect repeats, each about 25 amino acids long with a consensus amino acid sequence of xxLxLxxxx (SEQ ID NO:21) (Cooley et al., 2000). In an embodiment, a polypeptide of the invention comprises about 2 to about 15, more preferably about 4 to about 10, more preferably about 6 leucine rich repeats. These repeats commonly fold together to form a solenoid protein domain. Typically, each repeat unit has beta strand-tum-alpha helix structure, and the assembled domain, composed of many such repeats, has a horseshoe shape with an interior parallel beta sheet and an exterior array of helices.

As used herein, "resistance" is a relative term in that the presence of a polypeptide of the invention (i) reduces the disease symptoms of a plant comprising the gene (R (resistant) gene) that confers resistance, relative to a plant lacking the R gene, and/or (ii) reduces pathogen reproduction or spread on a plant or within a population of plants comprising the R gene. Resistance as used herein is relative to the "susceptible" response of a plant to the same pathogen. Typically, the presence of the R gene improves at least one production trait of a plant comprising the R gene when infected with the pathogen, such as grain yield, when compared to an isogemc plant infected with the pathogen but lacking the R gene. The isogenic plant may have some level of resistance to the pathogen, or may be classified as susceptible. Thus, the terms "resistance" and "enhanced resistance" are generally used herein interchangeably. Furthermore, a polypeptide of the invention does not necessarily confer complete pathogen resistance, for example when some symptoms still occur or there is some pathogen reproduction on infection but at a reduced amount within a plant or a population of plants. Resistance may occur at only some stages of growth of the plant, for example in adult plants (fully grown in size) and less so, or not at all, in seedlings, or at all stages of plant growth. In an embodiment, resistance occurs at adult and seedling stage. By using a transgenic strategy to express an Sr6l polypeptide in a plant, the plant of the invention can be provided with resistance throughout its growth and development. Enhanced resistance can be determined by a number of methods known in the art such as analysing the plants for the amount of pathogen and/or analysing plant growth or the amount of damage or disease symptoms to a plant in the presence of the pathogen, and comparing one or more of these parameters to an isogenic plant lacking an exogenous gene encoding a polypeptide of the invention.

By "substantially purified polypeptide" or "purified polypeptide" we mean a polypeptide that has generally been separated from the lipids, nucleic acids, other peptides, and other contaminating molecules with which it is associated in its native state. Preferably, the substantially purified polypeptide is at least 90% free from other components with which it is naturally associated. In an embodiment, the polypeptide of the invention has an amino acid sequence which is different to a naturally occurring Sr61 polypeptide i.e. is an amino acid sequence variant.

Transgenic plants and host cells of the invention may comprise an exogenous polynucleotide encoding a polypeptide of the invention. In these instances, the plants and cells produce a recombinant polypeptide. The term "recombinant" in the context of a polypeptide refers to the polypeptide encoded by an exogenous polynucleotide when produced by a cell, which polynucleotide has been introduced into the cell or a progenitor cell by recombinant DNA or RNA techniques such as, for example, transformation. Typically, the cell comprises a non-endogenous gene that causes an altered amount of the polypeptide to be produced. In an embodiment, a "recombinant polypeptide" is a polypeptide made by the expression of an exogenous (recombinant) polynucleotide in a plant cell.

The terms "polypeptide" and "protein" are generally used interchangeably.

The % identity of a polypeptide is determined by GAP (Needleman and Wunsch, 1970) analysis (GCG program) with a gap creation penalty=5, and a gap extension penalty=0.3. The query sequence is at least 500 amino acids in length, and the GAP analysis aligns the two sequences over a region of at least 500 amino acids. More preferably, the query sequence is at least 750 amino acids in length and the GAP analysis aligns the two sequences over a region of at least 750 amino acids. Even more preferably, the query sequence is at least 800 amino acids in length and the GAP analysis aligns the two sequences over a region of at least 800 amino acids. Even more preferably, the GAP analysis aligns two sequences over their entire length, which for an Sr61 polypeptide is about 889 amino acid residues.

As used herein a "biologically active" fragment is a portion of a polypeptide of the invention which maintains a defined activity of the full-length polypeptide such as when expressed in a plant, such as wheat, confers (enhanced) resistance to stem rust caused by at least one strain of *Puccinia graminis* when compared to an isogenic plant not expressing the polypeptide. Biologically active fragments can be any size as long as they maintain the defined activity but are preferably at least 700 or at least 800 or at least 850 amino acid residues long. Preferably, the biologically active fragment maintains at least 10%, at least 50%, at least 75% or at least 90%, of the activity of the full length protein. In an embodiment, the biologically active fragment comprises functional CC, NB and LRR domains.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is preferably at least 60%, at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In an embodiment, a polypeptide of the invention is not a naturally occurring polypeptide.

As used herein, the phrase "at a position corresponding to amino acid number" or variations thereof refers to the relative position of the amino acid compared to surrounding amino acids. In this regard, in some embodiments a polypeptide of the invention may have deletional or substitutional mutation which alters the relative positioning of the amino acid when aligned against, for instance, SEQ ID NO:1.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics. Preferred amino acid sequence mutants have one, two, three, four or less than 10 amino acid changes relative to the reference wildtype polypeptide.

Mutant (altered) polypeptides can be prepared using any technique known in the art, for example, using directed evolution, rational design strategies or mutagenesis (see below). Products derived from mutated/altered DNA can readily be screened using techniques described herein to determine if, when expressed in a plant, such as wheat, confer (enhanced) resistance to at least one strain of *Puccinia graminis*. For instance, the method may comprise producing a transgenic plant expressing the mutated/altered DNA and determining the effect of the pathogen on the growth of the plant.

In designing amino acid sequence mutants, the location of the mutation site and the nature of the mutation will depend on characteristic(s) to be modified. The sites for mutation can be modified individually or in series. e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. Where it is desirable to maintain a certain activity it is preferable to make no, or only conservative substitutions, at amino acid positions which are highly conserved in the relevant protein family. Examples of conservative substitutions are shown in Table 1 under the heading of "exemplary substitutions".

In a preferred embodiment a mutant/variant polypeptide has one or two or three or four conservative amino acid changes when compared to a naturally occurring polypeptide. Details of conservative amino acid changes are provided in Table 1. In a preferred embodiment, the changes are not in one or more of the motifs which are highly conserved between the different polypeptides provided herewith, and/or not in the important motifs of Sr61 polypeptides identified herein. As the skilled person would be aware, such minor changes can reasonably be predicted not to alter the activity of the polypeptide when expressed in a recombinant cell.

The primary amino acid sequence of a polypeptide of the invention can be used to design variants/mutants thereof based on comparisons with closely related polypeptides (for example, as shown in FIG. 5). As the skilled addressee will appreciate, residues highly conserved amongst closely related proteins are less likely to be able to be altered, especially with non-conservative substitutions, and activity maintained than less conserved residues (see above).

TABLE 1

| Exemplary substitutions. | |
|---|---|
| Original Residue | Exemplary Substitutions |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr( Y) | trp; phe |
| Val (V) | ile; leu; met; phe, ala |

Also included within the scope of the invention are polypeptides of the present invention which are differentially modified during or after synthesis. e.g., by biotinylation, benzylation, glycosylation, acetylation, phosphorylation, amidation, derivatization by known protecting/blocking groups, proteolytic cleavage, linkage to an antibody molecule or other cellular ligand, etc. The polypeptides may be post-translationally modified in a cell, for example by phosphorylation, which may modulate its activity. These modifications may serve to increase the stability and/or bioactivity of the polypeptide of the invention.

Directed Evolution

In directed evolution, random mutagenesis is applied to a protein, and a selection regime is used to pick out variants that have the desired qualities, for example, increased activity. Further rounds of mutation and selection are then applied. A typical directed evolution strategy involves three steps;

1) Diversification: The gene encoding the protein of interest is mutated and/or recombined at random to create a large library of gene variants. Variant gene libraries can be constructed through error prone PCR (see, for example. Lieung. 1989. Cadv ell and Joyce. 1992), from pools of DNaseI digested fragments prepared from parental templates (Stemmer, 1994a. Stemmer. 1994b; Crameri et al., 1998: Coco et al., 2001) from degenerate oligonucleotides (Ness et al., 2002, Coco, 2002) or from mixtures of both, or even from undigested parental templates (Zhao et al, 1998: Eggert et al., 2005; Jedquek et al., 2008) and are usually assembled through PCR. Libraries can also be made from parental sequences recombined in vivo or in vitro by either homologous or non-homologous recombination (Ostermeier et al., 1999; Volkov et al., 1999; Sieber et al., 2001). Variant gene libraries can also be constructed by sub-cloning a gene of interest into a suitable vector, transforming the vector into a "mutator" strain such as the *E coli* XL-1 red (Stratagene) and propagating the transformed bacteria for a suitable number of generations. Variant gene libraries can also be constructed by subjecting the gene of interest to DNA shuffling (i.e., in vitro homologous recombination of pools of selected mutant genes by random fragmentation and reassembly) as broadly described by Harayama (1998).
2) Selection: The library is tested for the presence of mutants (variants) possessing the desired property using a screen or selection. Screens enable the identification and isolation of high-performing mutants by hand, while selections automatically eliminate all non-functional mutants. A screen may involve screening for the presence of known conserved amino acid motifs. Alternatively, or in addition, a screen may involve expressing the mutated polynucleotide in a host organism or part thereof and assaying the level of activity.
3) Amphication: The variants identified in the selection or screen are replicated many fold, enabling researchers to sequence their DNA in order to understand what mutations have occurred.

Together, these three steps are termed a "round" of directed evolution. Most experiments will entail more than one round. In these experiments, the "winners" of the previous round are diversified in the next round to create a new library. At the end of the experiment, all evolved protein or polynucleotide mutants are characterized using biochemical methods.

Rational Design

A protein can be designed rationally, on the basis of known information about protein structure and folding. This can be accomplished by design from scratch (de novo design) or by redesign based on native scaffolds (see, for example, Hellinga, 1997; and Lu and Berry, Protein Structure Design and Engineering, Handbook of Proteins 2, 1153-1157 (2007)). Protein design typically involves identifying sequences that fold into a given or target structure and can be accomplished using computer models. Computational protein design algorithms search the sequence-conformation space for sequences that are low in energy when folded to the target structure. Computational protein design algorithms use models of protein energetics to evaluate how mutations would affect a protein's structure and function. These energy functions typically include a combination of molecular mechanics, statistical (i.e. knowledge-based), and other empirical terms. Suitable available software includes IPRO (Interative Protein Redesign and Optimization), EGAD (A Genetic Algorithm for Protein Design), Rosetta Design. Sharpen, and Abalone.

Polynucleotides and Genes

The present invention refers to various polynucleotides. As used herein, a "polynucleotide" or "nucleic acid" or "nucleic acid molecule" means a polymer of nucleotides, which may be DNA or RNA or a combination thereof, and includes genomic DNA, mRNA, cRNA, and cDNA. Less preferred polynucleotides include tRNA, siRNA, shRNA and hpRNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein, or comprise one or more modified nucleotides not found in nature, well known to those skilled in the art. The polymer may be single-stranded, essentially double-stranded or partly double-stranded. Basepairing as used herein refers to standard basepairing between nucleotides, including G:U basepairs. "Complementary" means two polynucleotides are capable of basepairing (hybridizing) along part of their lengths, or along the full length of one or both. A "hybridized polynucleotide" means the polynucleotide is actually basepaired to its complement. The term "polynucleotide" is used interchangeably herein with the term "nucleic acid". Preferred polynucleotides of the invention encode a polypeptide of the invention.

By "isolated polynucleotide" we mean a polynucleotide which has generally been separated from the polynucleotide sequences with which it is associated or linked in its native state, if the polynucleotide is found in nature. Preferably, the isolated polynucleotide is at least 90% free from other components with which it is naturally associated, if it is found in nature. Preferably the polynucleotide is not naturally occurring, for example by covalently joining two shorter polynucleotide sequences in a manner not found in nature (chimeric polynucleotide).

The present invention involves modification of gene activity and the construction and use of chimeric genes. As used herein, the term "gene" includes any deoxyribonucleotide sequence which includes a protein coding region or which is transcribed in a cell but not translated, as well as associated non-coding and regulatory regions. Such associated regions are typically located adjacent to the coding region or the transcribed region on both the 5' and 3' ends for a distance of about 2 kb on either side. In this regard, the gene may include control signals such as promoters, enhancers, termination and/or polyadenylation signals that are naturally associated with a given gene, or heterologous control signals in which case the gene is referred to as a "chimeric gene". The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

A "Sr6J gene" as used herein refers to a nucleotide sequence which is homologous to an isolated Sr6l cDNA (such as provided in SEQ ID NO:2). As described herein, some alleles and variants of the Sr6/gene family encode a protein that confers resistance to at least one strain of *Puccinia graminis*. Sr6l genes include the naturally occurring alleles or variants existing in cereals such as wheat, as well as artificially produced variants.

A genomic form or clone of a gene containing the transcribed region may be interrupted with non-coding sequences termed "introns" or "intervening regions" or "intervening sequences", which may be either homologous or heterologous with respect to the "exons" of the gene. An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. As described herein, the wheat Sr6/genes (both resistant and susceptible alleles) contain two introns in their protein coding regions. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above. A gene may be introduced into an appropriate vector for extrachromosomal maintenance in a cell or, preferably, for integration into the host genome.

As used herein, a "chimeric gene" refers to any gene that comprises covalently joined sequences that are not found joined in nature. Typically, a chimeric gene comprises regulatory and transcribed or protein coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. In an embodiment, the protein coding region of an Sr61 gene is operably linked to a promoter or polyadenylation/terminator region which is heterologous to the Sr61 gene, thereby forming a chimeric gene. The term "endogenous" is used herein to refer to a substance that is normally present or produced in an unmodified plant at the same developmental stage as the plant under investigation. An "endogenous gene" refers to a native gene in its natural location in the genome of an organism. As used herein, "recombinant nucleic acid molecule", "recombinant polynucleotide" or variations thereof refer to a nucleic acid molecule which has been constructed or modified by recombinant DNA/RNA technology. The terms "foreign polynucleotide" or "exogenous polynucleotide" or "heterologous polynucleotide" and the like refer to any nucleic acid which is introduced into the genome of a cell by experimental manipulations.

Foreign or exogenous genes may be genes that are inserted into a non-native organism or cell, native genes introduced into a new location within the native host, or chimeric genes. Alternatively, foreign or exogenous genes may be the result of editing the genome of the organism or cell, or progeny derived therefrom. A "transgene" is a gene that has been introduced into the genome by a transformation procedure. The term "genetically modified" includes introducing genes into cells by transformation or transduction, gene editing, mutating genes in cells and altering or modulating the regulation of a gene in a cell or organisms to which these acts have been done or their progeny.

Furthermore, the term "exogenous" in the context of a polynucleotide (nucleic acid) refers to the polynucleotide when present in a cell that does not naturally comprise the polynucleotide. The cell may be a cell which comprises a non-endogenous polynucleotide resulting in an altered amount of production of the encoded polypeptide, for example an exogenous polynucleotide which increases the expression of an endogenous polypeptide, or a cell which in its native state does not produce the polypeptide. Increased production of a polypeptide of the invention is also referred to herein as "over-expression". An exogenous polynucleotide of the invention includes polynucleotides which have not been separated from other components of the transgenic (recombinant) cell, or cell-free expression system, in which it is present. and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically, such chimeric polvnucleotides comprise at least an open reading frame encoding a polypeptide of the invention operably linked to a promoter suitable of driving transcription of the open reading frame in a cell of interest.

The % identity of a polynucleotide is determined by GAP (Needleman and Wunsch. 1970) analysis (GCG program) with a gap creation penalty=5, and a gap extension penalty=0.3. The query sequence is at least 450 nucleotides in length, and the GAP analysis aligns the two sequences over a region of at least 450 nucleotides. Preferably, the query sequence is at least 1,500 nucleotides in length, and the GAP analysis aligns the two sequences over a region of at least 1,500 nucleotides. Even more preferably, the query sequence is at least 2,700 nucleotides in length and the GAP analysis aligns the two sequences over a region of at least 2,700 nucleotides. Even more preferably, the GAP analysis aligns two sequences over their entire length.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In a further embodiment, the present invention relates to polynucleotides which are substantially identical to those specifically described herein. As used herein, with reference to a polynucleotide the term "substantially identical" means the substitution of one or a few (for example 2, 3, or 4) nucleotides whilst maintaining at least one activity of the native protein encoded by the polynucleotide. In addition, this term includes the addition or deletion of nucleotides which results in the increase or decrease in size of the encoded native protein by one or a few (for example 2, 3, or 4) amino acids whilst maintaining at least one activity of the native protein encoded by the polynucleotide.

The present invention also relates to the use of oligonucleotides, for instance in methods of screening for a polynucleotide of, or encoding a polypeptide of, the invention. As used herein, "oligonucleotides" are polynucleotides up to 50 nucleotides in length. The minimum size of such oligonucleotides is the size required for the formation of a stable hybrid between an oligonucleotide and a complementary sequence on a nucleic acid molecule of the present invention. They can be RNA, DNA, or combinations or derivatives of either. Oligonucleotides are typically relatively short single stranded molecules of 10 to 30 nucleotides, commonly 15-25 nucleotides in length. When used as a guide for genome editing, probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, more preferably at least 22 nucleotides, even more preferably at least 25 nucleotides in length. Oligonucleotides of the present invention used as a probe are typically conjugated with a label such as a radioisotope, an enzyme, biotin, a fluorescent molecule or a chemiluminescent molecule. Examples of oligonucleotides of the invention include those provided in SEQ ID NO's 45 and 46.

As those skilled in the art would be aware, the sequence of the oligonucleotide primers described herein can be varied to some degree without effecting their usefulness for the methods of the invention. A "variant" of an oligonucleotide disclosed herein (also referred to herein as a "primer" or "probe" depending on its use) useful for the methods of the invention includes molecules of varying sizes of, and/or are capable of hybridising to the genome close to that of, the specific oligonucleotide molecules defined herein. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise the target region. In addition, variants may readily be designed which hybridise close (for example, but not limited to, within 50 nucleotides or within 100 nucleotides) to the region of the genome where the specific oligonucleotides defined herein hybridise.

The present invention includes oligonucleotides that can be used as, for example, guides for RNA-guided endonucleases, probes to identify nucleic acid molecules, or primers to produce nucleic acid molecules. Probes and/or primers can be used to clone homologues of the polynucleotides of the invention from other species. Furthermore, hybridization techniques known in the art can also be used to screen genomic or cDNA libraries for such homologues.

Polynucleotides and oligonucleotides of the present invention include those which hybridize under stringent conditions to one or more of the sequences provided as SEQ ID NO: 2 and/or SEQ ID NO:22. As used herein, stringent conditions are those that (1) employ low ionic strength and high temperature for washing, for example, 0.015 M NaCl/0.0015 M sodium citrate/0.1% $NaDodSO_4$ at 50° C.: (2) employ during hybridisation a denaturing agent such as formamide, for example, 50% (vol/vol) formamide with 0.1% bovine serum albumin, 0.1% Ficoll, 0.1% polyvinylpyrrolidone. 50 mM sodium phosphate buffer at pH 6.5 with 750 mM NaCl, 75 mM sodium citrate at 42° C.; or (3) employ 50% formamide. 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid). A variant of a polynucleotide or an oligonucleotide of the invention includes molecules of varying sizes of, and/or are capable of hybridising to, the wheat genome close to that of the reference polynucleotide or oligonucleotide molecules defined herein. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise to the target region. In addition, variants may readily be designed which hybridise close to, for example to within 50 nucleotides, the region of the plant genome where the specific oligonucleotides defined herein hybridise. In particular, this includes polynucleotides which encode the same polypeptide or amino acid sequence but which vary in nucleotide sequence by redundancy of the genetic code. The terms "polynucleotide variant" and "variant" also include naturally occurring allelic variants.

Nucleic Acid Constructs

The present invention includes nucleic acid constructs comprising the polynucleotides of the invention, and vectors and host cells containing these, methods of their production and use, and uses thereof. The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In preferred embodiments of the present invention, the cis-acting sequence is an activator sequence that enhances or stimulates the expression of an expressible genetic sequence. "Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide which is approximately the same as the distance between that promoter and the protein coding region it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting, i.e., the genes from which it is derived.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, such as a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of an organism such as a plant. The term constitutive as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of, for example, the plant, such as, for example, endosperm, embryo, leaves, fruit, tubers or root. In a preferred embodiment, a promoter is expressed selectively or preferentially in leaves and/or stems of a plant, preferably a cereal plant. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages such as adults or seedlings. Compartmentation in specific subcellular locations such as the plastid, cytosol, vacuole, or apoplastic space may be achieved by the inclusion in the structure of the gene product of appropriate signals, e.g. a signal peptide, for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in, for example, a plant. Typically, the promoter is expressed at a level 10-fold higher in the specific tissue or organ than in other tissues or organs.

In an embodiment, the promoter is a stem-specific promoter, a leaf-specific promoter or a promoter which directs gene expression in an aerial part of the plant (at least stems and leaves) (green tissue specific promoter) such as a ribulose-1,5-bisphosphate carboxylase oxygenase (RUBISCO) promoter.

Examples of stem-specific promoters include, but are not limited to those described in U.S. Pat. No. 5,625,136, and Bam et al. (2008).

The promoters contemplated by the present invention may be native to the host plant to be transformed or may be derived from an alternative source, where the region is functional in the host plant. Other sources include the *Agrobacterium* T-DNA genes, such as the promoters of genes for the biosynthesis of nopaline, octapine, mannopine, or other opine promoters, tissue specific promoters (see, e.g., U.S. Pat. No. 5,459,252 and WO 91/13992); promoters from viruses (including host specific viruses), or partially or wholly synthetic promoters. Numerous promoters that are functional in mono- and dicotyledonous plants are well known in the art (see, for example, Greve, 1983: Salomon et al., 1984; Garfinkel et al., 1983; Barker et al., 1983); including various promoters isolated from plants and viruses such as the cauliflower mosaic virus promoter (CaMV 35S, 19S). Non-limiting methods for assessing promoter activity are disclosed by Medberry et al. (1992, 1993), Sambrook et al. (1989, supra) and U.S. Pat. No. 5,164,316.

Alternatively, or additionally, the promoter may be an inducible promoter or a developmentally regulated promoter which is capable of driving expression of the introduced polynucleotide at an appropriate developmental stage of the, for example, plant. Other cis-acting sequences which may be employed include transcriptional and/or translational enhancers. Enhancer regions are well known to persons skilled in the art, and can include an ATG translational initiation codon and adjacent sequences. When included, the initiation codon should be in phase with the reading frame of the coding sequence relating to the foreign or exogenous polynucleotide to ensure translation of the entire sequence if it is to be translated. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

The nucleic acid construct of the present invention may comprise a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal functions for addition of polyadenylic acid tracts to the 3' end of a mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from an octopine synthase (ocs) gene or nopaline synthase (nos) gene of Agrobacteritun tumelaciens (Bevan et al., 1983). Suitable 3' non-translated sequences may also be derived from plant genes such as the ribulose-1,5-bisphosphate carboxylase (ssRUBISCO) gene, although other 3' elements known to those of skill in the art can also be employed.

As the DNA sequence inserted between the transcription initiation site and the start of the coding sequence, i.e., the untranslated 5' leader sequence (5'UTR), can influence gene expression if it is translated as well as transcribed, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi (1987).

Vectors

The present invention includes use of vectors for manipulation or transfer of genetic constructs. By "chimeric vector" is meant a nucleic acid molecule, preferably a DNA molecule derived, for example, from a plasmid, bacteriophage, or plant virus, into which a nucleic acid sequence may be inserted or cloned. A vector preferably is double-stranded DNA and contains one or more unique restriction sites and may be capable of autonomous replication in a defined host cell including a target cell or tissue or a progenitor cell or tissue thereof, or capable of integration into the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, e.g., pUC-derived vectors, pSK-derived vectors. pGEM-derived vectors, pSP-derived vectors, pBS-derived vectors, or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hvg gene which encodes hygromycin B resistance; a neomvcin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327, an acetyltransferase gene from Sireptomyces *viridochromogenes* conferring resistance to the selective agent phosphinothricin as, for example, described in EP 275957, a gene encoding a 5-enolshikimate-3-phosphate synthase (EPSPS) conferring tolerance to N-phosphonomethylglycine as, for example, described by Hinchee et al. (1988), a bar gene conferring resistance against bialaphos as, for example, described in WO91/02071; a nitrilase gene such as bxn from *Klebsiella* ozaenae which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imida.olinone, sulfonylurea or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a 0-glucuronidase (GUS) enzyme for which various chromogenic substrates are known, a 0-galactosidase gene encoding an enzyme for which chromogenic substrates are known, an aequorin gene (Prasher et al., 1985), which may be employed in calcium-sensitive bioluminescence detection; a green fluorescent protein gene (Niedz et al., 1995) or derivatives thereof; a luciferase (luc) gene (Ow et al., 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Preferably, the nucleic acid construct is stably incorporated into the genome of, for example, the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes a recombinant vector, which includes at least one polynucleotide molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaiyotic or eukaryotic, and typically is a virus or a plasmid.

A number of vectors suitable for stable transfection of plant cells or for the establishment of transgenic plants have been described in, e.g., Pouwels et al., Cloning Vectors: A Laboratory Manual, 1985, supp. 1987, Weissbach and Weissbach, Methods for Plant Molecular Biology, Academic Press. 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

The level of a protein of the invention may be modulated by increasing the level of expression of a nucleotide sequence that codes for the protein in a plant cell, or decreasing the level of expression of a gene encoding the protein in the plant, leading to modified pathogen resistance. The level of expression of a gene may be modulated by altering the copy number per cell, for example by introducing a synthetic genetic construct comprising the coding sequence and a transcriptional control element that is operably connected thereto and that is functional in the cell. A plurality of transformants may be selected and screened for those with a favourable level and/or specificity of transgene expression arising from influences of endogenous sequences in the vicinity of the transgene integration site. A favourable level and pattern of transgene expression is one which results in a substantial modification of pathogen resistance or other phenotype. Alternatively, a population of mutagenized seed or a population of plants from a breeding program may be screened for individual lines with altered pathogen resistance or other phenotype associated with pathogen resistance.

Recombinant Cells

Another embodiment of the present invention includes a recombinant cell comprising a host cell transformed with one or more recombinant molecules of the present invention, or progeny cells thereof. Transformation of a nucleic acid molecule into a cell can be accomplished by any method by which a nucleic acid molecule can be inserted into the cell. Transformation techniques include, but are not limited to, transfection, particle bombardment/biolistics, electroporation, microinjection, lipofection, adsorption, and protoplast fusion. In an embodiment, gene editing is used to transform the target cell using, for example, targeting nucleases such as TALEN, Cpf1 or Cas9-CRISPR or engineered nucleases derived therefrom.

A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred host cells are plant cells, more preferably cells of a cereal plant, more preferably barley or wheat cells, and even more preferably a wheat cell.

Genome Editing

Endonucleases can be used to generate single strand or double strand breaks in genomic DNA. The genomic DNA breaks in eukarvotic cells are repaired using non-homologous end joining (NHEJ) or homology directed repair (HDR) pathways. NHEJ may result in imperfect repair resulting in unwanted mutations and HDR can enable precise gene insertion by using an exogenous supplied repair DNA template. CRISPR-associated (Cas) proteins have received significant interest although transcription activator-like effector nucleases (TALENs) and zinc-finger nucleases are still useful, the CRISPR-Cas system offers a simpler, versatile and cheaper tool for genome modification (Doudna and Charpentier, 2014).

The CRISPR-Cas systems are classed into three major groups using various nucleases or combinations on nuclease. In class 1 CRISPR-Cas systems (types I, III and IV), the effector module consists of a multi-protein complex whereas class 2 systems (types 11, V and VI) use only one effector protein (Makarova et al., 2015). Cas includes a gene that is coupled or close to or localised near the flanking CRISPR loci. Haft et al. (2005) provides a review of the Cas protein family.

The nuclease is guided by the synthetic small guide RNA (sgRNAs or gRNAs) that may or may not include the tracRNA resulting in a simplification of the CRISPR-Cas system to two genes; the endonuclease and the sgRNA (Jinek et al. 2012). The sgRNA is typically under the regulatory control of a U3 or U6 small nuclear RNA promoter. The sgRNA recognises the specific gene and part of the gene for targeting. The protospacer adjacent motif (PAM) is adjacent to the target site constraining the number of potential CRISPR-Cas targets in a genome although the expansion of nucleases also increases the number of PAM's available. There are numerous web tools available for designing gRNAs including CHOPCHOP (http://chopchop.cbu.uib.no), CRISPR design https://omictools.com/crispr-design-tool, E-CRISP http://www.e-crisp.org/E-CRISP/, Geneious or Benchling https://benchling.com/crispr.

CRISPR-Cas systems are the most frequently adopted in eukaryotic work to date using a Cas9 effector protein typically using the RNA-guided *Streptococcus pyogenes* Cas9 or an optimised sequence variant in multiple plant species (Luo et al., 2016). Luo et al. (2016) summarises numerous studies where genes have been successfully targeted in various plant species to give rise to indels and loss of function mutant phenotypes in the endogenous gene open reading frame and/or promoter. Due to the cell wall on plant cells the delivery of the CRISPR-Cas machinery into the cell and successful transgenic regenerations have used *Agrobacterium tumefaciens* infection (Luo et al., 2016) or plasmid DNA particle bombardment or biolistic delivery. Vectors suitable for cereal transformation include pCXUNcas9 (Sun et al, 2016) or pYLCRISPR/Cas9Pubi-H available from Addgene (Ma et al., 2015, accession number KR029109.1).

Alternative CRISPR-Cas systems refer to effector enzymes that contain the nuclease RuvC domain but do not contain the HNH domain including Casl2 enzymes including Casl2a, Casl2b, Casl2f, Cpf1. C2c1, C2c3, and engineered derivatives. Cpf1 creates double-stranded breaks in a staggered manner at the PAM-distal position and being a smaller endonuclease may provide advantages for certain species (Begemann et al., 2017). Other CRISPR-Cas systems include RNA-guided RNAses including Cas13. Cas13a (C2c2), Cas13b, Casl3c.

Sequence Insertion or Integration

The CRISPR-Cas system can be combined with the provision of a nucleic acid sequence to direct homologous repair for the insertion of a sequence into a genome. Targeted genome integration of plant transgenes enables the sequential addition of transgenes at the same locus. This "cis gene stacking" would greatly simplify subsequent breeding efforts with all transgenes inherited as a single locus. When coupled with CRISPR/Cas9 cleavage of the target site the transgene can be incorporated into this locus by homology-directed repair that is facilitated by flanking sequence homology. This approach can be used to rapidly introduce new alleles without linkage drag or to introduce allelic variants that do not exist naturally.

Nickases

The CRISPR-Cas II systems use a Cas9 nuclease with two enzymatic cleavage domains a RuvC and HNH domain. Mutations have been shown to alter the double strand cutting to single strand cutting and resulting in a technology variant referred to as a nickase or a nuclease-inactivated Cas9. The RuvC subdomain cleaves the non-complementary DNA strand and the HNH subdomain cleaves that DNA strand complementary to the gRNA. The nickase or nuclease-inactivated Cas9 retains DNA binding ability directed by the gRNA. Mutations in the subdomains are known in the art for example Spyogenes Cas9 nuclease with a DI0A mutation or H840A mutation.

Genome Base Editing or Modification

Base editors have been created by fusing a deaminase with a Cas9 domain (WO 2018/086623). By fusing the deaminase can take advantage of the sequence targeting directed by the gRNA to make targeted cytidine (C) to uracil (U) conversion by deamination of the cytidine in the DNA. The mismatch repair mechanisms of the cell then replace the U with a T. Suitable cytidine deaminases may include APOBEC1 deaminase, activation-induced cytidine deaminase (AID), APOBEC3G and CDAL. Further, the Cas9-deaminase fusion may be a mutated Cas9 with nickase activity to generate a single strand break. It has been suggested that the nickase protein was potentially more efficient in promoting homology-directed repair (Luo et al., 2016).

Vector Free Genome Fditing or Genume Modification

More recently methods to use vector free approaches using Cas9/sgRNA ribonucleoproteins have been described with successful reduction of off-target events. The method requires in vitro expression of Cas9 ribonucleoproteins (RNPs) which are transformed into the cell or protoplast and does not rely on the Cas9 being integrated into the host genome, thereby reducing the undesirable side cuts that has been linked with the random integration of the Cas9 gene. Only short flanking sequences are required to form a stable Cas9 and sgRNA stable ribonucleoprotein in vitro. Woo et al. (2015) produced pre-assembled Cas9/sgRNA protein/RNA complexes and introduced them into protoplasts ofArabidopsis, rice, lettuce and tobacco and targeted mutagenesis frequencies of up to 45% observed in regenerated plants. RNP and in vitro demonstrated in several species including dicot plants (Woo et al., 2015), and monocots maize (Svitashev et al., 2016) and wheat (Liang et al., 2017). Genome editing of plants using CRISPR-Cas 9 in vitro transcripts or ribonucleoproteins are fully described in Liang et al. (2018) and Liang et al. (2019).

Method for Gene Insertion

Plant embryos may be bombarded with a Cas9 gene and sgRNA gene targeting the site of integration along with the DNA repair template. DNA repair templates are may be synthesised DNA fragment or a 127-mer oligonucleotide, with each encoding the cDNA or the gene of interest. Bombarded cells are grown on tissue culture medium. DNA extracted from callus or TO plants leaf tissue using CTAB DNA extraction method can be analysed by PCR to confirm gene integration. TI plants selected if pcr confirms presence of the gene of interest.

The method comprises introducing into a plant cell the DNA sequence of interest referred to as the donor DNA and the endonuclease. The endonuclease generates a break in the target site allowing the first and second regions of homology of the donor DNA to undergo homologous recombination with their corresponding genomic regions of homology. The cut genomic DNA acts as an acceptor of the DNA sequence. The resulting exchange of DNA between the donor and the genome results in the integration of the polynucleotide of interest of the donor DNA into the strand break in the target site in the plant genome, thereby altering the original target site and producing an altered genomic sequence.

The donor DNA may be introduced by any means known in the art. For example, a plant having a target site is provided. The donor DNA may be provided to the plant by known transformation methods including. *Agrobacterium*-mediated transformation or biolistic particle bombardment. The RNA guided Cas or Cpf1 endonuclease cleaves at the target site, the donor DNA is inserted into the transformed plant's genome.

Although homologous recombination occurs at low frequency in plant somatic cells the process appears to be increased/stimulated by the introduction of doublestrand breaks (DSBs) at selected endonuclease target sites. Ongoing efforts to generate Cas, in particular Cas9, variants or alternatives such as Cpf1 or Cmsl may improve the efficiency.

Transgenic Plants

The term "plant" as used herein as a noun refers to whole plants and refers to any member of the Kingdom Plantae, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, cotyledons, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are cotyledon, embryo and embryo axis. The invention accordingly includes plants and plant parts and products comprising these.

As used herein, the term "seed" refers to "mature seed" of a plant, which is either ready for harvesting or has been harvested from the plant, such as is typically harvested commercially in the field, or as "developing seed" which occurs in a plant after fertilisation and prior to seed dormancy being established and before harvest.

A "transgenic plant" as used herein refers to a plant that contains a nucleic acid construct not found in a wild-type plant of the same species, variety or cultivar. That is, transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants".

A "non-transgenic plant" is one which has not been genetically modified by the introduction of genetic material by human intervention using, for example, recombinant DNA techniques. In a preferred embodiment, the transgenic plants are homozygous for each and every gene that has been introduced (transgene) so that their progeny do not segregate for the desired phenotype.

As used herein, the term "compared to an isogenic plant", or similar phrases, refers to a plant which is isogenic relative to the transgenic plant but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein.

Transgenic plants, as defined in the context of the present invention include progeny of the plants which have been genetically modified using recombinant techniques, wherein the progeny comprise the transgene of interest. Such progeny may be obtained by self-fertilization of the primary transgenic plant or by crossing such plants with another plant of the same species. This would generally be to modulate the production of at least one protein defined herein in the desired plant or plant organ. Transgenic plant parts include all parts and cells of said plants comprising the transgene such as, for example, cultured tissues, callus and protoplasts.

Plants contemplated for use in the practice of the present invention include both monocotyledons and dicotyledons. Target plants include, but are not limited to, the following: cereals (for example, wheat, barley, rye, oats, rice, maize, sorghum and related crops): grapes; beet (sugar beet and fodder beet); pomes, stone fruit and soft fruit (apples, pears, plums, peaches, almonds, chernes, strawberries, raspberries and black-berries): leguminous plants (beans, lentils, peas, soybeans); oil plants (rape or other Brassicas, mustard, poppy, olives, sunflowers, safflower, flax, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor): or plants such as maize, tobacco, nuts, coffee, sugar cane, tea, vines, hops, turf, bananas and natural rubber plants, as well as ornamentals (flowers, shrubs, broad-leaved trees and evergreens, such as conifers). Preferably, the plant is a cereal plant, more preferably wheat, rice, maize, triticale, oats or barley, even more preferably wheat.

As used herein, the term "wheat" refers to any species of the Genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T compactum, T*

*sphaerococcum, T vavdovii*, and interspecies cross thereof. A preferred species of hexaploid wheat is *T aestivum* ssp *aestivum* (also termed "breadwheat"). Tetraploid wheat includes *T. durum* (also referred to herein as durum wheat or *Triticum turgidum* ssp. durum), *T. dicoccoides*, T. *dicoccum, T polonicum*, and interspecies cross thereof. In addition, the term "wheat" includes potential progenitors of hexaploid or tetraploid *Triticum* sp. such as T. uartu. *T monococcum* or *T boeoticum* for the A genome, *Aegilops speltoides* for the B genome, and T. *tauschii* (also known as *Aegilops squarrosa* or *Aegilops tauschii*) for the D genome. Particularly preferred progenitors are those of the A genome, even more preferably the A genome progenitor is *T. monococcum*. A wheat cultivar for use in the present invention may belong to, but is not limited to, any of the above-listed species. Also encompassed are plants that are produced by conventional techniques using *Triticum* sp. as a parent in a sexual cross with a non-*Triticum* species (such as rye [*Secale cereale*]), including but not limited to Triticale.

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

Transgenic plants, as defined in the context of the present invention include plants (as well as parts and cells of said plants) and their progeny which have been genetically modified using recombinant techniques to cause production of at least one polypeptide of the present invention in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (20(4).

In a preferred embodiment, the transgenic plants are homozygous for each and every gene that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

As used herein, the "other genetic markers" may be any molecules which are linked to a desired trait of a plant. Such markers are well known to those skilled in the art and include molecular markers linked to genes determining traits such disease resistance, yield, plant morphology, grain quality, dormancy traits, grain colour, gibberellic acid content in the seed, plant height, flour colour and the like. Examples of such genes are the rust resistance genes mentioned herein, the nematode resistance genes such as Cre1 and Cre3, alleles at glutenin loci that determine dough strength such as Ax, Bx, Dx, Ay, By and Dhy alleles, the Rht genes that determine a semi-dwarf growth habit and therefore lodging resistance.

Four general methods for direct delivery of a gene into cells have been described. (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. Nos. 4,945,050 and 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press. Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. A particle delivery system suitable for use with the present invention is the helium acceleration PDS-1000/He gun is available from Bio-Rad Laboratories. For the bombardment, immature embryos or derived target cells such as scutella or calli from immature embryos may be arranged on solid culture medium.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat Nos. 5, 451.513, 5,545,818, 5,877,402, 5,932,479, and WO 99/05265.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. Nos. 5,177,010, 5,104,310, 5,004,863, 5,159,135). Further, the integration of the T-DNA is a relatively precise process resulting in few rearrangements. The region of DNA to be transferred is defined by the border sequences, and intervening DNA is usually inserted into the plant genome.

*Agrobacterium* transformation vectors are capable of replication in *E. coli* as well as *Agrobacterium*, allowing for convenient manipulations as described (Klee et al., Plant DNA Infectious Agents, Hohn and Schell, (editors), Springer-Verlag. New York, (1985): 179-203). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, Agrobacteriiun containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated/crossed to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, Breeding Methods for Cultivar Development, J. Wilcox (editor) American Society of Agronomy. Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985: Toriyama et al., 1986, Abdullah et al., 1986).

Other methods of cell transformation can also be used and include but are not limited to introduction of polynucleotides such as DNA into plants by direct transfer into pollen, by direct injection of polynucleotides such as DNA into reproductive organs of a plant, or by direct injection of polynucleotides such as DNA into the cells of immature embryos followed by the rehydration of desiccated embryos.

The regeneration, development, and cultivation of plants from single plant protoplast transformants or from various transformed explants is well known in the art (Weissbach et al., Methods for Plant Molecular Biology, Academic Press, San Diego, (1988)). This regeneration and growth process ty pically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. Pat. Nos. 5,004,863, 5,159,135, 5,518,908): soybean (US 5,569,834, 5,416,011): *Brassica* (US 5,463,174); peanut (Cheng et al., 1996); and pea (Grant et al., 1995).

Methods for transformation of cereal plants such as wheat and barley for introducing genetic variation into the plant by introduction of an exogenous nucleic acid and for regeneration of plants from protoplasts or immature plant embryos are well known in the art, see for example, CA 2,092,588, AU 61781/94, AU 667939, US 6,100,447. WO 97/048814, US 5,589,617, US 6,541,257, and other methods are set out in WO 99/14314. Preferably, transgenic wheat or barley plants are produced by Agrobacteriun *tumefaciens* mediated transformation procedures. Vectors carrying the desired nucleic acid construct may be introduced into regenerable wheat cells of tissue cultured plants or explants, or suitable plant systems such as protoplasts. The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Marker Assisted Selection

Marker assisted selection is a well recognised method of selecting for heterozygous plants required when backcrossing with a recurrent parent in a classical breeding program. The population of plants in each backcross generation will be heterozygous for the gene of interest normally present in a 1.1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants. To further speed up the backcrossing program, the embryo from immature seeds (25 days post anthesis) may be excised and grown up on nutrient media under sterile conditions, rather than allowing full seed maturity. This process, termed "embryo rescue", used in combination with DNA extraction at the three leaf stage and analysis of at least one Sr61 allele or variant that confers upon the plant resistance to at least one strain of *Puccinia graminis*, allows rapid selection of plants carrying the desired trait, which may be nurtured to maturity in the greenhouse or field for subsequent further backcrossing to the recurrent parent.

Any molecular biological technique known in the art can be used in the methods of the present invention. Such methods include, but are not limited to, the use of nucleic acid amplification, nucleic acid sequencing, nucleic acid hybridization with suitably labelled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, 2000: Langridge et al., 2001). The invention also includes the use of molecular marker techniques to detect polymorphisms linked to alleles of the (for example) Sr6 gene which confers upon the plant resistance to at least one strain of *Puccinia graminis*. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al., (2001).

In an embodiment, a linked loci for marker assisted selection is at least within 1cM, or 0.5cM, or 0.1cM, or 0.01cM from a gene encoding a polypeptide of the invention.

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (M.J. McPherson and S.G Moller (editors), BIOS Scientific Publishers Ltd, Oxford, (2000)). PCR can be performed on cDNA obtained from reverse transcribing mRNA isolated from plant cells expressing a Sr61 gene or allele which confers upon the plant resistance to at least one strain of *Puccinia graminis*. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al., (.supra) and Sambrook et al., (supra). Sequencing can be carried out by any suitable method, for example, dideoxy sequencing, chemical sequencing or variations thereof. Direct sequencing has the advantage of determining variation in any base pair of a particular sequence.

Tilling

Plants of the invention can be produced using the process known as TILLING (Targeting Induced Local Lesions IN Genomes). In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs.

Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and % lanes per assay, this combination allows up to a million base pairs of genomic DNA to be screened per single assay, making TILLING a high-throughput technique.

TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background pattems are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Plant/Grain Processing

Grain/seed of the invention, preferably cereal grain and more preferably wheat grain, or other plant parts of the invention, can be processed to produce a food ingredient, food or non-food product using any technique known in the art.

In one embodiment, the product is whole grain flour such as, for example, an ultrafine-milled whole grain flour, or a flour made from about 100% of the grain. The whole grain flour includes a refined flour constituent (refined flour or refined flour) and a coarse fraction (an ultrafine-milled coarse fraction).

Refined flour may be flour which is prepared, for example, by grinding and bolting cleaned grain such as wheat or barley grain. The particle size of refined flour is described as flour in which not less than 98% passes through a cloth having openings not larger than those of woven wire cloth designated "212 micrometers (U.S. Wire 70)". The coarse fraction includes at least one of: bran and germ. For instance, the germ is an embryonic plant found within the grain kernel. The germ includes lipids. fiber, vitamins, protein, minerals and phytonutnents, such as flavonoids. The bran includes several cell layers and has a significant amount of lipids, fiber, vitamins. protein, minerals and phytonutrients, such as flavonoids. Further, the coarse fraction may include an aleurone layer which also includes lipids, fiber, vitamins, protein, minerals and phytonutrients, such as flavonoids. The aleurone layer, while technically considered part of the endosperm, exhibits many of the same characteristics as the bran and therefore is typically removed with the bran and germ during the milling process. The aleurone layer contains proteins, vitamins and phytonutrients, such as ferulic acid.

Further, the coarse fraction may be blended with the refined flour constituent. The coarse fraction may be mixed with the refined flour constituent to form the whole grain flour, thus providing a whole grain flour with increased nutritional value, fiber content, and antioxidant capacity as compared to refined flour. For example, the coarse fraction or whole grain flour may be used in various amounts to replace refined or whole grain flour in baked goods, snack products, and food products. The whole grain flour of the present invention (i.e.-ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In further embodiments, enzymes found within the bran and germ of the whole grain flour and/or coarse fraction are inactivated in order to stabilize the whole grain flour and/or coarse fraction. Stabilization is a process that uses steam, heat, radiation, or other treatments to inactivate the enzymes found in the bran and germ layer. Flour that has been stabilized retains its cooking characteristics and has a longer shelf life.

In additional embodiments, the whole grain flour, the coarse fraction, or the refined flour may be a component (ingredient) of a food product and may be used to product a food product. For example, the food product may be a bagel, a biscuit, a bread, a bun, a croissant, a dumpling, an English muffin, a muffin, a pita bread, a quickbread, a refrigerated/frozen dough product, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In alternative embodiments, the whole grain flour, refined flour, or coarse fraction may be a component of a nutritional supplement. For instance, the nutritional supplement may be a product that is added to the diet containing one or more additional ingredients, typically including: vitamins, minerals, herbs, amino acids, enzymes, antioxidants, herbs, spices, probiotics, extracts, prebiotics and fiber. The whole grain flour, refined flour or coarse fraction of the present invention includes vitamins, minerals, amino acids, enzymes, and fiber. For instance, the coarse fraction contains a concentrated amount of dietary fiber as well as other essential nutrients, such as B-vitamins, selenium, chromium, manganese, magnesium, and antioxidants, which are essential for a healthy diet. For example 22 grams of the coarse fraction of the present invention delivers 33% of an individual's daily recommend consumption of fiber. The nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients. The supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage, this embodiment may be particularly attractive as a fiber supplement for children.

In an additional embodiment, a milling process may be used to make a multi-grain flour or a multi-grain coarse fraction. For example, bran and germ from one type of grain may be ground and blended with ground endosperm or whole grain cereal flour of another type of cereal. Alternatively, bran and germ of one type of grain may be ground and blended with ground endosperm or whole grain flour of another type of grain. It is contemplated that the present invention encompasses mixing any combination of one or more of bran, germ, endosperm, and whole grain flour of one or more grains. This multi-grain approach may be used to make custom flour and capitalize on the qualities and nutritional contents of multiple types of cereal grains to make one flour.

It is contemplated that the whole grain flour, coarse fraction and/or grain products of the present invention may be produced by any milling process known in the art. An exemplary embodiment involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like. After grinding, the grain is discharged and conveyed to a sifter. Further, it is contemplated that the whole grain flour, coarse fraction and/or grain products of the present invention may be modified or enhanced by way of numerous other processes such as: fermentation, instantizing, extrusion, encapsulation, toasting, roasting, or the like.

Malting

A malt-based beverage provided by the present invention involves alcohol beverages (including distilled beverages) and non-alcohol beverages that are produced by using malt as a part or whole of their starting material. Examples include beer, happoshu (low-malt beer beverage), whisky, low-alcohol malt-based beverages (e.g., malt-based beverages containing less than 1% of alcohols), and non-alcohol beverages.

Malting is a process of controlled steeping and germination followed by drying of the grain such as barley and wheat grain. This sequence of events is important for the synthesis of numerous enzymes that cause grain modification, a process that principally depolymerizes the dead endosperm cell walls and mobilizes the grain nutrients. In the subsequent drying process, flavour and colour are produced due to chemical browning reactions. Although the primary use of malt is for beverage production, it can also be utilized in other industrial processes, for example as an enzyme source in the baking industry, or as a flavouring and colouring agent in the food industry, for example as malt or as a malt flour, or indirectly as a malt syrup, etc.

In one embodiment, the present invention relates to methods of producing a malt composition. The method preferably comprises the steps of:

(i) providing grain, such as barley or wheat grain, of the invention,
(ii) steeping said grain,
(iii) germinating the steeped grains under predetermined conditions and
(iv) drying said germinated grains.

For example, the malt may be produced by any of the methods described in Hoseney (Principles of Cereal Science and Technology, Second Edition, 1994: American Association of Cereal Chemists, St. Paul, Minn.). However, any other suitable method for producing malt may also be used with the present invention, such as methods for production of speciality malts, including, but limited to, methods of roasting the malt.

Malt is mainly used for brewing beer, but also for the production of distilled spirits. Brewing comprises wort production, main and secondary fermentations and post-treatment. First the malt is milled, stirred into water and heated. During this "mashing", the enzymes activated in the malting degrade the starch of the kernel into fermentable sugars. The produced wort is clarified, yeast is added, the mixture is fermented and a post-treatment is performed.

EXAMPLES

Example 1—Material and Methods

Plant materials, mutaeenesis and mutant DNA preparation Wheat plants carrying Sr26 (Avocet+Lr46) and Sr61 (W3757) were mutagenized with EMS and progeny susceptible to rust strain 34-1,2,3,4,5.6,7 were selected as described in a related study (Zhang et al., 2018). Genomic DNA was prepared from seedling leaves as described by Yu et al. (2017). DNA quality and quantity were assessed with a NanoDrop spectrophotometer and by electrophoresis on 0.8% agarose gels.

R Gene Enrichment and Sequencing (RenSea)

Target enrichment of NLRs was done by Arbor Biosciences (Ann Arbor, MI, USA) following the MYbaits protocol with Triticeae NLR bait library Tv2 for Sr26 and Tv3 for Sr61 available at https://github.com/steuernb/Mutant-Hunter/blob/master/Triticea_RenSec_Baits_V3.fast a.gz. Library construction followed the TruSeq RNA Protocol v2. All enriched libraries were sequenced by a HiSeq 2500 (Illumina) using 250 bp paired-end reads.

Sequence Analysis

CLC Genomics Workbench V9.0 (Sr26) and V10.0 (Sr61) (Qiagen, Hilden, Germany) were used for read quality control (QC), trimming, and de novo assembly of wild-type reads (Minimum contig length: 250; Auto-detect paired distances: Perform scaffolding; Mismatch cost. 2, Insertion cost: 3, Deletion cost: 3, Length fraction from 0.5 to 0.9, similarity fraction from 0.9 to 0.98), and mapping all the reads from both wildtype and mutants against the de novo wild-type assembly (No masking, Linear gap cost, Length fraction from 0.5 to 0.9, similarity fraction from 0.95 to 0.98).

Sr26 contigs containing mutations in each line were identified using the MutantHunter8 pipeline with default parameters. For Sr61 analysis the M1 mutant was used for de novo assembly due to insufficient data obtained from the wildtype (W3757). The MuTrigo Python package (https://github.comfrC-Hewitt/MuTrigo) was used for SNP calling with default parameters to identify candidate contigs containing mutations in the Sr61 mutants.

Gene Sequence Assembly and Structure Confirmation

Total RNA was extracted using a PureLink™ RNA Mini Kit (Invitrogen, Carlsbad, California, USA) as per the manufacturer's instructions. cDNA synthesis was performed as described by Clontech. Flanking gene sequences were amplified by 5' and 3' RACE (rapid amplification of cDNA ends) (Takara Bio, California, USA) and by using a Universal GenomeWalker (Takara Bio, California, USA). Nonsynomous substitutions identified in mutants by RenSeq were confirmed with Sanger sequencing. Exon-intron structures were confirmed by cDNA amplification and sequencing.

Transgenic Validation

Sr26 was introduced into wheat cultivar Fielder using binary vector pVecBARII and the *Agrobacterium*-transformation protocol (Ishida et al., 2015) with phosphinothricin as a selective agent. TO shoots were transplanted to growth cabinet (23° C., 16 h light). Plants were inoculated with Pgt races 98-1,2,(3),(5),6 at 7-10 days post transplantation and rust reactions were assessed after 10-15 days (McIntosh et al., 1995).

Sr61 was introduced into wheat cultivar Fielder using binary vector pVecBARII and the Agrohacterium-transformation protocol (Ishida et al., 2015) with phosphinothricin as a selective agent. To explants were transplanted to a growth cabinet (23° C., 16 h light!8 h darkness). Plants were inoculated with Pgt race 98-1,2,(3),(5),6 at 7-10 days post transplantation and rust reactions were assessed after 10-15 days (McIntosh et al., 1995).

Rust Phenotyping and Histological Assessment

Stem rust phenotyping of seedlings and adult plants in the greenhouse and field was as previously described (Pretorius et al., 2015; Bender et al., 2016). The experiments carried out at Global Rust Reference Center (GRRC), Denmark were done in quarantine greenhouse. Microscopic histological assessments were used to determine representative infection site sizes as described by Ayliffe et al. (2013). Microscopic images were photographed using a CC12 digital camera and AnalySIS LS Research version 2.2 software (Olympus Soft Imaging System, Japan).

Phylogenetic Tree Construction

R gene protein sequences from the NCBI database (protein accession numbers are listed in Table 2) were aligned using MUSCLE and phylogenetic trees were constructed using UPGMA in Mega735. The evolutionary history was inferred using the Neighbor-Joining method36. The tree is drawn to scale, with branch lengths in the same units as those of the evolutionar, distances used to infer the phylogenetic tree.

The evolutionary distances were computed using the Poisson correction method and are in the units of the number of amino acid substitutions per site. All positions containing gaps and missing data were eliminated. Final phylogenetic trees were annotated by ITOL (https://itol.embl.de).

TABLE 2

R gene protein sequences from the NCBI database.

| No. | Protein accession no. | R gene | Type |
|---|---|---|---|
| 1 | AAC49408 | Prf | CNL |
| 2 | AAC97933 | Mi-1 | CNL |
| 3 | AAF36987 | Hrt1 | CNL |
| 4 | AAF42831.1 | RPP13-Rld-2 | CNL |
| 5 | AAF42832.1 | RPP13-Nd-l | CNL |
| 6 | AAG31014 | Sw-5b | CNL |
| 7 | AAG37354 | Mla1 | CNL |
| 8 | AAO16014 | Mla13 | CNL |
| 9 | AAO43441 | Mla12 | CNL |
| 10 | AAQ10735 | Tm-2 | CNL |
| 11 | AAQ10736 | Tm-$2^2$ | CNL |
| 12 | AAQ55540 | Mla7 | CNL |
| 13 | AAQ55541 | Mla10 | CNL |
| 14 | AAQ96158 | Pm3b | CNL |
| 15 | AAR19096 | Rpg1-b | CNL |
| 16 | AAS49213 | 3gG2 | CNL |
| 17 | AAS79233 | Rp3 | CNL |
| 18 | AAT08955 | Ha-NTIR11g | CNL |
| 19 | AAW48299 | R3a | CNL |
| 20 | AAX31149 | Rxo1 | CNL |
| 21 | AAX89382 | Rps1k-1 and/or Rps1k-2 | CNL |
| 22 | AAY21626 | Pm3a | CNL |
| 23 | AAY21627 | Pm3d | CNL |
| 24 | AAY33493.1 | Pi54 (Syn. Pik-k(h)) | CNL |
| 25 | AAZ23113 | Pm3f | CNL |
| 26 | AAZ95005 | Rpi-blb2 | CNL |
| 27 | ABB78077.1 | Pm3c | CNL |
| 28 | ABB78078.1 | Pm3e | CNL |
| 29 | ABB78079.1 | Pm3g | CNL |
| 30 | ABB88855 | Pi9 | CNL |
| 31 | ABB91438 | Fom-2 | CNL |
| 32 | ABC73398 | Piz-t | CNL |
| 33 | ABC94599 | Pi2 | CNL |
| 34 | ABE68835 | CaMi | CNL |
| 35 | ABS29034 | Lr1 | CNL |
| 36 | ABY58665.1 | Pm3k | CNL |
| 37 | ACB72455 | Pc | CNL |
| 38 | ACI25288.1 | Rpi-sto1 | CNL |
| 39 | ACI25289.1 | Rpi-pta1 | CNL |
| 40 | ACJ66594 | Rpi-vnt1.1 | CNL |
| 41 | ACJ66595.1 | Rpi-vnt1.2 | CNL |
| 42 | ACJ66596 | Rpi-vnt1.3 (Syn. Rpi-phu1) | CNL |
| 43 | ACN56757.1 | RPP13-UKID80 | CNL |
| 44 | ACN56765.1 | RPP13-UKID36 | CNL |
| 45 | ACN56766.1 | RPP13-UKID34 | CNL |
| 46 | ACN56776.1 | RPP13-UKID5 | CNL |
| 47 | ACN79513 | Pid3 | CNL |
| 48 | ACU65454 | R2-like | CNL |
| 49 | ACU65455 | Rpi-abpt | CNL |
| 50 | ACU65456 | R2 | CNL |
| 51 | ACU65457 | Rpi-blb3 | CNL |
| 52 | ACZ65484 | Mla2 | CNL |
| 53 | ACZ65485 | Mla3 | CNL |
| 54 | ACZ65486 | Mla8 | CNL |
| 55 | ACZ65487 | Mla9 | CNL |
| 56 | ACZ65490 | Mla18-2 | CNL |
| 57 | ACZ65492 | Mla22 | CNL |
| 58 | ACZ65493 | Mla23 | CNL |
| 59 | ACZ65495 | Mla27-1 | CNL |
| 60 | ACZ65496 | Mla27-2 | CNL |
| 61 | ACZ65497 | Mla28 | CNL |
| 62 | ACZ65500 | Mla32 | CNL |
| 63 | ACZ65501 | Mla34 | CNL |
| 64 | ACZ65502 | Mla35-1 | CNL |
| 65 | ADB07392 | Bph14 | CNL |
| 66 | ADF29624 | Pi36 | CNL |
| 67 | ADK47521 | Rdg2a | CNL |
| 68 | ADU57957 | CYR1 | CNL |
| 69 | ADX06722 | TmMLA1 | CNL |
| 70 | AEC47890 | R3b | CNL |
| 71 | AER13157 | Rpp4C4 | CNL |
| 72 | AFM35701 | Pi25 | CNL |
| 73 | AGI99538 | RSG3-301 | CNL |
| 74 | AGT37271 | RPP7 | CNL |

TABLE 2-continued

R gene protein sequences from the NCBI database.

| No. | Protein accession no. | R gene | Type |
|---|---|---|---|
| 75 | AIB02970 | Ph-3 | CNL |
| 76 | AIC32313 | Rpg1r | CNL |
| 77 | AIU36098 | VAT | CNL |
| 78 | AKS24975.1 | Pi50 | CNL |
| 79 | AMY98955 | Rpi-amr3i | CNL |
| 80 | ANJ02805 | R8 (Syn. Rpi-smira2) | CNL |
| 81 | ANZ78204 | Pvr4 | CNL |
| 82 | AOR08328 | Tsw | CNL |
| 83 | APF29096 | PigmR (Syn. PigmR6) | CNL |
| 84 | ARO38245.1 | Lr22a | CNL |
| 85 | BAA76282 | Pib | CNL |
| 86 | BAC67706 | Rcy1 | CNL |
| 87 | BAH20862 | Pit | CNL |
| 88 | BAJ25849 | Pb1 | CNL |
| 89 | BAJ33559 | $L^3$ | CNL |
| 90 | BAJ33561 | $L^1$ | CNL |
| 91 | BAJ33562 | $L^{1a}$ | CNL |
| 92 | BAJ33563 | $L^{1c}$ | CNL |
| 93 | BAJ33564 | $L^2$ | CNL |
| 94 | BAJ33565 | $L^{2b}$ | CNL |
| 95 | BAJ33566 | $L^4$ | CNL |
| 96 | BAM17521 | N' | CNL |
| 97 | BAN59294 | Pii | CNL |
| 98 | CAB50786 | Rx1 | CNL |
| 99 | CAB56299 | Rx2 | CNL |
| 100 | CAC29241 | Mla6 | CNL |
| 101 | CAL64731 | Rcg1 | CNL |
| 102 | CUM44200.1 | Sr22 | CNL |
| 103 | CUM44213.1 | Sr45 | CNL |
| 104 | CZT14023.1 | Pm2 | CNL |
| 105 | Not available | NbPrf (Niben101Scf00650g02002XLOC) | CNL |
| 106 | NP_001067618 | NLS1 | CNL |
| 107 | NP_ 001172592 | Pish | CNL |
| 108 | NP_001233995 | Hero A | CNL |
| 109 | Q9ZSD1 | RGC2B (Syn. Dm3) | CNL |
| 110 | ATE88460.1 | Sr13 | CNL |
| 111 | AVK42833.1 | Sr21 | CNL |
| 112 | AYV61514.1 | Sr46 | CNL |
| 113 | Current study | Sr26 | CNL |
| 114 | AAA91022.1 | L6 | TNL |
| 115 | AGQ17378.1 | Sr33 | CNL |
| 116 | ALO61074.1 | Sr50 | CNL |
| 117 | AGP75918.1 | Sr35 | CNL |
| 118 | Current study | Sr61 | CNL |

CC Domain Prediction and Conserved CC Domain Alignment

The coiled-coil domains were determined using the COILS prediction program (Lupas et al., 1991) (https://embnet.vital-it.ch/software/COILS_form.html). The Expresso from T-Coffee program (http://tcoffee.crg.cat/apps,tcoffee/do:expresso) was used for protein sequence alignment.

Structure Modelling of Sr26 and Sr61

The Sr26 and Sr6l protein structures were modelled using SWISS-MODEL (https://swissmodel.expasy.org/) with the template ZAR1-RSK1-PBL2$^{UPM}$ complex (Wang et al., 2019) PDB accession code 6J5V.

Molecular Cytogenetic Characterization of Sr26 and Sr61 Lines

Root tip treatment and slide preparation were according to the procedure in Zhang et al. (2018). Non-denaturing fluorescence in situ hybridization (ND-FISH) with oligonucleotide probes Oligo-pSc119.2-1 and Oligo-pTa535-1 was used to identify individual wheat chromosomes (Tang et al., 2014). Oligo-pScl19.2-1 and Oligo-pTa535-1 were labelled with 6-carboxyfluorescein (6-FAM) and 6-carboxytetramethylrhodamine (Tamra) generating green and red signals, respectively. Chromosomes were counterstained with 4',6-diamidino-2-phenylindole (DAPI) (Invitrogen Life Science. Carlsbad. CA. USA) in Vectashield (Vector Laboratories, Burlingame, CA) and pseudocolored blue.

Slides were analyzed with a Zeiss Axio Imager epifluorescence microscope. Images were captured with a Retiga EXi CCD (charge-coupled device) camera (QImaging, Surrey, BC, Canada) operated with Image-Pro Plus version 7.0 software (Media Cybernetics Inc., Bethesda, MD, USA) and processed with Photoshop version CS6 software (Adobe Systems. San Jose, CA).

After stripping off the oligo probes, the same slides were used to further characterize the Sr26 translocation line Avocet+Lr46, Sr61 substitution line W3757 and the recombinant 378/15 by genomic in situ hybridization (GISH) following the procedure of Zhang et al. (2001). Total genomic DNA from Pseudoroegneria stipilbha (PI 314058, The National Small Grains Collection (NSGC), USDA-ARS, ID) was labelled with biotin-16-dUTP (Roche Diagnostics Australia, Castle Hill, NSW, Australia) using nick translation. Unlabelled total genomic DNA of wheat was used as blocker. The probe to blocker ratio was ~1:80. Signals were detected with fluorescein avidin DN (Vector Laboratories, Burlingame, CA, USA). Chromosomes were counterstained with DAPI and pseudocolored red.

Characterization of T-DNA copy number by Digital PCR

Genomic DNA was isolated from leaf tissues using CTAB extraction. The Phosphinothricin (PPT) selectable marker gene, positioned at the T-DNA left border, was used to establish the copy number of the transgene. The PPT-F/PPT-R primer pair combined with PPT-Probe were provided by Petrie et al. (2020). The probe was labelled with 5'FAM (6-fluorescein) and doubled-quenched with ZENTM and Iowa Black Hole Quencher 1. ~100 ng genomic DNA was digested with 4 units of EcoRI (New England Biolabs, Ipswich, MA, United States) in a final volume of 20 tL, at 37° C. for 4 hours. Samples were placed onto Droplet Generator QX200TM (Bio-Rad) or QX200AutoDG and heat sealed with a pierceable foil heat seal with PXI PCR plate sealer (Bio-Rad). Plates were placed in C1000 Thermal Cycler (Bio-Rad) and reactions were run with the following cycles: 95° C. for 10 min followed by 40 cycles at 94° C. for s; 59° C. for 1 min, then 98° C. for 10 min and finally maintained at 12° C. The ramping rate of 2.5° C./s in all temperature change steps were used. After amplification, the plates were loaded onto the QX200 Droplet Reader (Bio-Rad). Data analysis was performed using Quanta softTM software (Bio-Rad).

Example 2—Identification of Sr61

Grass species related to wheat carry sources of resistance that can be transferred to commercial cultivars. Sr26 is derived from tall wheat grass (Thinopyrum ponticum (Podp.) Barkworth & D.R. Dewey (2n=10x=70)). Its introgression into common wheat as a 6AS.6AL-6Ae #1 chromosome translocation is one of the earliest successful examples of transfer of resistance from a wheat wild relative (Knott, 1961; Dundas et al., 2015). Sr26 was transferred to wheat chromosome 6A by seed irradiation in the early 1960s and this resistance has remained effective against all known Pgt races, including the Ug99 group (Knott. 1961; McIntosh et al., 1977. Park, 2007: Zwer et al. 1992).

A second Th, ponticum-derived Sr gene, Sr61, (previously designated SrB) was identified in South African wheat accession W3757 (Syn. SA8123), which carries a 6Ae #3(6D) chromosome substitution (Singh et al., 1987); to date no known virulence has been reported for Sr61. Whether or not the durability of Sr26 and Sr61 were due to a combined effect from multiple R genes located on the introgressed Th, ponticum alien segment remain unknown. Resistance in W3757 is located on chromosome 6Ae #3 making it possible that Sr26 and Sr61 were allelic (Jenkin, 1984). Recently, a molecular cytogenetic study generated a line in which Sr61 resistance was transferred from 6Ae #3 to the wheat 6AS.6AL-6Ae #1 translocation segment by intercrossing (Mago et al., 2018).

Since no Pgt races virulent to either R genes are available, it was difficult to determine if this introgression carried a single gene or both Sr genes. Molecular markers developed for Sr26 and Sr61 were not reliable indicators of the Sr genes presence in this line as they could be from sequences anywhere in the largely non-recombinogenic transferred alien segment. Given that unambiguous confirmation of the presence of both genes in potential recombinants is difficult using traditional methods, cloning of each gene is the best solution.

Conventional map-based cloning of Sr26 and Sr61 in the wheat derivatives was not feasible due to the absence of homologous recombination between common wheat and tall wheat grass alien chromosome segments. Therefore the inventors used a mutational genomics approach by combining mutational analysis and targeted exome capture of NLR immune receptors, a method termed MutRenSeq (Steuemagel et al., 2016).

Identification of Sr26 Mutants

The inventors identified five susceptible ethyl methanesulfonate (EMS)-induced mutants from the Sr26-carrying wheat genetic stock, Avocet+Lr4623, one of which (150S-1) carried a deletion of a linked marker (FIG. 1; Table 3). These five lines, together with the wild-type Avocet+Lr46, were subjected to NLR gene capture and sequencing and a single contig of 2,466 bp that was absent from 150S-1 and contained a single nucleotide change in each of the other four mutants was identified using MutantHunter (FIG. 2).

The full length gene was isolated from Avocet+Lr46 and encoded a 935 amino acid (aa) protein consisting of a coiled-coil (CC) domain at the N-terminus, an NB-ARC domain and LRR motifs at the C-terminus (CNL) (FIG. 3). Three of the mutants contained amino acid changes in conserved motifs of the NB-ARC domain; Ala311Thr (RNBS-C motif) in mutant 128S and Ser431Asn (RNBS-D motif) in mutants 70S and 12S, which were likely from the same mutation event. The nucleotide change in Mutant 499S occurred at a splice junction and would result in an aberrant transcript (FIGS. 4 to 6).

Identification of Sr61 Mutants

The inventors also identified eight susceptible EMS mutants derived from line W3757 among 1,837 M2 lines thereby enabling isolation of Sr61. Two mutants contained deletions of a previously reported marker MWG798 linked to the gene (Mago et al., 2018). The remaining six mutants (M1 to M6) were potential point mutations and together with wild-type line W3757 were analysed by NLR gene capture and sequencing (FIGS. 1 and 8, Table 3). A single contig of 3,519 bp was identified that contained nucleotide changes in five of the mutants. The full length gene isolated from W3757 encodes a 880 aa protein containing a coiled-coil (CC) domain, NB-ARC domain and LRR motifs (FIG. 3) (SEQ ID NO:1). These nucleotide changes were all non-synonymous and caused amino acid substitutions in the CC (M3, M4), NB-ARC (M2), or LRR (M1, M5, and M6) domains.

TABLE 3

Wild-type and EMS-derived mutants used in the MutRenSeq Pipeline. Mutants were used in MutRenSeq pipeline to identify Sr26 and Sr61 candidate genes. Table S1

| | | Rust response | | | Genotyping result (Sr26 marker #43) | | |
|---|---|---|---|---|---|---|---|
| Mutant | Accession number | R sib (M2) | Mutant (M2) | Progeny test (M3) | R sib (M2) | Mutant (M2) | Mutation Type |
| 12S | 12S-1 | R | S | S | + | + | Putative point mutation (Sr26 marker retained) |
| 70S | 70S-1 | R | S | S | + | + | |
| 128S | 128S-1 | R | S | S | + | + | |
| 499S | 499S-1 | R | S | S | + | + | |
| 150S | 150S-1 | R | S | S | + | − | Putative deletion mutant (Sr26 marker lost) |

| | | Rust response | | | Genotyping result (SrB (Sr61) marker MWG798) | | |
|---|---|---|---|---|---|---|---|
| Mutant | Accession Number | R sib (M2) | Mutant (M2) | Progeny test (M3) | R sib (M2) | Mutant (M2) | Mutation Type |
| M1 | 6421.4S | R | S | S | + | + | Putative point mutation (SrB marker (Sr61) retained) |
| M2 | 6802.4S | R | S | S | + | + | |
| M3 | 7505.4S | R | S | S | + | + | |
| M4 | 7150.4S | R | S | S | + | + | |
| M5 | 5858.4S | R | S | S | + | + | |
| M6 | 7521.4S | R | S | S | + | + | |
| M7 | 6735.5S | R | S | S | + | − | Putative deletion mutant (SrB marker (Sr61) lost) |
| M8 | 6904.4S | R | S | S | + | − | |

DNA amplification and sequencing confirmed the nucleotide changes in this gene in the five mutants, and identified an additional alteration in the sixth mutant (M6). These nucleotide changes were all non-synonymous and caused amino acid substitutions in the CC (M3, M4), the NB-ARC domain (M2), or the LRR domain (M1, M5, and M6) (FIGS. 5, 7 and 8). Variation in resistance specificity can sometimes be caused by changes in LRR regions as shown for Sr13 mutant T4-4367 (Zhang et al., 2017). In our previous study of the Yr5 locus, the Yr5b (YrSP) allele with a distinct specificity was a truncated form of Yr5a (Yr5) (Marchal et al., 2018). In the current study, none of the three mutations in the LRR domain of Sr61 resulted in a new resistance specificity based on the Pgt races tested.

Example 3—Functional Studies

A transgenic complementation experiment was performed to confirm the function of the Sr26 gene. The assembled genomic sequence for the candidate Sr26 gene contained only 917 bp upstream of the start codon and 263 bp downstream of the stop codon, and therefore may not have included sufficient regulatory elements for appropriate gene expression. To ensure proper expression of the candidate gene, three constructs were used to produce transgenic plants (FIG. 4). One construct encompassing the available native sequences was designated Fielder.Sr26:NativeRE (Regulatory Elements). The other two constructs, designated Fielder:Sr26:Sr22RE and Fielder:Sr26:Sr33RE, fused the available native Sr26 gene sequence together with upstream and downstream regulatory elements derived from Sr22 and Sr33 respectively (Periyannan et al., 2013: Steuemagel et al., 2017).

A previous report showed that Sr45 gene function was retained when driven by Sr33 regulatory elements (REs) (Hatta et al., 2018). The inventors generated 21, 22, and 14 independent primary transgenic lines carrying the Fielder: Sr26:NativeRE, Fielder:Sr26:Sr22RE and Fielder:Sr26: Sr33RE constructs, respectively. All 57 independent primary transgenic TO plants were resistant to Pgt race 98-1,2,(3),(5),6 whereas all non-transformed sib Fielder controls were susceptible (FIG. 4*b*, Tables 4 to 6).

TABLE 4

Stem rust responses conferred by three constructs used for the validation of the Sr26 gene candidate. Infection types were recorded for 22 independent T0 plants obtained from construct Fielder:Sr26:Sr22RE. 14 independent T0 plants obtained from construct Fielder:Sr26:Sr33RE.

| Construct | Accession No. | $T_0$ event No. | Infection |
|---|---|---|---|
| Fielder:Sr26:Sr22RE | PC225 | 1 | 1 + 2 − 2 |
| Fielder:Sr26:Sr22RE | PC225 | 2 | 122+ |
| Fielder:Sr26:Sr22RE | PC225 | 3 | 2−, 2 |
| Fielder:Sr26:Sr22RE | PC225 | 4 | ;, 2− |
| Fielder:Sr26:Sr22RE | PC225 | 5 | 1 + 2− |
| Fielder:Sr26:Sr22RE | PC225 | 6 | ;, 1, 2− |
| Fielder:Sr26:Sr22RE | PC225 | 7 | 2 |
| Fielder:Sr26:Sr22RE | PC225 | 8 | 122+ |
| Fielder:Sr26:Sr22RE | PC225 | 9 | 1, 2 |
| Fielder:Sr26:Sr22RE | PC225 | 10 | 2−, 2 |
| Fielder:Sr26:Sr22RE | PC225 | 11 | 1 + 2− |
| Fielder:Sr26:Sr22RE | PC225 | 12 | ; 122+ |
| Fielder:Sr26:Sr22RE | PC225 | 12 | ;, 1, 2= |
| Fielder:Sr26:Sr22RE | PC225 | 13 | 2 |
| Fielder:Sr26:Sr22RE | PC225 | 14 | 1 + 2 |
| Fielder:Sr26:Sr22RE | PC225 | 15 | 1, 2− |
| Fielder:Sr26:Sr22RE | PC225 | 16 | ;, 1−, 1, 2−, 2 |
| Fielder:Sr26:Sr22RE | PC225 | 17 | ;, 2, 2− |
| Fielder:Sr26:Sr22RE | PC225 | 18 | 2−, 2 |
| Fielder:Sr26:Sr22RE | PC225 | 19 | 1, 2 |
| Fielder:Sr26:Sr22RE | PC225 | 20 | 12− |
| Fielder:Sr26:Sr22RE | PC225 | 21 | 1 + 2 |
| Fielder:Sr26:Sr22RE | PC225 | 22 | ;, 1, 2 |
| Non-transformed control | PC225 | 23 | 3+ |

TABLE 5

Stem rust responses conferred by three constructs used for the validation of the Sr26 gene candidate. Infection types were recorded for 22 independent T0 plants obtained from construct Fielder:Sr26:Sr22RE. 22 independent T0 plants obtained from construct Fielder:Sr26:NativeRE.

| Construct | Accession No. | $T_0$ event No. | Infection |
|---|---|---|---|
| Fielder:Sr26:Sr33RE | PC226 | 1 | 2−, 2 |
| Fielder:Sr26:Sr33RE | PC226 | 2 | 1 + 2 |
| Fielder:Sr26:Sr33RE | PC226 | 3 | ;, 22− |
| Fielder:Sr26:Sr33RE | PC226 | 4 | ;, 2− |
| Fielder:Sr26:Sr33RE | PC226 | 5 | 2 |
| Fielder:Sr26:Sr33RE | PC226 | 6 | 1, 2− |
| Fielder:Sr26:Sr33RE | PC226 | 7 | ;, 1, 2− |
| Fielder:Sr26:Sr33RE | PC226 | 8 | 2 + 3 |
| Fielder:Sr26:Sr33RE | PC226 | 9 | 2−, 2 |
| Fielder:Sr26:Sr33RE | PC226 | 10 | 2, 2− |
| Fielder:Sr26:Sr33RE | PC226 | 11 | 2, 2− |
| Fielder:Sr26:Sr33RE | PC226 | 12 | 1, 2− |
| Fielder:Sr26:Sr33RE | PC226 | 13 | 1 + 22+ |
| Fielder:Sr26:Sr33RE | PC226 | 14 | 2, 2+ |
| Non-transformed control | PC226 | 15 | 3+ |

TABLE 6

Stem rust responses conferred by three constructs used for the validation of the Sr26 gene candidate. Infection types were recorded for 22 independent T0 plants obtained from construct Fielder:Sr26:Sr22RE. The Fielder control in each case was a transformed individual with an empty vector.

| Construct | Accession No. | $T_0$ event No. | Infection |
|---|---|---|---|
| Fielder:Sr26:NativeRE | PC253 | 1 | 2− |
| Fielder:Sr26:NativeRE | PC253 | 2 | 2− |
| Fielder:Sr26:NativeRE | PC253 | 3 | 2− |
| Fielder:Sr26:NativeRE | PC253 | 4 | 2− |
| Fielder:Sr26:NativeRE | PC253 | 5 | 2 |
| Fielder:Sr26:NativeRE | PC253 | 6 | 2= |
| Fielder:Sr26:NativeRE | PC253 | 7 | 2= |
| Fielder:Sr26:NativeRE | PC253 | 8 | 2= |
| Fielder:Sr26:NativeRE | PC253 | 9 | 2= |
| Fielder:Sr26:NativeRE | PC253 | 10 | 1= |

TABLE 6-continued

Stem rust responses conferred by three constructs used for the validation of the Sr26 gene candidate. Infection types were recorded for 22 independent T0 plants obtained from construct Fielder:Sr26:Sr22RE. The Fielder control in each case was a transformed individual with an empty vector.

| Construct | Accession No. | $T_0$ event No. | Infection |
|---|---|---|---|
| Fielder:Sr26:NativeRE | PC253 | 11 | 1= |
| Fielder:Sr26:NativeRE | PC253 | 12 | 2= |
| Fielder:Sr26:NativeRE | PC253 | 13 | 2= |
| Fielder:Sr26:NativeRE | PC253 | 14 | ; |
| Fielder:Sr26:NativeRE | PC253 | 15 | 0; |
| Fielder:Sr26:NativeRE | PC253 | 16 | 0; |
| Fielder:Sr26:NativeRE | PC253 | 17 | 2= |
| Fielder:Sr26:NativeRE | PC253 | 18 | 1; |
| Fielder:Sr26:NativeRE | PC253 | 19 | 1; |
| Fielder:Sr26:NativeRE | PC253 | 20 | ; |
| Fielder:Sr26:NativeRE | PC253 | 21 | ; 1= |
| Non-transformed control | PC253 | 22 | 3+ |

Figure 16B:
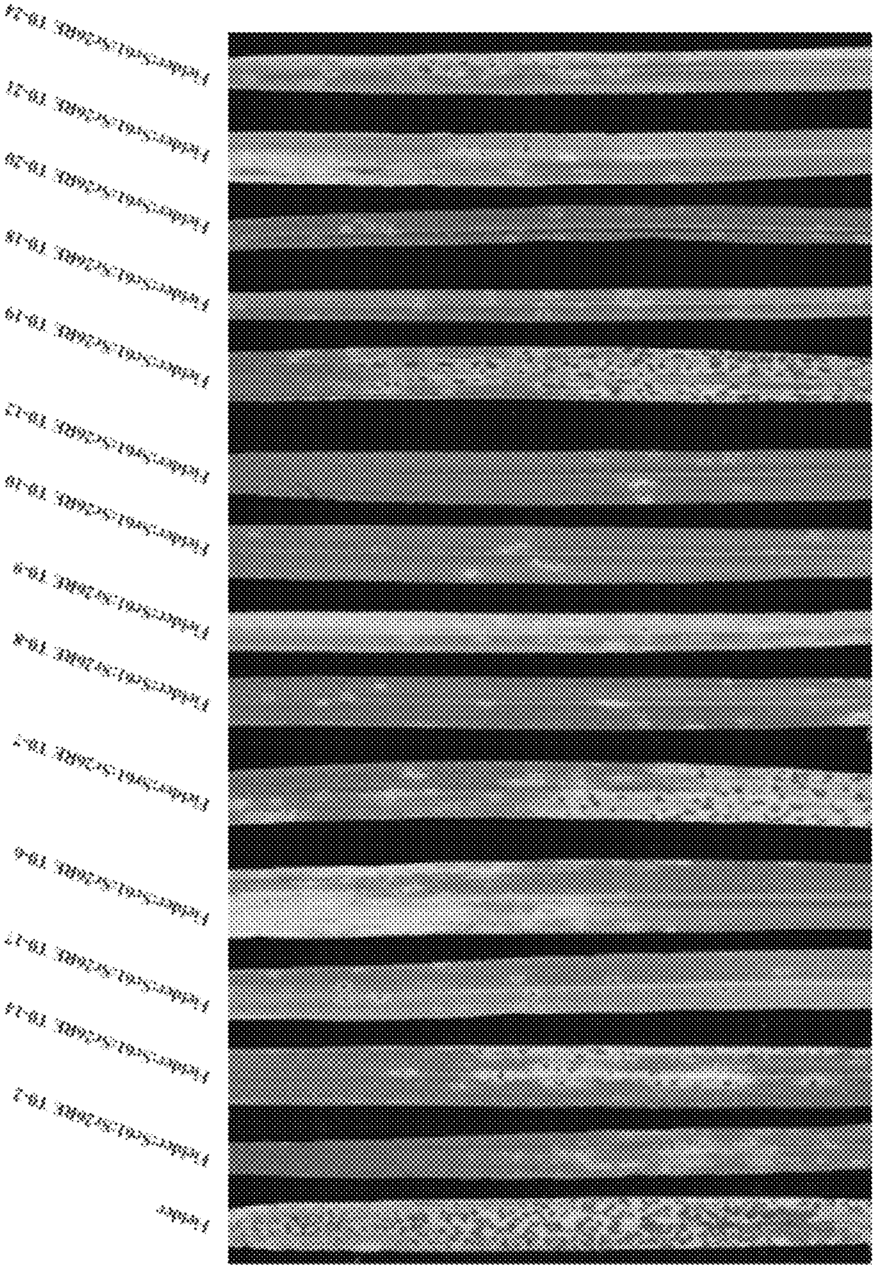

A transgenic complementation experiment was also performed to confirm the function of the Sr61 gene. The assembled genomic sequence for the Sr61 candidate contained 354 bp upstream of the start codon and 67 bp downstream of the stop codon, and therefore may not have included sufficient regulatory elements for appropriate gene expression. To ensure proper expression of the candidate gene, a construct designated Fielder:Sr61:Sr26RE, fused to the putative native Sr61 gene sequence with the upstream and downstream regulatory elements derived from Sr26. The inventors generated 21 independent primary transgenic lines carrying Fielder:Sr61:Sr26RE construct. Among the 21 lines, 14 independent primary transgenic $T_0$ plants were selected and inoculated with Pgt race 98-1,2,(3),(5),6. All 14 lines showed resistance whereas all non-transformed Fielder controls were susceptible to Pgt race 98-1,2,(3),(5),6 (FIG. 16*b*). Thus, the Sr61 gene candidate was shown to be necessary confer Sr61 resistance to Pgt race 98-1,2,(3),(5),6 but also sufficient of itself to confer Sr61 resistance (Tables 3 and 7). Twelve transgenic lines from six independent TI families were selected to further test their phenotype and the transgenic copy numbers (FIG. 17).

TABLE 7

Multiple Pgt tests on the wild-types and mutants of Sr26 and Sr61.
Multiple Pgt tests on seedling Sr26 and Sr61 wildtype and mutants

| Pgt Races | Avocet | Sr26 Mutant 12S/70S | Sr26 Mutant 128S | Sr26 Mutant 499S | Sr26 Mutant 150S | W3757 | M1 | M2 | M3 | M4 | M5 | M6 | M7 | M8 | Recombinant 376/15 | Recombinant 378/15 | Recombinant 388/15 |
|---|---|---|---|---|---|---|---|---|---|---|---|---|---|---|---|---|---|
| 34-1, 2, 3, 4, 5, 6, 7 | R | S | S | S | S | R | S | S | S | S | S | S | S | S | R | R | R |
| 98-1, 2, (3), (5), 6 | R | S | S | S | S | R | S | S | S | S | S | S | N/A | N/A | R | R | R |
| 21-0 | R | S | S | S | S | R | S | S | S | S | S | S | N/A | N/A | R | R | R |
| PTKST | R | S | N/A | S | N/A | R | N/A | S | N/A | S | N/A | S | N/A | N/A | R | R | N/A |
| TTKTT (KE178b/18) | R | S | N/A | N/A | N/A | R | N/A | S | N/A | S | N/A | S | N/A | N/A | R | R | R |
| TTRTF | R | S | N/A | S | N/A | N/A | N/A | N/A | N/A | N/A | N/A | N/A | N/A | N/A | R | R | R |

TABLE 8

| Oligonucleotide primers. | | | |
|---|---|---|---|
| | Primer Name | Sequence (5' to 3') | Tm ° C. |
| Sr26 Sequence Primers | Sr26Seq1R | TCGGAATCGTTCCCGTGAATTGAAGCTA (SEQ ID NO: 23) | — |
| | Sr26Seq2R | ATGCTCAGGATAAGGCGTGGATGAATGAGGT (SEQ ID NO: 24) | |
| | Sr26Seq3F | GGGGAGATCAAATCGCTCACTCAT (SEQ ID NO: 25) | |
| | Sr26Seq4F | GTACAATTTCAGTTTTAACTTCTCATCCTTGAG (SEQ ID NO: 26) | |
| | Sr26Seq5F | TACAGTATGAGCTGACCCAGCGG (SEQ ID NO: 27) | |
| | Sr26Seq6F | GGATAGACAATGAAAAATGAGGA (SEQ ID NO: 28) | |
| | Sr26Seq7F | GCTTTTCTTGATTTAAAATCATAGGATGT (SEQ ID NO: 29) | |
| | Sr26Seq8R | GATATTATTGTCGCTTCCCTTAAAAAC (SEQ ID NO: 30) | |
| | Sr26Seq9F | TTCCGAGGGTCATAGTCTCTGGC (SEQ ID NO: 31) | |
| | Sr26Seq10R | TCTCCCACAAAAGGCCATGTACTTCTTTAATTCACAAG (SEQ ID NO: 32) | |
| Sr26 Gene Specific primers | Sr26GSPF | GGAATACTCGAATACCAGGCCAT (SEQ ID NO: 33) | 58 |
| | Sr26GSPR | TTGCCACTGTGAACATGTTTATAGAT (SEQ ID NO: 34) | |
| Sr61 Sequence Primers | Sr61Seq1 | GCAGGTAACTCACAAGCATAACTAGGAG (SEQ ID NO: 35) | — |
| | Sr61Seq2 | GCCAATGAGGTGTACCATATG (SEQ ID NO: 36) | |
| | Sr61Seq3 | ATGCACTAAAGGTAGATCCTGG (SEQ ID NO: 37) | |
| | Sr61Seq4 | ATTATAATCAAGTACCTGCCAACATT (SEQ ID NO: 38) | |
| | Sr61Seq5 | ACAAAAGGAAAGGTGGAAGG (SEQ ID NO: 39) | |
| | Sr61Seq6 | GACGAGCCTTGTAATCCAA (SEQ ID NO: 40) | |
| | Sr61Seq7 | CGATATCTACGTGCATTTGATTTACG (SEQ ID NO: 41) | |
| | Sr61Seq8 | AACCAACAATTCGATGACACAAGG (SEQ ID NO: 42) | |
| | Sr61Seq9 | CAGACTCTGCCCATTCCGT (SEQ ID NO: 43) | |
| | Sr61Seq10 | TGCACATACTAGCCGCTTGATATTT (SEQ ID NO: 44) | |
| Sr61 Gene Specific primers | Sr61GSPF | AACCAACAATTCGATGACACAAGG (SEQ ID NO: 45) | 62 |
| | Sr61GSPR | CGATATCTACGTGCATTTGATTTACG (SEQ ID NO: 46) | |

A total of 46 T1 plants derived from four independent transgenic events, two from each construct of Fielder:Sr26:Sr22RE and Fielder:Sr26:Sr33RE, were all resistant against Pgt race 98-1,2,(3),(5),6 whereas all sib Fielder controls lacking the transgene were susceptible (FIGS. 9 and 10). Thus, the gene candidate was not only necessary but also sufficient to confer Sr26 resistance (Tables 3 and 6). These data also indicate that the minimal flanking regions identified for the Sr26 gene were sufficient to direct its appropriate expression. A previous report showed that Sr45 gene function was not compromised wien driven by Sr33 REs (Hatta et al., 2018). In the current study, the inventors show that the existence of the additional Sr22 and Sr33 promoter and terminator sequences did not abolish Sr26 gene function.

Example 4—Marked Assisted Breeeding

To facilitate the use of Sr26 and Sr61 in breeding and allow their reliable identification in combination with other genes and in the recombinant introgression segment described previously (Mago et al., 2018), the present inventors developed gene-specific markers for each gene. For Sr26, a 1,580 bp PCR amplicon was identified that flanked the intron I—exon II junction and is highly specific for Sr26. For Sr61, a marker with an amplicon size of 207 bp located in the first exon was also confirmed to be Sr61-specific (FIG. 11, Table 8).

Using these markers, the inventors confirmed the presence of both Sr26 and Sr61 in the recombinant line (FIG. 11). Molecular cytogenetic analysis showed that the alien segment in the recombinant line was smaller than that in both the 6AS.6AL-6Ae #1 translocation and the 6Ae #3 chromosome substitution line (FIG. 12).

To test the responses conferred by Sr26 and Sr61 against newly emerged Pgt races PTKST (collected in South Africa), TRTF (collected in Italy and Eritrea), and TTKTT (collected in Kenya), plants containing either gene singly or in combination were rust phenotyped. In all assays, lines with both Sr26 and Sr61 were consistently more resistant than the lines carrying each gene alone (FIGS. 13 and 14).

Example 5—Evolutionary Relationship of Sr26, Sr61 to Other CNL R Plant Proteins To determine the evolutionary relationship of Sr26, Sr61 to other CNL R plant proteins the inventors generated a phylogenetic tree based on the alignment of 117 CNL-type R genes (Kourelis et al., 2018) together with the L6 flax rust resistance Toll!interleukin-1 receptor (TIR) protein as an outgroup (FIG. 15, Table 2). Although both Sr26 and Sr61 originated from tall wheat grass, the most closely related R gene to Sr26 was the *T. turgidum* ssp. *dicoccoides* gene Sri3 (58.46% identity at protein level) (FIG. 15). Sr61 is much less similar to either Sr13 (35.21%) or Sr26 (34.81%) but all three genes are members of a clade that includes Sr22, Sr33, Sr35, Sr50, Sr46, and the barley Mla R gene family (FIGS. 15, Clade I, 3b). By contrast Sr21 and Sr45 occur in distant clades and related to the wheat powdery mildew R gene Pm3 alleles (FIG. 15, Clade II); none of the current Sr genes were in the more divergent and broader clade III (FIG. 15).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from AU 2019904238 filed 11 Nov. 2019, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotechnology 4:1087.
Arora et al. (2019) Nature Biotechnology 37:139-143.
Ayliffe et al. (2013) Mol Plant Microbe Interact 26:658-667.
Barn et al. (2008) Proc S Afr Sug Technol Ass 81:508-512.
Barker et al. (1983) Plant Mol. Biol. 2: 235-350.
Begemann et al. (2017) Sci Rep. 7(1):11606.
Bender et al. (2016) Plant Disease 100:1627-1633.
Bevan et al. (1983) Nucl. Acid Res. 11: 369-385.
Bulgarelli et al. (2010) PLoS One 5:e12599.
Cadwell and Joyce (1992) PCR Methods Appl. 2:28-33.
Capecchi (1980) Cell 22:479-488.
Chen et al. (2018) PLoS Genet 14, e1007287, doi:10.1371/joumal.pgen.1007287.
Chen et al. (2019) New Phytol, doi:10.1111/nph.16169.
Cheng et al. (1996) Plant Cell Rep. 15:653-657.
Clapp (1993) Clin. Perinatol. 20:155-168.
Coco et al. (2001) Nature Biotechnology 19:354-359.
Coco et al. (2002) Nature Biotechnology 20:1246-1250.
Cooley et al. (2000) Plant Cell 12:663-676.
Comai et al. (2004) Plant J 37: 778-786.
Crameri et al. (1998) Nature 391:288-291.
Curiel et al. (1992) Hum. Gen. Ther. 3:147-154.
Delorenzi and Speed (2002) Bioinformatics. 18:617-25.
Dilbirligi et al. (2003) Plant Mol Biol. 53:771-87.
Doudna and Charpentier (2014) Science 28:346(6213): 1258096.
Dundas et al. (2015) Crop Science 55:648-657.
Eggert et al. (2005) Chembiochem 6:1062-1067.
Eglitis et al. (1988) Biotechniques 6:608-614.
Enkhbayar et al. (2004) Proteins 54:394-403.
Fujimura et al. (1985) Plant Tissue Cultural Letters 2:74.
Garfinkel et al. (1983) Cell 27: 143-153.
Gennaro et al. (2009) Funct Integr Genomics. 9:325-34.
Graham et al. (1973) Virology 54:536-539.
Grant et al. (1995) Plant Cell Rep. 15:254-258.
Greve (1983) J. Mol. Appl. Genet. 1:499-511.
Haft et al. (2005) Computational Biology. PLoS Comput Biol I(6):e60.
Harayama (1998) Trends Biotechnol. 16:76-82.
Hellinga (1997) Proc. Natl. Acad. Sci. 94:10015-10017.
Henikoff et al. (2004) Plant Physiol 135: 630-636.
Hatta et al. (2018) https://www.biorxiv.org/content/early/2018/07/23/374637
Hinchee et al. (1988) Biotech. 6:915
Ishida et al. (2015) *Agrobacterium* Protocols. Vol 1, 3rd Edition 1223:189-198.
Jenkin (1984) Isozyme variation of the 9A-1 translocation and genetic mapping of its breakpoint in wheat cultivars Eagle and Kite Honours thesis, The University of Adelaide. Australia.
Jezdquel et al. (2008) Biotechniques 45:523-532.
Jinek et al. (2012) Science 337:816-821.
Joshi (1987) Nucl. Acid Res. 15: 6643-6653.
Knott (1961) Canadian Journal of Plant Science 41:109-123.
Langridge et al. (2001) Aust. J. Agric. Res. 52: 1043-1077.
Kourelis et al. (2018) Plant Cell 30:285-299.
Lemieux (2000) Current Genomics 1: 301-311.
Leung et al. (1989) Technique 1:11-15.
Li et al. (2019) bioRxiv, 692640, doi:10.1101/692640.
Liang et al. (2017) Nat Commun. 8:14261.
Liang et al. (2018) Plant Biotechnol J. 16:2053-2062.
Liang et al. (2019) Methods Mol Biol. 1917:327-335.
Lu et al. (1993) J. Exp. Med. 178: 2089-2096.
Luo et al. (2016) Plant Cell Rep 35(7):1439-1450.
Lupas et al. (1991) Science 252:1162-1164.
Ma et al. (2015) Molecular Plant 8: 1274-1284.
Marchal et al. (2018) Nat Plants 4:662-668.
Mago et al. (2015) Nat Plants 1, 15186, doi:10.1038/nplants.2015.186.
Mago et al. (2018) Theoretical and Applied Genetics, doi: 10.1(X7/s00122-018-3224-1.
Makarova (2015) Nat. Rev. Microbiol. 13:722-736.
McHale et al. (2006) Genome Biology 7:212.
Mcintosh et al. (1977) Australian Journal of Agricultural Research 28:3745.
McIntosh et al. (1995). Wheat rusts: An atlas of resistance genes. (CSIRO Australia).
Medberry et al. (1992) Plant Cell 4: 185-192.
Medberry et al. (1993) Plant J. 3: 619-626.
Meyers et al. (1999) Plant Journal 20:317-332.
Michelmore and Meyers (1998) Genome Res. 8:1113-1130.
Needleman and Wunsch (1970) J. Mol Biol. 45:443-453.
Ness et al. (2002) Nature Biotechnology 20:1251-1255.
Niedz et al. (1995) Plant Cell Reports 14: 403406.
Olivera et al. (2012) Plant Disease 96, 623-628.
Ostermeier et al. (1999) Nature Biotechnology 17:1205-1209.
Ow et al. (1986) Science 234: 856-859.
Pan et al. (2000) J. Mol. Evol. 50:203-2013.
Park (2007) Australian Journal of Agricultural Research 58:558-566.
Patpour et al. (2018) BGRI Technical Workshop.
Periyannan et al. (2013) Science 341:786-788.
Petrie et al. (2020) Front. Plant Sci 11:Article 727.
Prasher et al. (1985) Biochem. Biophys. Res. Comm. 126: 1259-68.
Pretorius et al. (2015) Phytoparasitica 43:637-645.
Saintenac et al. (2013) Science 341:783-786.
Salomon et al. (1984) EMBO J. 3: 141-146.
Sieber et al. (2001) Nature Biotechnology 19:456-460.
Singh and Mcintosh (1987) Theoretical and Applied Genetics 73:846-855.
Singh et al. (2015) Phytopathology 105, 872-884.
Slade and Knauf (2005) Transgenic Res. 14: 109-115.
Stalker et al. (1988) Science 242:419-423.
Stemmer (1994a) Proc. Natl. Acad. Sci. USA 91:10747-10751.
Stemmer (1994b) Nature 370(6488):389-391.
Steuemagel et al. (2016) Nat Biotechnol 34, 652-655.
Sun et al. (2016) Molecular Plant 9: 628-631.
Svitashev et al. (2016) Nat Commun. 7:13274.
Takken et al. (2006) Curr Opin Plant Biol. 9:383-90.
Tameling et al. (2002) Plant Cell 14:2929-2939.
Tang et al. (2014) J Appl Genet 55:313-318.
Thillet et al. (1988) J. Biol. Chem. 263:12500.
Toriyama et al. (1986) Theor. Appl. Genet. 205:34.
Traut (1994) Eur J Biochem. 222:9-19.
Volkov et al. (1999) Nucleic Acids Research 27:e18.
Wagner et al. (1992) Proc. Natl. Acad. Sci. USA 89:6099-6103.
Wang et al. (2011) New Phytologist. 191: 418-431.
Wang et al. (2019) 364, doi:10.1126/science.aav5868.
Woo et al. (2015) Nat Biotechnol. 33:1162-1164.

Yu et al. (2017) Methods Mol Biol 1659:207-213.
Zhang et al. (2001) Chromosoma 110:335-344.
Zhang et al. (2017). Proc Natl Acad Sci USA 114: E9483-E9492.
Zhang et al. (2018) Theor Appl Genet, doi:10,1007/s00122-018-3201-8.
Zhao et al. (1998) Nature Biotechnology 16:258-261.
Zwer et al. (1992) Aust. J. Agric. Res. 43:399-431.

The invention claimed is:

1. A genetically modified plant comprising a transgene encoding a polypeptide which confers resistance to at least one strain of *Puccinia graminis*, wherein the polypeptide comprises amino acids having a sequence as provided in SEQ ID NO:1, or an amino acid sequence which is at least 95% identical to SEQ ID NO:1.

2. The plant of claim 1, wherein the *Puccinia graminis* is *Puccinia graminis* f. sp. *tritici.*

3. The plant of claim 1, wherein the polypeptide comprises amino acids having a sequence which is at least 99% identical to SEQ ID NO:1.

4. The plant of claim 1 which is a cereal plant.

5. The plant of claim 1 which comprises one or more exogenous polynucleotides encoding another plant pathogen resistance polypeptide.

6. The plant of claim 1 which is homozygous for the modification.

7. A process for identifying a polynucleotide encoding a polypeptide which confers resistance to at least one strain of *Puccinia graminis* comprising:

i) obtaining a polynucleotide operably linked to a promoter, the polynucleotide encoding a polypeptide comprising amino acids having a sequence as provided in SEQ ID NO:1, or an amino acid sequence which is at least 9% identical to SEQ ID NO:1, ii) introducing the polynucleotide into a plant by transgenesis, iii) determining whether the level of resistance to *Puccinia graminis* is modified relative to an isogenic plant lacking the polynucleotide, and iv) optionally, selecting a polynucleotide which when expressed confers resistance to *Puccinia graminis.*

8. A method of producing the plant of claim 1, the method comprising the steps of:

i) genetically modifying a plant cell to comprise a transgene encoding a polypeptide which confers resistance to at least one strain of Puccinia graminis, wherein the polypeptide comprises amino acids having a sequence as provided in SEQ ID NO:1, or an amino acid sequence which is at least 95% identical to SEQ ID NO:1, ii) regenerating a plant from the cell, and iii) optionally harvesting seed from the plant, and/or iv) optionally producing one or more progeny plants from the plant, thereby producing the plant.

9. A method of producing the plant of claim 1, the method comprising the steps of:

i) crossing two parental plants, wherein at least one plant comprises a transgene encoding a polypeptide which confers resistance to at least one strain of Puccinia graminis, wherein the polypeptide comprises amino acids having a sequence as provided in SEQ ID NO:1, an amino acid sequence which is at least 95% identical to SEQ ID NO:1, ii) screening one or more progeny plants from the cross for the presence or absence of the transgene, and iii) selecting a progeny plant which comprises the transgene, thereby producing the plant.

10. A method for identifying a plant comprising a polynucleotide encoding a polypeptide which confers resistance to at least one strain of Puccinia graminis, the method comprising the steps of i) obtaining a nucleic acid sample from a plant, and ii) screening the sample for the presence or absence of the polynucleotide encoding a polypeptide which confers resistance to at least one strain of Puccinia graminis, wherein the polypeptide comprises amino acids having a sequence as provided in SEQ ID NO:1, or an amino acid sequence which is at least 95% identical to SEQ ID NO:1, using a method selected from nucleic acid amplification, nucleic acid sequencing, nucleic acid hybridization with suitably labelled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof.

11. A seed of the plant of claim 1, wherein the seed comprises the transgene.

12. A method of producing a plant part, the method comprising, a) growing the plant of claim 1, and b) harvesting the plant part.

13. A method of producing flour, wholemeal, starch or other product obtained from seed, the method comprising;

a) obtaining the seed of claim 11, and b) extracting the flour, wholemeal, starch or other product.

14. A product produced from the plant of claim 1 or seed therefrom, wherein the product is a food product or beverage product, and wherein the seed comprises the transgene.

15. A method of preparing the food product of claim 14, the method comprising mixing seed comprising the transgene, or flour, wholemeal or starch from the seed, with another food ingredient.

16. Flour or wholemeal comprising a transgene encoding polypeptide which confers resistance to at least one strain of *Puccinia graminis*, wherein the polypeptide comprises amino acids having a sequence as provided in SEQ ID NO:1, or an amino acid sequence which is at least 95% identical to SEQ ID NO:1.

17. The plant of claim 1, wherein the plant is a *Triticum sp.*

18. The plant of claim 1, wherein the transgene is at a different locus to a native gene encoding the polypeptide.

19. The plant of claim 1, wherein the plant comprises a transgene encoding one or more of Lr34, Lr1, Lr3, Lr2a, Lr3ka, Lr11, Lr13, Lr16, Lr17, Lr18, Lr21, LrB, Lr67, Lr46, Sr50, Sr33, Sr13, and Sr35.

* * * * *